US011504315B2

(12) United States Patent
Furtado Grafin Von Ysenburg-Philippseich et al.

(10) Patent No.: US 11,504,315 B2
(45) Date of Patent: Nov. 22, 2022

(54) COMPOSITIONS FOR LONG-LASTING MOISTURIZING COSMETIC FORMULATION COMPRISING UCUUBA BUTTER WITH HIGH CONCENTRATION OF MYRISTIC ACID, AS WELL AS THE USE OF SAID FORMULATION FOR THE PREPARATION OF A HIGHLY MOISTURIZING COSMETIC PRODUCT AND KIT

(71) Applicant: NATURA COSMÉTICOS S.A., São Paulo (BR)

(72) Inventors: Aurora Maria Domingues Furtado Grafin Von Ysenburg-Philippseich, São Paulo (BR); Simone Emidio, São Paulo (BR); Daniela Veloso Okuta, São Paulo—SP (BR); Debora Cristina Castellani, São Paulo—SP (BR); Mariane Spadoto, São Paulo—SP (BR); Roberta Gisele de Souza Oliveira Pereira, São Paulo—SP (BR); Roberta Roesler, São Paulo—SP (BR); Wagner Franzin Rusca, São Paulo—SP (BR)

(73) Assignee: Natura Cosméticos S.A., São Paulo SP (BR)

( * ) Notice: Subject to any disclaimer, the term of this patent is extended or adjusted under 35 U.S.C. 154(b) by 372 days.

(21) Appl. No.: 15/130,461

(22) Filed: Apr. 15, 2016

(65) Prior Publication Data
US 2016/0303036 A1 Oct. 20, 2016

Related U.S. Application Data

(60) Provisional application No. 62/147,963, filed on Apr. 15, 2015.

(51) Int. Cl.
*A61K 8/36* (2006.01)
*A61Q 19/00* (2006.01)
*A61K 8/92* (2006.01)
*A61K 8/9789* (2017.01)
*A61K 8/9794* (2017.01)

(52) U.S. Cl.
CPC .............. *A61K 8/361* (2013.01); *A61K 8/922* (2013.01); *A61K 8/9789* (2017.08); *A61K 8/9794* (2017.08); *A61Q 19/007* (2013.01); *A61K 2800/87* (2013.01)

(58) Field of Classification Search
CPC .............................. A61K 8/922; A61K 36/185
See application file for complete search history.

(56) References Cited

U.S. PATENT DOCUMENTS

2006/0210505 A1 9/2006 Clapp et al.
2011/0256075 A1* 10/2011 Oliveira Dias ........ A61K 8/922
424/59

FOREIGN PATENT DOCUMENTS

| FR | 293 4495 A1 | 2/2010 |
|---|---|---|
| WO | WO 01/70187 A1 | 9/2001 |
| WO | WO 2005/117849 A1 | 12/2005 |
| WO | WO 2009/139884 A1 | 11/2009 |
| WO | WO 2011/011840 A1 | 2/2011 |
| WO | WO 2011/109472 A1 | 9/2011 |

OTHER PUBLICATIONS

"Ucuuba butter". Technical Data Sheet. Internet date: Jul. 8, 2017. Retrived from the Internet: <URL: https://cdn.shopify.com/s/files/1/0478/8057/files/Ucuuba_TDS.pdf>. (Year: 2017).*
Duke, JA. Handbook of nuts, CRC Press in Boca Raton, FL.,2001. p. 292. (Year: 2001).*
Gehring, A. R. "Soap Making" and "Soap Oils" from "The Illustrated Encyclopedia of Country Living", 2011, pp. 501 and 504 (Year: 2011).*
International Search Report and Written Opinion for Application No. PCT/BR2016/050083 dated Jul. 15, 2016, 10 pages.
International Preliminary Report on Patentability (Chapter II) for Application No. PCT/BR2016/050083 dated Sep. 20, 2017, 7 pages.
Clay, J. W. et al., *Selected Species and Strategies to Enhance Income Generation From Amazonian Forests*, "Uccuba", Food and Agriculture Organization of the United Nations, Rome (May 1993) 269 pages.
Fregonesi, A. et al., *Brazilian Oils and Butters: The Effect of Different Fatty Acid Chain Composition on Human Hair Physiochemical Properties*, J. Cosmet. Sci. 60 (Mar./Apr. 2009) 273-280.
Uccuba Butter—All About the Best Natural and Butters [online] [retrieved Apr. 9, 2019]. Retrieved from the Internet: <URL: https://web.archive.org/web/20160614012213/http://www.naturaloilsandbutters.com/uccuba-butter/>, (Jan. 24, 2015) 4 pages.
Blank, I. H. et al., *The Diffusion of Water Across the Stratum Corneum as a Function of Its Water Content*, The Journal of Investigative Dermatology, vol. 82, No. 2 (1984) 188-194.
Blank, I. H., *Factors Which Influence the Water Content of the Stratum Corneum*, J. Invest. Dermatol. 18 (1952) 433-440.
Clar, E., Os cuidados cosméticos—Pele seca., Prunieras. M. (ed) Manual de Cometologia Dermatológica Andrei 2a ed, (1994) 211-332.

(Continued)

*Primary Examiner* — Amy L Clark
(74) *Attorney, Agent, or Firm* — Alston & Bird LLP

(57) ABSTRACT

The present invention relates to cosmetic formulations with a high moisturizing power comprising, as active principle, ucuuba (*Virola surinamensis*) butter comprising myristic acid in high concentration, more particularly in a concentration equal to or greater than 70% of the constitution of said butter. Additionally, the invention relates to products comprising such cosmetic formulations, as well as to the use of ucuuba butter for the preparation of a differentiated cosmetic product with high skin moisturizing power, as will be demonstrated in the present patent application. The invention further discloses a cosmetic kit comprising the formulation disclosed with a suitable applicator and instructions for use.

3 Claims, 7 Drawing Sheets

(56) References Cited

OTHER PUBLICATIONS

Gall, Y. et al., *5.2—Skin Care Products for Normal, Dry, and Greasy Skin*, Cosmetology for Normal Skin (1994) 89-110.
Hartop, P. J. et al., *Changes in Transepidermal Water Loss and the Composition of Epidermal Lecithin After Applications of Pure Fatty Acid Triglycerides to the Skin of Essential Fatty Acid-Deficient Rats*, British Journal of Dermatology, 95 n.3 (1976) 255-264.
Klingman, A. M. et al., *Some Aspects of Dry Skin and Its Treatment*, Safety and Efficacy of Topical Drugs and Cosmetics, (1982) 221-238.
Korstanje, C, et al., *Differential Effects of Dermatological Cream Bases With Respect to Skin Surface moisturizing Capacity: A Study Design in Volunteers*, Journal of Dermological Treatment 2 (1992) 137-139.
Leveque, J. L., *Physical Methods to Measure the Efficiency of Cosmetics in Humans*, Cosmetics & Toiletries, vol. 99 (1984) 43-50.
Leveque, J. L. et al., *Transepidermal Water Loss From Dry and Normal Skin*, J. Soc. Cosmet. Chem., 30 (Nov. 1979) 333-343.
Nicholls, S. et al., *Short Term Effects of Emollienis and a Bath Oil on the Stratum Corneum*, J. Soc. Cosmet. Chem. 29 (1978) 617-625.
Prall, J. K. et al., *The Effectiveness of Cosmetic Products in Alleviating a Range of skin Dryness conditions as Determined by Clinical and Instrumental Techniques*, International Journal of Cosmetic Science, 8 (1986) 159-174.
Rodrigues, L., *Bioengenharia Cutanea: Novas Perspectivas Sobre a Fisiologia da Pele*, Cosmetics & Toiletries, vol. 8 (Jul. 1996) 51-55.
Spencer, T. S., *Dry Skin and Skin Moisturizers*, Clinics Dermatol., 6 (1988) 24-28.
Spencer, T. S., *Transepidermal Water Loss: Methods and Applications*, Methods for Cutaneous Investigations, Cosmetic Sci. Tech., Series 9 (1990) 191-217.
Tagami, H. et al., *Evaluation of the Skin Surface Hydration in Vivo by Electrical Measurement*, The Journal of Investigative Dermatology, 75 (1980) 500-507.
Valaplana, J. et al., *Clinical and Non-Invasive Evaluation of 12% Ammonium Lactate Emulsion for the Treatment of Dry Skin in Atopic and Non-Atopic Subjects*, Acta Derm Venereol, 72 (1992) 28-33.

\* cited by examiner

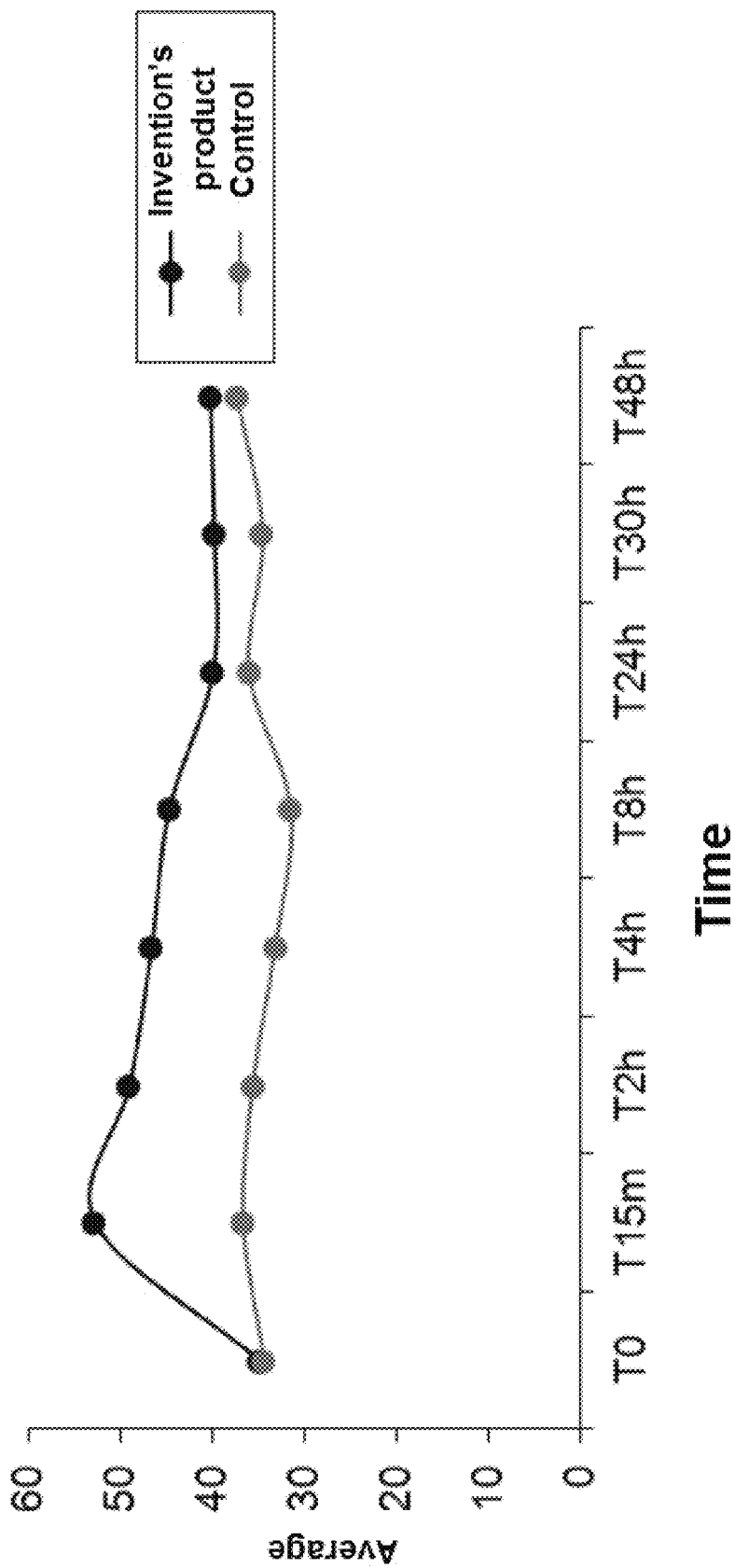

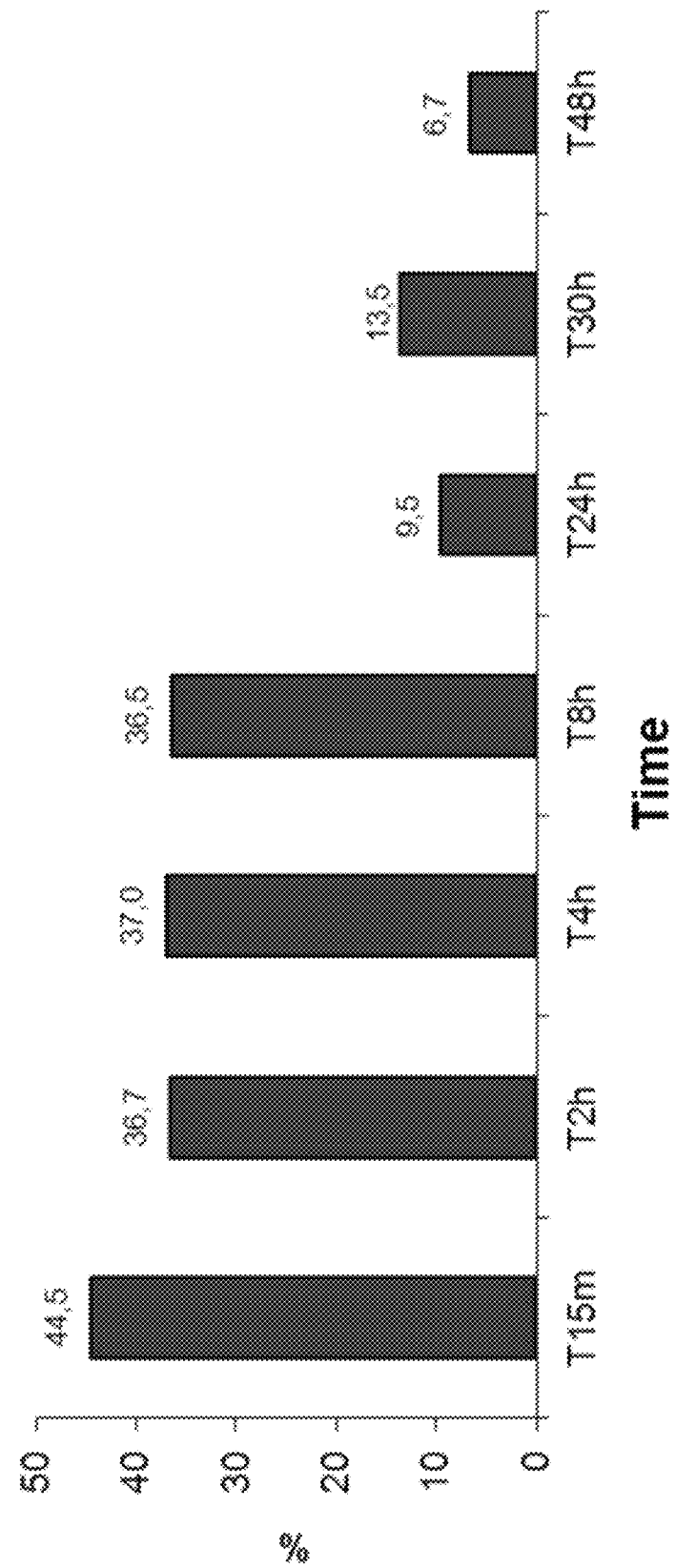

COMPOSITIONS FOR LONG-LASTING MOISTURIZING COSMETIC FORMULATION COMPRISING UCUUBA BUTTER WITH HIGH CONCENTRATION OF MYRISTIC ACID, AS WELL AS THE USE OF SAID FORMULATION FOR THE PREPARATION OF A HIGHLY MOISTURIZING COSMETIC PRODUCT AND KIT

CROSS-REFERENCE TO RELATED APPLICATIONS

The present application claims the benefit of U.S. Provisional Application Ser. No. 62/147,963, filed Apr. 15, 2015, said application incorporated herein by reference.

FIELD OF INVENTION

The present invention refers to highly moisturizing cosmetic formulations with dry and powdery touch comprising ucuuba (*Virola surinamensis*) butter as active ingredient, the ucuuba butter having a high concentration of myristic acid, more particularly in a concentration of more than 70% of the composition of said butter.

BACKGROUND OF THE INVENTION

The use of ucuuba in the Amazon estuary region comes from before colonization, when the Indians used its seeds and bark for producing hallucinogens in shamanic rituals. Since pre-Colombian times the Indians were using some species of *Virola*, which they called "hiboucauhu", "bicuda" and "ucuuba". Ucuuba means in tupi "the tree that produces fatty substance"; its etymology comes from the words uku (fat, grease) and ubá (tree). The *Virola* species are useful in popular medicine for curing several diseases. The Indians carried in their trips the tallow of the seeds for use in wounds.

The oil extracted from the seeds (Ucuuba tallow), rich in trimyristin and with pleasant smell, can be used in the production of candles, soaps, cosmetics and perfumes. The tallow and the sap have several applications in home medicine, especially in the treatment of rheumatism, arthritis, cramps, mouth ulcers and hemorrhoids. Scientific studies are being conducted regarding the use of tallow in the treatment of malaria and Chagas disease. The tree provides an abundance of fruits for birds and other wildlife animals, being therefore useful in the recovery of degraded and preserved areas.

The exploitation history of *Virola* or ucuuba went through different phases of the extracting process. First there was the extraction of the *Virola* seeds, which reached its peak in the 60ties and 70ties, when they were used in the cosmetic and pharmaceutical industry. The turning point in the extraction of ucuuba occurred in 1954, when a pilot of the US Air Force detected the large concentration of ucuuba in the Marajo Island region and sent logs to be tested by the company Georgia Pacific Co. in the United States. The conducted tests demonstrated the excellent quality of the wood for the plywood industry. As a result, ucuuba grew more important to the wood industry and is up to this day one of the most exported wood species of the Amazon Estuary. The cutting of ucuuba trees is common practice in the visited regions, unlike the collection of fruits, which is an activity that was performed by previous generations.

Ucuuba is a species considered as typically Amazonian and grows in floodplain and flooded forests. The species prevails in flooded areas on the banks of rivers, streams and holes, and areas that might be affected by the floods. The Myristicaceae family is distributed across the Neotropics. The Amazon basin concentrates in its central-western portion the most part of the species, which would lead one to believe that this area would be the center of origin and dispersion of the family in the American continent. Among the species of the Myristicaceae family, the *Virola* genus is the one with the widest geographic distribution.

Moreover, said species has a great economic potential, since its wood is used in the manufacture of laminates, plywood, packages, sport articles, toys, pencils, sticks, spools and bobbins, among other utensils. Due to predatory exploitation, some populations have been extinguished, and some have entered in the list of endangered species of IBAMA/1992 (Brazilian Institute for the Environment and Renewable Natural Resources). According to some researchers, the species *Virola surinamensis* is not in the IBAMA list of endangered species which was not yet been approved. This fact is mainly due to the evidence of large populations of the species in the Amazon estuary.

Additionally, ucuuba (*Virola surinamensis*) is a medium-sized species (up to 40 m height and DBH<1.0 m), monopodial bole and cuneiform crown. Its branches have green glabrous, alternate leaves with obtuse base and acuminated apex. The inflorescence is in form of axillary or sub-axillary panicles, with laterally opposed pedicels; it has fascicles of 8 to 15 flowers possess at the ends of the branches; rare female flowers having the ovary in ovoid form and short stylus; stigma is emarginate, bifidus and erect. The fruit is elliptic and 14 to 16 mm long. The trunk has regular, verticillate, nearly horizontal branches; the bark is thick, whitish and brown on the inside.

The seed is recalcitrant, having a primary endozoochoric/barochoric dispersion and a secondary hydrochoric dispersion. The temperature of 20 to 30° C. and the paper towel substrate were the best treatments for the germination of *Virola surinamensis*. The *Virola* wood is light, having a density around 0.50 g/cm$^3$; its core varies from light beige to dark brown; its sapwood is well developed, tasteless and has a distinct smell.

The ucuuba butter is basically composed of triglycerides that are extracted from the almond which contains short chain fatty acids (Lauric and Myristic).

The myristic acid is a saturated fatty acid with the molecular formula $CH_3(CH_2)_{12}COOH$. The myristic acid in general has emollient and humectant properties, thus protecting the skin from the irritating effects of soaps and detergents.

Prior-art document WO2009139884 provides a composition comprising reaction products from a reaction of a natural butter or natural oil such as shea butter (or shea lard) with glycerin in the presence of a basic catalyst and wherein the reaction products retain the unsaponifiable portion of said natural butter or natural oil. The resulting reaction products are self-emulsifiable and are particularly useful in personal care, cosmetic, pharmaceutical, paper and textile applications. In particular, WO2009139884 discloses a composition comprising reaction products derived from the reaction of butter or vegetable oils with ucuuba butter. Said document defines that the butter or vegetable oil is composed of a large group of species, among them, ucuuba. However, said document does not disclose or suggest the high moisturizing power of ucuuba.

Prior-art document WO2005117849 provides a strategy that combines an enzyme inhibition assay with a chemical dereplication process to identify active plant extracts and the particular diarylalkanes and/or diarylalkanols compounds within those extracts that specifically inhibit binuclear enzyme function. Included in the present invention are compositions of matter comprised of one or more of diarylalkanes and/or diarylalkanols, which inhibit the activity of binuclear enzymes, particularly tyrosinase and which prevent melanin overproduction. The present invention also provides a method for inhibiting the activity of a binuclear enzyme, particularly tyrosinase and a method for preventing and treating diseases and conditions related to binuclear enzyme function. Sais document further discloses a method for preventing and treating melanin overproduction and diseases and conditions of the skin related thereto. In particular, the method for preventing and treating diseases and conditions related to binuclear enzyme function and melanin overproduction is comprised of administering to a host in need thereof an effective amount of a composition comprising one or more diarylalkanes and/or diarylalkanols synthesized and/or isolated from one or more plants together with a pharmaceutically acceptable carrier. In particular, WO 2005117849 discloses chemical compounds (diarylalkanes) extracted from *Virola* species of family Myristicaceae, but, besides having a distinct objective and being related to a field of technology other than cosmetics, said document also does not disclose or suggest the high moisturizing power of ucuuba.

Document US 2006210505 relates to multi-phase personal care compositions comprising a first phase and a second phase, wherein said first and second phases form a visually distinct pattern. The compositions are intended for moisturizing or conditioning skin or hair and comprise less than about 10%, by weight of the multi-phase personal care composition, of surfactant. Although ucuuba butter is cited among the examples of waxes that may be added to said compositions, there is no information associating a different moisturizing effect to the high concentration, preferably above 70%, of myristic acid in said butter.

Patent FR2934495, owned by the Applicant, relates to cosmetic compositions comprising ucuuba (*Virola surinamensis*) butter capable of providing a matte effect, that is, eliminating or reducing the skin shine and/or oiliness. This prior-art document, despite disclosing the use of ucuuba butter in cosmetics, does not deal with the moisturizing function, much less any effect associated with the high concentration, preferably above 70% of myristic acid in the butter.

A dry and dehydrated skin loses its biomechanic, biological and especially aesthetic properties because their appearance becomes dull, rough, inelastic and prone to flaking. A dry and dehydrated skin requires care, since its integrity may be compromised if not properly hydrated.

For this reason, there is a need and demand for products and cosmetic formulations with high moisturizing power, mainly providing long-lasting effect. Thus, the main purpose of the present invention is to provide cosmetic formulations with high moisturizing power and products containing such formulations.

SUMMARY OF THE INVENTION

The present invention relates to highly moisturizing cosmetic formulations, with effect of dry and powdery touch, comprising ucuuba (*Virola surinamensis*) butter, which contains a high concentration of myristic acid, more particularly in a concentration equal to or above 70% of the composition of said butter. Said formulations present long-lasting hydration of at least 8 hours.

Moreover, the present invention relates to cosmetic products comprising such formulations, as well as to the use of said ucuuba butter containing myristic acid in high concentration to prepare a cosmetic product/cosmetic formulations for skin long-lasting hydration providing effect of dry and powdery touch.

Also, the present invention discloses a cosmetic kit comprising the disclosed formulation together with a suitable applicator and instructions for use.

BRIEF DESCRIPTION OF THE FIGURES

FIG. 6 describe the mean hydration of the product of the invention by time and treatment and of the control.

FIG. 7 discloses the hydration percentages according to time.

DETAILED DESCRIPTION OF THE INVENTION

Figure 1:
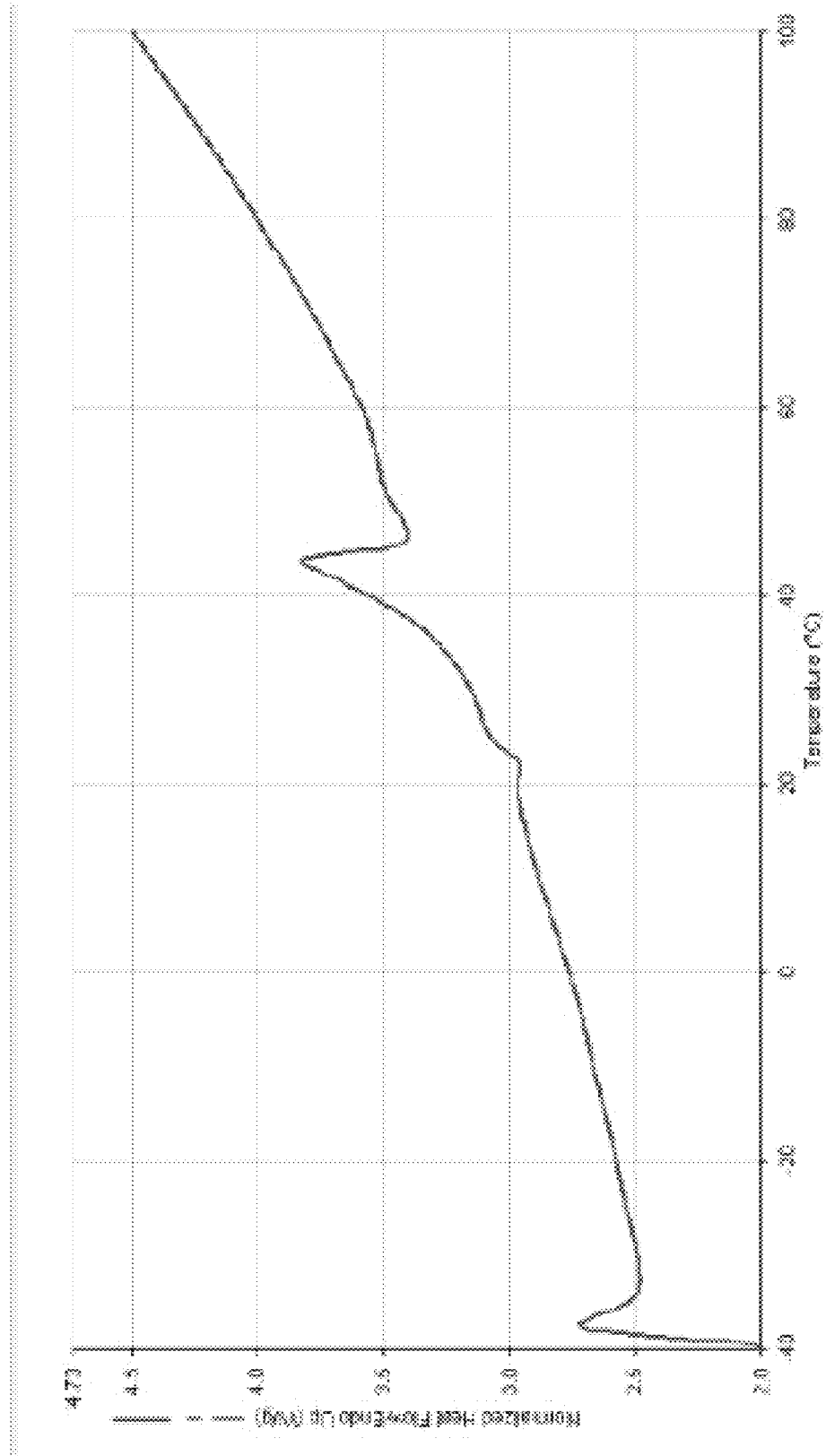
FIG. 1 describes the melting curve of the ucuuba butter.

The present invention relates to highly moisturizing cosmetic formulations, with effect of dry and powdery touch, comprising, as active ingredient, ucuuba (*Virola surinamensis*) butter, which contains myristic acid in high concentration, more particularly in a concentration equal to or above 70% of the composition of said butter.

The concentration of ucuuba (*Virola surinamensis*) butter in the cosmetic formulation varies from 1 to 5% by weight of the total formulation.

It was found that specific formulations comprising ucuuba butter with a high concentration of myristic acid of equal to or above 70% by weight of the total composition provide improved results with respect to hydration. That is, the herein disclosed formulations are highly moisturizing for the skin, besides providing effect of dry and powdery touch.

The process of producing ucuuba butter is simple and provides high yield (22 to 27%). The butter is stable and has a differentiated sensory profile for cosmetic application.

Although the process for obtaining ucuuba butter is not determinant for the purposes of the present invention, in a preferred preparation embodiment, the fruits are collected wet with red pulp and freshly fallen off the ground. The fruits are dried in a forced air circulation oven at 60 to 70° C. prior to pressing. Separated and dried kernels may be used as an alternative and heated at 80 to 100° C. prior to initiate pressing, so that the butter can be more easily released, and the press must be pre-heated with steam in order to avoid the butter's hardening at the beginning of the process.

Since the ucuuba butter has a mild and pleasant smell, good quality and high amount of unsaponifiables that can bring an additional benefit to the butter, it is possible to conduct only one process of clarification to make it suitable for use in the final formulation.

Preferably, the oil obtained from pressing is mixed with bleaching earth and the system is kept under vacuum. After a sufficient contact time of the oil/earth mixture, the mixture is filtered to remove the bleaching earth and other solid impurities. In general, the main stages on processing ucuuba fruits are:

a) selecting the fruits according to their maturation point (mature);

b) drying the fruits through sun exposure and manual removal of the seeds containing the pulp;

c) drying the seeds through sun exposure or in an oven with forced air circulation;

d) cooking the seeds at 80 to 100° C. in a stove to make it easy to release the butter, which has a high melting point;

e) physically pressing the seeds;

f) filtering the butter by adding a filtering agent;

g) treating the butter with organic acid and acidly activated clay for a certain period of time under vigorous stirring;

h) clarifying the butter for a certain period of time under vacuum at a given temperature;

i) vacuum filtration at a given temperature; and j) adding a cleaner and an antioxidant in an amount sufficient to obtain the final ucuuba butter.

The ucuuba butter is basically composed of triglycerides that are extracted from almond, which contains short chain fatty acids (lauric and myristic).

There were made 3 batches with the ucuuba butter produced with different types of starting materials (fruits), wherein the results showed that the obtained butter has excellent quality, as well as high stability.

1) Physicochemical Results of the Produced Batches

TABLE A

| Physicalchemical | 1st batch pilot With pulp | 2nd batch pilot Without pulp, germinating/non-germinating mixture | 3rd batch industrial Dry seeds with pulp |
|---|---|---|---|
| Aspect | solid | solid | solid |
| Color | orange | orange | orange |
| Smell | characteristic | characteristic | characteristic |
| I. Saponification (mgKOH/g) | 231.0 | 234.0 | 230.0 |
| I. Iodine (g I$_2$/100 g) | 8.0 | 4.4 | 7.7 |
| Free Fatty Acids (oleic %) | 0.5 | 5.0 | 7.2 |
| I. Peroxides (meq/Kg) | 4.3 | 1.2 | 5.2 |
| Fatty Composition | | | |
| C8:0 (caprylic) | 0.09 | 0.2 | 0.16 |
| C10:0 (capric) | 0.61 | 0.6 | 0.68 |
| C12:0 (lauric) | 14.03 | 14.6 | 14.7 |
| C14:0 (myristic) | 70.06 | 75.2 | 69.46 |
| C16:0 (palmitic) | 6.0 | 4.2 | 5.93 |
| C16:1 palmitoleic) | 0.4 | 0.3 | 0.42 |
| C18:0 (stearic) | 0.8 | 0.7 | 0.89 |
| C18:1 (oleic) | 7.1 | 3.5 | 6.57 |
| C18:2 (linoleic) | 0.5 | 0.5 | 0.58 |

2) Triacylglycerol Composition of Ucuuba Butter

TABLE B

| Triglyceride | | |
|---|---|---|
| C36:0 | CCP | 0.29 |
| | LaLaLa | 0.44 |
| C38:0 | LaLaM | 4.60 |
| C40:0 | LaMM | 35.89 |
| | CMP | 0.10 |
| C42:0 | MMM | 42.50 |
| | LaMP | 1.84 |
| C44:0 | MMP | 5.62 |
| | LaPP | 2.16 |
| | LaMS | 0.45 |
| C44:1 | LaMO | 0.16 |
| C46:0 | MMS | 0.78 |
| C46:1 | MMO | 2.73 |
| | LaPO | 0.54 |
| C48:1 | MPO | 1.29 |
| C50:2 | MOO | 0.61 |

Fatty acid symbols:
C—capric;
L—lauric;
M—myristic;
P—palmitic;
S—stearic;
O—oleic 3) Unsaponifiables 3.1.) Unsaponifiables

TABLE C

| Analysis | Sample 2 | Sample 1 |
|---|---|---|
| Unsaponifiable matter (%) | 3.0 | 2.7 |

3.2.) Content of Tocopherols (mg/100 g)

TABLE D

| Tocopherols and Tocotrienols | Sample 2 | Sample 1 |
|---|---|---|
| α-tocotrienol | 63.75 | 57.78 |

3.3.) Content of Phytosterols (mg/kg)

TABLE E

| Determination | Sample 2 | Sample 11 |
|---|---|---|
| Cholesterol (%) | 0.47 | 0.31 |
| Campesterol (%) | 10.36 | 10.18 |
| Campestanol (%) | 0.90 | 0.84 |
| Stigmasterol (%) | 8.82 | 8.39 |
| Clerosterol (%) | 2.34 | 2.38 |
| β-Sitosterol (%) | 67.63 | 66.88 |
| δ-5-avenasterol (%) | 8.62 | 9.97 |
| δ-5-24 stigmastadienol (%) | 0.28 | 0.55 |
| δ-7-stigmastenol (%) | 0.28 | 0.42 |
| δ-7-avenasterol (%) | 0.01 | 0.09 |
| Others (%) | 4.13 | 2.99 |
| β-Sitosterol + others (*) | 79.16 | 79.78 |
| Total Sterols (mg/Kg sample) | 1273 | 1384 |

(*) δ-5-avenaterol + δ-5-23-stigmastadienol + cholesterol + sitostanol + δ-5-24 stigmastadienol Ucuuba butter contains a high content of unsaponifiables (approximately 3%), wherein approximately 0.06% from said amount is alpha-tocotrienol and 0.1% phytosterols, mainly beta-sitosterol.

4) DSC Results

FIG. 1 describes the melting curve of the Ucuuba butter.

Based on the melting curve it is possible to obtain the melting range of the material, as well as the temperature at which maximum melting occurs.

Melting range: 29 to 48° C.

Melting temperature: 44

TABLE F

| Sample | T (° C.)(initial) | T (° C.)(final) | T (° C.)(peak) |
|---|---|---|---|
| Candelilla | 58.0 | 69.0 | 66.7 |
|  | 69.0 | 76.0 | 73.0 |
| Bee | 33.2 | 68.4 | 52.0 |
| Carnauba | 66.0 | 90.2 | 84.4 |
| Ucuuba | 28.6 | 48.2 | 43.7 |
| Mucaja | 4.8 | 28.6 | 22.3 |
|  | 46.0 | 60.0 | 50.3 |
| Inaja | 14.4 | 32.0 | 27.0 |
| Tucuma | 15.4 | 35.0 | 31.4 |
|  | 94.0 | 97.4 | 95.1 |
| Sapucainha | 13.5 | 31.0 | 23.7 |

Several butter and wax samples have been evaluated using the DSC technique and, based on the results obtained, the ucuuba butter has the closest melting range to bee wax, which is very interesting for use in cosmetics.

5) Specifications of the Butter

TABLE G

| Control characteristic | Control method | Analysis | Unity | Min | Max |
|---|---|---|---|---|---|
| MP1 | MA-465 | Appearance | NA | solid appearance | |
| MP2 | MA-124 | Color | NA | yellow | |
| MP1020 | MA-308 | Color (objective) lovibond scale | NA | — | |
| MP3 | Ma-056 | Smell | NA | standard | |
| MP649 | MA-071 | Free fatty acids | % | 0.0 | 10.0 |
| MP679 | MA-741 | Saponification index | Meq/ KOH/g | 225.0 | 238.0 |
| MP667 | MA-742 | Iodine index* | % | 3.0 | 11.0 |
| MP677 | MA-073 | Peroxide index | MeqO2/kg | 0.0 | 10.0 |
| MP31 | M31 | humidity | % | 0.0 | 0.5 |

*2 deviations were taken into account for the specification range for the iodine index, and not 3 deviations, according to IT-352.

6) Allergenicity

According to the methodology used to evaluate the potential of skin irritability, sensibilization, photoallergy and phototoxicity of the product, it could be concluded that said product did not induce any skin irritation or sensibilization process and did not cause allergy nor phototoxicity during the period of study, thereby being considered approved for topic use.

TABLE H

| Name | Concentration (*) | Known skin properties (*) |
|---|---|---|
| C8:0 (caprylic) | 0.09-0.16 | Corrosive |
| C10:0 (capric) | 0.61-0.63 | Irritating |
| C12:0 (lauric) | 14.03-14.56 | Non-irritating to the skin, irritating to the eyes |
| C14 (myristic) | 70.06-75.24 | Non-irritating to skin or eyes |
| C16:o (palmitic) | 4.17-6.0 | Non-irritating to skin or eyes |
| C18:0 (stearic) | 0.66-0.80 | Non-irritating to skin or eyes |
| C18:1 (oleic) | 3.49-7.10 | Non-irritating to skin or eyes |

(*) Unichema International - Fatty Acid Data Book 3rd ed, 1992.

Moreover, the ucuuba (*Virola surinamensis*) butter containing a high concentration of mysristic acid, more particularly in a concentration equal or greater than 70% of the composition of said butter, is used for the preparation of a distinctive cosmetic product with high skin moisturizing effect.

A cosmetic kit of the present invention comprises the disclosed formulation together with a suitable applicator and instructions for use.

Moreover, cosmetically acceptable adjuvants, directed to the application in the cosmetics, hygiene and personal care industry, may also be used.

Examples of adjuvants which may be used in the formulations of the present invention include, but not limited to, aqua, vegetable oils (such as *Elaeis guineensis* oil), sodium salts (such as sodium chloride, sodium hydroxide, sodium carbonate, sodium trideceth sulfate, sodium lauroamphoacetate), magnesium salts (such as magnesium chloride and magnesium nitrate), cocamide MEA, parfums, xanthan gum, cocamidopropyl betaine, citric acid, disodium EDTA, tetrasodium EDTA, DMDM hydantoin, BHT, TBHQ, methylchloroisothiazolinone, methylisothiazolinone, glycerin, isoamyl cocoate, cetearyl alcohol, glycol distearate, cyclopentasiloxane, phenoxyethanol, aluminum starch octenylsuccinate, glyceryl stearate, PEG-100 stearate, caprylic/capric triglyceride, ammonium acryloyldimethyltaurate/VP copolymer, acrylate polymers (such as acrylates/C10-30 alkyl acrylate crosspolymer), polyglyceryl-3 caprylate, trilaureth-4 phosphate, polyglyceryl-2 sesquiisostearate, hexyl cinnamal, limonene, benzyl salicylate, butylphenyl methylpropional, hydroxycitronellal, citronellol, alpha-isomethyl ionone, coumarin, linalool, benzyl alcohol, citral, sodium (*Astrocaryum vulgare*/*Euterpe oleraceae*/palm) fruit/(*Astrocaryum vulgare*/palm) kernel/(*Astrocaryum murumuru*/babassu/*Bertholletia excelsa*/*Carapa guianensis*/cocoa/*Fevillea trilobata*/*Passiflora edulis*/*Theobroma grandiflorum*) seedate, *Zea mays* starch, sucrose, sorbitol, decyl glucoside, lecithin, etidronic acid, alumina, cosmetically acceptable dyes and pigments, such as CI 19140, CI 77891, CI 77492, CI 77491, CI 14700, CI 77499.

Preferably, the invention refers to compositions comprising the following constitutions:

TABLE I

| Component | Concentration (% by weight) | Function |
|---|---|---|
| Ucuuba butter | 1 to 5% based on the formulation | Active ingredient |
| Myristic acid contained in the ucuuba butter | 70 to 100% based on the total weight of the butter | |
| Cosmetically acceptable adjuvants | qs. | Carrier |

The cosmetic formulation of the present inventions discloses a series of advantages and characteristics desired in a cosmetic product, especially high moisturizing effect, in particular for hands and body, face and hair, advantages which are achieved through the optimal and balanced combination of its components.

Non-exhaustively, the cosmetic formulations of the present invention may be advantageously used for the preparation of cosmetic products in the form of bar soaps, liquid soaps, butters, creams, elixirs, body moisturizers, hand moisturizers, moisturizing bars, emulsions for hand, body, face and hair.

The embodiments of the present invention exemplified below intend to illustrate it, not limiting, in any way, the scope of its subject matter.

EXAMPLES

Table J below shows a cosmetic formulation according to the present invention:

TABLE J

| Component | Concentration (% by weight) | Function |
|---|---|---|
| Ucuuba butter | 1.0% based on the formulation | Active ingredient |
| Myristic acid contained in the ucuuba butter | 70 to 100% | |
| Cosmetically acceptable adjuvants | qs. | Carrier |

Table K below shows a cosmetic formulation according to the present invention:

TABLE K

| Component | Concentration (% by weight) | Function |
|---|---|---|
| Ucuuba butter | 2.5% based on the formulation | Active ingredient |
| Myristic acid contained in the ucuuba butter | 70 to 100% | |
| Cosmetically acceptable adjuvants | qs. | Carrier |

Table L below shows a cosmetic formulation according to the present invention:

TABLE L

| Component | Concentration (% by weight) | Function |
|---|---|---|
| Ucuuba butter | 5.0% based on the formulation | Active ingredient |
| Myristic acid contained in the ucuuba butter | 70 to 100 | |
| Cosmetically acceptable adjuvants | qs. | Carrier |

Said cosmetic formulation is prepared in a manner that is conventional and known to the person skilled in the art.

Tests:

The cosmetic formulation cited and defined in the example above is the composition applied in the tests described below.

In turn, the parameter used as "control" for comparison with the formulations of the present invention is an area of the skin without any product applied on it.

The expression "phototype" used in the following tests is a Fitzpatrick classification based on the reaction to sunburn in six types of skin:

Phototype I: White skin, very sensitive to the sun. The skin burns very easily, never tans;

Phototype II. White skin, sensitive to the sun. The skin burns easily, tans minimally;

Phototype III. Light brown skin that has normal sensibility to the sun. The skin burns and tans moderately;

Phototype IV. Brown skin, whose sensibility to the sun is easily normal. The skin burns minimally, but tans moderately;

Phototype V: Dark brown skin, less sensitive to the sun. The skin rarely burns and tans very easily;

Phototype VI. Black skin, not sensitive to the sun. Never burns and is deeply pigmented.

Test 1—Assessment of the Skin Hydration by Corneometry after Rinsing the Product Applied at the Concentration of 1.0% Ucuuba 1. Objective To assess skin hydration level after application of the formulation disclosed in Table J above.

2. Panel of Volunteers

The female participating volunteers were instructed to suspend the use of any topic products in the region of the forearms 48 hours prior to the start of the study. The female participating volunteers remained in the laboratory for measurements after 15 minutes, 2, 4, 8 and 24 hours. Prior to the first measurement, after application, the product containing the formulation of Table J was rinsed under running water for 30 seconds. After the measurement of 8 hours, the research participants returned home and were advised not to wet or wash the arms. In the following day, they returned to the laboratory for the measurement of 24 hours after application of the product.

3. Evaluation Procedure 3.1. Overview

On the left or on the right volar forearm of the research participant were marked two areas measuring 2.5×4.0 cm, called sites. The determination of the control site (without application of any products) and of the product application site was random between the marked sites, as recorded in the correlation spreadsheet on Table 1 below.

TABLE 1

| Research participant number | Age | Photo-type | Application sites | | |
|---|---|---|---|---|---|
| | | | Site 1 | Site 2 | Site 3 |
| 01 | 45 | III | Control | | Product: 1.0% concentration of ucuuba butter |
| 02 | 22 | IV | Product: 1.0% concentration of ucuuba butter | Control | |
| 03 | 35 | III | | Product: 1.0% concentration of ucuuba butter | Control |
| 04 | 57 | III | Control | | Product: 1.0% concentration of ucuuba butter |
| 05 | 60 | III | Product: 1.0% concentration of ucuuba butter | Control | |
| 06 | 43 | IV | | Product: 1.0% concentration of ucuuba butter | Control |
| 07 | 56 | III | Control | | Product: 1.0% concentration of ucuuba butter |
| 08 | 55 | III | Product: 1.0% concentration of ucuuba butter | Control | |

TABLE 1-continued

| Research participant number | Age | Photo-type | Application sites Site 1 | Site 2 | Site 3 |
|---|---|---|---|---|---|
| 09 | 48 | III | | Product: 1.0% concentration of ucuuba butter | Control |
| 10 | 53 | IV | Control | | Product: 1.0% concentration of ucuuba butter |
| 11 | 30 | III | Product: 1.0% concentration of ucuuba butter | Control | |
| 12 | 57 | III | | Product: 1.0% concentration of ucuuba butter | Control |
| 13 | 50 | III | Control | | Product: 1.0% concentration of ucuuba butter |
| 14 | 60 | III | Product: 1.0% concentration of ucuuba butter | Control | |
| 15 | 48 | III | | Product: 1.0% concentration of ucuuba butter | Control |
| 16 | 44 | III | Control | | Product: 1.0% concentration of ucuuba butter |
| 17 | 41 | IV | Product: 1.0% concentration of ucuuba butter | Control | |
| 18 | 44 | III | | Product: 1.0% concentration of ucuuba butter | Control |
| 19 | 54 | III | Control | | Product: 1.0% concentration of ucuuba butter |
| 20 | 48 | III | Product: 1.0% concentration of ucuuba butter | Control | |

After 30 minutes of acclimatization in a controlled environment at 20±2° C. and 50±5% relative air humidity, the baseline measurements (prior to product application) of skin capacitance in the marked sites were obtained. Then 20 μL of the product were applied, rubbing it homogeneously over the site with the help of a disposable finger cot.

After application, the survey participants remained in the laboratory so that the capacitance measurements could be done after 15 minutes, 2, 4, 8 and 24 hours. After the measurement of 8 hours, the research participants returned home, being advised not to wet or wash the arms. In the following day, they returned to the laboratory so that the measurement after 24 hours from the sample application could be done.

During the entire experiment in the laboratory, the climate conditions were maintained constant according to the above-mentioned ranges.

3.2. Product Application and Rinsing

Prior to product application, the site was moistened in running water for 10 seconds. Then, 20 μL of the product were applied, rubbing it homogeneously over the site with the help of a disposable finger cot for 1 minute.

After that, the site was rinsed under running water for 30 seconds. Then, the back part of the forearm and the surroundings of the site were dried with a paper towel, without passing it over the washed spot.

The same rinsing procedure was made in the control site, however, without any product application.

3.3. Obtaining Capacitance Measurements

Capacitance measurements were obtained with a Corneometer® 825 probe coupled to Multi Probe Adapter, MPA 5 (CKeletronics, Germany).

Concomitantly, an automated Microsoft® Office Excel 2010 sheet was utilized to calculate the Coefficient of Variation (CV) of the readings taken. A minimum of 5 and maximum of 10 measurements were taken per site at each assessment time. If in 5 measurements CV value was lower than 6%, measurements on the site were ceased. If not, measurements kept on being taken till a CV value lower than 6% was obtained, considering a maximum of 10 measurements. Ten measurements taken and CV<6% not reached, the 10% value is to be considered the new limit; readings on the site are ceased or the process is started all over again if the value is over 10%.

4. Data Analysis and Interpretation 4.1. Software for Obtaining Average Values and Data Analysis:

MPA for Windows® NT/XP (CKeletronic, Germany, 2004).

Microsoft® Office Excel 2010 (Microsoft Corp., USA, 2010).

4.2. Software for Statistical Analysis:

GraphPad™ Prism® 5.00 (GraphPad Software, San Diego, Calif. USA, www.graphpad.com).

4.3. Interpreting the Results

The skin hydration provided by the application of a moisturizing product is evidenced by the increase in the capacitance value generated in the capacitor formed between the Corneometer® probe base and the skin. The greater the capacitance value, the greater the amount of water of the skin and, therefore, the greater the hydration level.

4.3.1. Calculations

From the capacitance values (h) the skin hydration difference ($\Delta h$) was calculated, i.e., the variation among the capacitance measurements taken at each assessment time in relation to the basal measurements. The $\Delta h$ parameter was calculated for product and control, as per Equation 1.

$$\Delta h = h_{ti} - h_{t0}$$

Equation 1. Skin hydration difference at each assessment time in relation to the basal measurements. Where: $\Delta h$=skin hydration difference, $h_{ti}$=mean capacitance measurements obtained after i hours of study (i=15 minutes, 2, 4, 8 and 24 hours); $h_{t0}$=mean capacitance measurements obtained in the beginning of the study (basal).

From the hydration difference values (Δh), the hydration parameters (H) and the skin hydration percentage (% H) provided by the product were calculated, as per Equations 2 and 3.

$$Hti = \Delta hti(\text{product}) - \Delta hti(\text{control})$$

Equation 2. Calculation of the skin hydration provided by the application of the product. Where: $H_{ti}$=skin hydration after i hours of the application of the product; $\Delta h_{ti}$ (control) and $\Delta h_{ti}$ (product)=skin hydration differences obtained for control and product, respectively.

$$\% Hti = (Hti \times 100)/ht0$$

Equation 3. Calculation of the skin hydration percentage provided by the application of the product. Where:

% $H_{ti}$=hydration percentage value, $H_{ti}$=skin hydration provided by the application of the product after i hours of the application; $h_{t0}$=mean capacitance measurements obtained in the beginning of the study (basal).

4.3.2. Statistical Evaluations
4.3.2.1. Basal Homogeneity

The homogeneity of the basal data, necessary to evince that the final results were not influenced by the initial condition, was assessed by applying the paired, bimodal Student's t-Test method, in which a 95% confidence interval was considered, to the basal capacitance values ($h_{t0}$) obtained for product and control. Satisfactory results are achieved when there is no statistically significant difference (P>0.05) between the initial capacitance measurements obtained from the areas where product and control were assessed.

4.3.2.2. Significance of the Effect

The significance of the variation in skin hydration at each assessment time, both for control and product, is assessed by employing the paired, bimodal Student's t-Test method, in which a 95% confidence interval was considered, to the basal capacitance values (ht0) in relation to the values obtained after i hours of the application (hti); i=15 minutes, 2, 4, 8 and 24 hours.

Satisfactory results are achieved when, concerning control, there is no statistically significant difference between ht0 and hti (P>0.05) and, concerning product, hti is significantly superior to ht0 (P<0.05), evincing an increase in skin hydration.

4.3.2.3. Comparison Between Product and Control

The evaluation of the significance of the increase in skin hydration due to the use of the product, in relation to control, was carried out by employing the paired, bimodal Student's t-Test method, in which a 95% confidence interval was considered, to the calculated skin hydration difference values at each assessment time, for product and control (Δhti, P vs. Δhti, C).

The adequate results are achieved when the Δh values for product are significantly higher than the ones obtained for control (P<0.05).

5. Results and Discussions:
5.1. Statistics on the Participation of Volunteers

Total contacted volunteers: 110;
Total of participant volunteers: 34;
Total absences on the day of the study: 14;
Total volunteers dismissed after evaluation of inclusion and exclusion criteria: 0;
Effectively included volunteers: 20;
Volunteers who completed the study: 20.

5.2. General Data on the Study Group

Average age: 48±10 years.
Phototype (Fitzpatrick): 80% phototype III and 20% phototype IV.

5.3. Climate Control

Statistical data on the environmental monitoring throughout the days the study was carried out at the waiting and climatization room of the volunteers:

Day 1
Temperature: (21.2±0.5° C. (95% Confidence interval: 21.0° C. to 21.4° C.)
Relative air humidity: (49±2) % (95% Confidence interval: 48% to 50%)

Day 2
Temperature: (21.2±0.5° C. (95% Confidence interval: 21.0° C. to 21.4° C.)
Relative air humidity: (49±2) % (95% Confidence interval: 48% to 50%)

Day 3
Temperature: (21.0±0.5° C. (95% Confidence interval: 20.7° C. to 21.3° C.)
Relative air humidity: (50±2) % (95% Confidence interval: 48% to 51%)

According to the registered climate control data, temperature and humidity in the waiting and climatization room of the volunteers remained within the range established in the study protocol.

5.4. Results Obtained from the Evaluation

Skin hydration was assessed with capacitance measurements. Tables 2 to 2.5 display all the measurements taken.

Tables 2 to 2.5 display the measured capacitance values for product at a concentration of 1.0% of ucuuba butter.

TABLE 2

| Basal | | | | | | | | | | | | | | |
|---|---|---|---|---|---|---|---|---|---|---|---|---|---|---|
| Participant 01 | | | Participant 02 | | | Participant 03 | | | Participant 04 | | | Participant 05 | | |
| S1 | S2 | S3 | S1 | S2 | S3 | S1 | S2 | S3 | S1 | S2 | S3 | S1 | S2 | S3 |
| 46.4 | | 44.0 | 31.6 | 34.7 | | | 35.3 | 31.4 | 44.9 | | 37.1 | 33.6 | 32.9 | |
| 43.2 | | 46.6 | 32.3 | 34.5 | | | 34.1 | 35.9 | 46.9 | | 41.0 | 36.7 | 33.3 | |
| 44.3 | | 43.1 | 30.9 | 35.8 | | | 37.4 | 33.5 | 43.4 | | 39.5 | 34.5 | 32.6 | |
| 43.1 | | 47.8 | 34.5 | 36.9 | | | 38.3 | 31.8 | 46.4 | | 37.5 | 31.6 | 34.6 | |
| 47.9 | | 41.9 | 31.5 | 37.5 | | | 34.3 | 32.6 | 43.1 | | 41.4 | 32.9 | 35.1 | |
| Participant 06 | | | Participant 07 | | | Participant 08 | | | Participant 09 | | | Participant 10 | | |
| S1 | S2 | S3 | S1 | S2 | S3 | S1 | S2 | S3 | S1 | S2 | S3 | S1 | S2 | S3 |
| | 41.2 | 43.6 | 36.4 | | 41.9 | 32.9 | 33.7 | | | 35.7 | 31.8 | 34.8 | | 39.7 |
| | 45.3 | 41.3 | 36.6 | | 40.0 | 35.4 | 34.3 | | | 34.0 | 34.3 | 34.5 | | 38.2 |
| | 43.0 | 41.7 | 37.4 | | 42.6 | 34.0 | 33.1 | | | 37.2 | 32.5 | 36.6 | | 41.4 |

TABLE 2-continued

Basal

| Participant 06 | | | Participant 07 | | | Participant 08 | | | Participant 09 | | | Participant 10 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
|  | 42.4 | 43.5 | 39.0 |  | 45.6 | 33.8 | 34.4 |  |  | 35.9 | 32.9 | 36.4 |  | 40.1 |
|  | 42.9 | 44.4 | 39.7 |  | 45.3 | 32.7 | 33.8 |  |  | 36.5 | 32.3 | 36.7 |  | 41.9 |

| Participant 11 | | | Participant 12 | | | Participant 13 | | | Participant 14 | | | Participant 15 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 39.6 | 33.1 |  |  | 42.3 | 39.7 | 31.4 |  | 38.6 | 32.5 | 31.0 |  |  | 41.2 | 44.0 |
| 43.9 | 36.1 |  |  | 41.8 | 41.4 | 33.0 |  | 41.8 | 31.8 | 31.9 |  |  | 42.9 | 43.2 |
| 39.2 | 36.8 |  |  | 41.5 | 40.4 | 32.6 |  | 37.1 | 30.1 | 33.2 |  |  | 41.9 | 43.7 |
| 38.8 | 34.2 |  |  | 43.8 | 43.4 | 32.8 |  | 40.5 | 30.2 | 31.2 |  |  | 45.6 | 42.1 |
| 38.4 | 37.0 |  |  | 44.6 | 40.0 | 35.6 |  | 39.4 | 29.1 | 33.7 |  |  | 42.5 | 44.8 |

| Participant 16 | | | Participant 17 | | | Participant 18 | | | Participant 19 | | | Participant 20 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 27.1 |  | 25.4 | 39.7 | 40.4 |  |  | 35.3 | 42.2 | 40.2 |  | 42.1 | 42.2 | 37.5 |  |
| 26.0 |  | 25.2 | 41.3 | 43.6 |  |  | 34.8 | 37.8 | 45.0 |  | 44.0 | 43.3 | 37.9 |  |
| 29.2 |  | 25.7 | 40.9 | 43.4 |  |  | 34.4 | 40.8 | 41.2 |  | 42.9 | 41.4 | 38.5 |  |
| 26.2 |  | 23.3 | 41.4 | 41.4 |  |  | 37.7 | 43.3 | 44.9 |  | 45.6 | 38.6 | 40.0 |  |
| 26.6 |  | 25.2 | 40.0 | 43.2 |  |  | 33.8 | 41.1 | 43.3 |  | 44.8 | 42.6 | 38.7 |  |

TABLE 2.1

15 minutes

| Participant 01 | | | Participant 02 | | | Participant 03 | | | Participant 04 | | | Participant 05 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 45.1 |  | 45.3 | 32.8 | 37.3 |  |  | 34.5 | 33.0 | 43.5 |  | 39.6 | 33.7 | 36.9 |  |
| 46.7 |  | 44.0 | 33.4 | 36.0 |  |  | 33.4 | 32.2 | 45.9 |  | 39.8 | 32.1 | 34.4 |  |
| 45.7 |  | 45.2 | 33.8 | 39.4 |  |  | 36.4 | 34.1 | 42.8 |  | 39.4 | 33.6 | 33.3 |  |
| 47.3 |  | 45.6 | 35.8 | 37.4 |  |  | 34.9 | 32.6 | 44.1 |  | 37.6 | 36.5 | 34.6 |  |
| 48.8 |  | 46.0 | 35.2 | 38.8 |  |  | 34.4 | 34.5 | 45.0 |  | 38.2 | 34.8 | 34.4 |  |

| Participant 06 | | | Participant 07 | | | Participant 08 | | | Participant 09 | | | Participant 10 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
|  | 43.2 | 42.0 | 37.7 |  | 40.6 | 34.6 | 31.8 |  |  | 34.9 | 30.2 | 35.3 |  | 39.3 |
|  | 44.3 | 42.3 | 38.7 |  | 40.2 | 32.7 | 33.9 |  |  | 37.1 | 32.3 | 34.1 |  | 41.6 |
|  | 46.2 | 41.9 | 34.3 |  | 41.5 | 34.4 | 35.0 |  |  | 35.9 | 33.0 | 32.7 |  | 38.9 |
|  | 44.5 | 45.7 | 34.5 |  | 44.7 | 31.1 | 33.3 |  |  | 34.5 | 32.9 | 36.9 |  | 39.4 |
|  | 45.9 | 44.2 | 36.5 |  | 43.2 | 34.0 | 34.4 |  |  | 34.7 | 34.2 | 35.9 |  | 39.0 |

| Participant 11 | | | Participant 12 | | | Participant 13 | | | Participant 14 | | | Participant 15 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 42.2 | 37.3 |  |  | 40.0 | 39.3 | 34.8 |  | 37.2 | 29.5 | 31.8 |  |  | 42.9 | 41.6 |
| 42.6 | 37.7 |  |  | 41.4 | 39.8 | 32.3 |  | 38.1 | 28.4 | 30.1 |  |  | 39.7 | 42.7 |
| 43.3 | 38.2 |  |  | 39.9 | 40.2 | 31.4 |  | 38.8 | 31.6 | 34.2 |  |  | 42.7 | 43.3 |
| 45.3 | 38.7 |  |  | 43.0 | 41.1 | 32.4 |  | 40.8 | 29.9 | 33.7 |  |  | 44.4 | 44.7 |
| 43.6 | 39.9 |  |  | 40.6 | 40.6 | 33.5 |  | 41.7 | 32.9 | 32.1 |  |  | 43.8 | 42.2 |

| Participant 16 | | | Participant 17 | | | Participant 18 | | | Participant 19 | | | Participant 20 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 26.5 |  | 23.6 | 38.3 | 42.0 |  |  | 33.5 | 41.8 | 41.5 |  | 41.7 | 40.3 | 40.2 |  |
| 25.8 |  | 25.1 | 40.7 | 42.4 |  |  | 36.6 | 39.3 | 43.5 |  | 42.0 | 43.2 | 41.0 |  |
| 26.7 |  | 24.3 | 41.5 | 43.6 |  |  | 32.7 | 38.4 | 43.3 |  | 45.7 | 42.1 | 42.0 |  |
| 26.8 |  | 25.2 | 39.0 | 40.9 |  |  | 36.2 | 40.9 | 42.4 |  | 41.9 | 45.2 | 39.1 |  |
| 27.2 |  | 23.0 | 41.8 | 42.4 |  |  | 33.7 | 40.7 | 42.9 |  | 43.8 | 41.4 | 40.3 |  |

TABLE 2.2

| 2 hours | | | | | | | | | | | | | | |
|---|---|---|---|---|---|---|---|---|---|---|---|---|---|---|
| Participant 01 | | | Participant 02 | | | Participant 03 | | | Participant 04 | | | Participant 05 | | |
| S1 | S2 | S3 | S1 | S2 | S3 | S1 | S2 | S3 | S1 | S2 | S3 | S1 | S2 | S3 |
| 47.2 | | 45.1 | 34.3 | 39.4 | | | 33.5 | 32.9 | 41.8 | | 37.3 | 34.4 | 35.1 | |
| 49.3 | | 44.3 | 35.7 | 39.8 | | | 34.4 | 33.2 | 42.2 | | 39.5 | 34.1 | 37.8 | |
| 48.2 | | 45.6 | 33.5 | 38.2 | | | 34.2 | 31.3 | 44.2 | | 38.2 | 35.5 | 33.3 | |
| 47.3 | | 44.8 | 35.6 | 37.9 | | | 34.5 | 34.3 | 46.3 | | 38.4 | 34.3 | 35.6 | |
| 45.0 | | 45.8 | 36.2 | 37.9 | | | 33.4 | 32.3 | 43.6 | | 37.6 | 35.3 | 35.7 | |
| Participant 06 | | | Participant 07 | | | Participant 08 | | | Participant 09 | | | Participant 10 | | |
| S1 | S2 | S3 | S1 | S2 | S3 | S1 | S2 | S3 | S1 | S2 | S3 | S1 | S2 | S3 |
| | 43.3 | 42.4 | 34.5 | | 41.1 | 31.4 | 33.1 | | | 36.9 | 31.6 | 34.5 | | 37.2 |
| | 44.4 | 41.8 | 37.2 | | 40.1 | 32.6 | 33.5 | | | 35.1 | 32.6 | 32.8 | | 39.0 |
| | 46.6 | 42.3 | 37.9 | | 41.8 | 33.7 | 33.3 | | | 35.3 | 30.3 | 36.0 | | 39.8 |
| | 45.2 | 43.8 | 36.3 | | 42.0 | 34.2 | 34.7 | | | 34.5 | 32.6 | 34.0 | | 39.3 |
| | 45.1 | 43.5 | 35.0 | | 42.7 | 33.3 | 31.1 | | | 33.3 | 31.6 | 37.7 | | 39.0 |
| Participant 11 | | | Participant 12 | | | Participant 13 | | | Participant 14 | | | Participant 15 | | |
| S1 | S2 | S3 | S1 | S2 | S3 | S1 | S2 | S3 | S1 | S2 | S3 | S1 | S2 | S3 |
| 44.4 | 36.0 | | | 43.1 | 38.3 | 31.1 | | 38.0 | 30.8 | 31.3 | | | 43.5 | 42.4 |
| 43.0 | 35.8 | | | 42.8 | 39.0 | 33.7 | | 37.2 | 29.4 | 32.3 | | | 40.0 | 40.5 |
| 44.8 | 35.7 | | | 43.3 | 38.0 | 31.4 | | 38.3 | 29.7 | 33.3 | | | 42.9 | 42.1 |
| 42.2 | 37.2 | | | 44.1 | 40.1 | 31.3 | | 39.2 | 30.6 | 32.1 | | | 40.8 | 40.0 |
| 42.3 | 37.7 | | | 45.6 | 41.2 | 32.6 | | 40.3 | 29.8 | 31.5 | | | 43.9 | 41.5 |
| Participant 16 | | | Participant 17 | | | Participant 18 | | | Participant 19 | | | Participant 20 | | |
| S1 | S2 | S3 | S1 | S2 | S3 | S1 | S2 | S3 | S1 | S2 | S3 | S1 | S2 | S3 |
| 25.5 | | 22.4 | 37.9 | 39.1 | | | 33.2 | 38.8 | 40.5 | | 42.6 | 42.4 | 38.6 | |
| 24.1 | | 25.6 | 38.4 | 43.2 | | | 35.8 | 41.0 | 42.7 | | 40.0 | 41.3 | 38.0 | |
| 25.7 | | 23.4 | 40.4 | 41.0 | | | 34.3 | 42.0 | 42.5 | | 44.7 | 42.1 | 38.4 | |
| 26.8 | | 24.5 | 38.2 | 42.2 | | | 31.3 | 40.8 | 42.3 | | 42.3 | 42.2 | 40.5 | |
| 26.3 | | 24.3 | 41.0 | 43.2 | | | 35.2 | 40.9 | 43.1 | | 42.8 | 42.9 | 39.1 | |

TABLE 2.3

| 4 hours | | | | | | | | | | | | | | |
|---|---|---|---|---|---|---|---|---|---|---|---|---|---|---|
| Participant 01 | | | Participant 02 | | | Participant 03 | | | Participant 04 | | | Participant 05 | | |
| S1 | S2 | S3 | S1 | S2 | S3 | S1 | S2 | S3 | S1 | S2 | S3 | S1 | S2 | S3 |
| 46.1 | | 43.3 | 33.0 | 38.6 | | | 37.7 | 32.7 | 41.5 | | 36.7 | 36.2 | 39.9 | |
| 48.2 | | 44.9 | 34.0 | 37.2 | | | 33.6 | 32.4 | 44.0 | | 38.6 | 36.5 | 39.4 | |
| 45.6 | | 46.5 | 34.3 | 37.8 | | | 35.8 | 32.0 | 44.3 | | 37.4 | 36.6 | 38.3 | |
| 47.8 | | 47.5 | 37.3 | 35.2 | | | 31.3 | 32.4 | 42.6 | | 39.2 | 35.3 | 36.8 | |
| 48.3 | | 45.6 | 35.9 | 37.7 | | | 32.2 | 30.5 | 44.5 | | 38.7 | 37.5 | 39.5 | |
| Participant 06 | | | Participant 07 | | | Participant 08 | | | Participant 09 | | | Participant 10 | | |
| S1 | S2 | S3 | S1 | S2 | S3 | S1 | S2 | S3 | S1 | S2 | S3 | S1 | S2 | S3 |
| | 44.5 | 42.4 | 36.6 | | 42.4 | 32.3 | 33.7 | | | 36.2 | 31.3 | 34.4 | | 39.1 |
| | 43.9 | 43.3 | 35.1 | | 41.8 | 31.9 | 31.4 | | | 33.1 | 32.3 | 35.7 | | 41.5 |
| | 47.6 | 39.9 | 38.1 | | 42.6 | 35.7 | 34.3 | | | 36.9 | 30.8 | 36.9 | | 39.4 |
| | 45.9 | 43.5 | 34.3 | | 40.2 | 33.0 | 33.3 | | | 33.5 | 30.4 | 33.1 | | 40.5 |
| | 46.6 | 42.9 | 38.3 | | 39.3 | 35.4 | 34.3 | | | 34.5 | 33.4 | 33.5 | | 42.3 |
| Participant 11 | | | Participant 12 | | | Participant 13 | | | Participant 14 | | | Participant 15 | | |
| S1 | S2 | S3 | S1 | S2 | S3 | S1 | S2 | S3 | S1 | S2 | S3 | S1 | S2 | S3 |
| 44.0 | 35.6 | | | 42.3 | 39.6 | 32.8 | | 37.0 | 28.5 | 31.7 | | | 41.7 | 41.1 |
| 43.1 | 36.0 | | | 41.8 | 40.3 | 29.9 | | 38.6 | 31.4 | 32.0 | | | 40.9 | 41.5 |
| 44.2 | 37.1 | | | 44.2 | 37.3 | 31.9 | | 37.6 | 29.4 | 32.0 | | | 42.4 | 42.0 |
| 42.8 | 35.7 | | | 41.7 | 40.9 | 33.5 | | 39.8 | 28.4 | 30.1 | | | 43.2 | 41.0 |
| 43.9 | 38.3 | | | 43.3 | 40.7 | 30.6 | | 37.9 | 31.3 | 33.8 | | | 43.8 | 40.6 |

TABLE 2.3-continued

| 4 hours | | | | | | | | | | | | | | |
|---|---|---|---|---|---|---|---|---|---|---|---|---|---|---|
| Participant 16 | | | Participant 17 | | | Participant 18 | | | Participant 19 | | | Participant 20 | | |
| S1 | S2 | S3 | S1 | S2 | S3 | S1 | S2 | S3 | S1 | S2 | S3 | S1 | S2 | S3 |
| 25.4 |  | 23.2 | 39.2 | 40.0 |  |  | 35.4 | 39.9 | 42.0 |  | 41.5 | 40.9 | 40.2 |  |
| 24.1 |  | 25.9 | 39.1 | 39.9 |  |  | 33.7 | 40.0 | 42.8 |  | 43.2 | 40.7 | 38.4 |  |
| 24.8 |  | 22.6 | 39.0 | 43.6 |  |  | 35.1 | 41.2 | 43.1 |  | 42.1 | 42.1 | 39.6 |  |
| 27.0 |  | 24.1 | 37.9 | 43.3 |  |  | 33.4 | 40.4 | 40.5 |  | 40.3 | 42.0 | 39.1 |  |
| 24.9 |  | 24.5 | 40.2 | 41.1 |  |  | 33.6 | 43.6 | 39.0 |  | 42.7 | 42.5 | 39.3 |  |

TABLE 2.4

| 8 hours | | | | | | | | | | | | | | |
|---|---|---|---|---|---|---|---|---|---|---|---|---|---|---|
| Participant 01 | | | Participant 02 | | | Participant 03 | | | Participant 04 | | | Participant 05 | | |
| S1 | S2 | S3 | S1 | S2 | S3 | S1 | S2 | S3 | S1 | S2 | S3 | S1 | S2 | S3 |
| 46.3 |  | 44.4 | 34.8 | 38.1 |  |  | 33.8 | 31.4 | 42.3 |  | 38.3 | 34.6 | 33.6 |  |
| 45.2 |  | 46.5 | 31.9 | 37.0 |  |  | 34.3 | 32.9 | 41.8 |  | 37.8 | 35.0 | 38.2 |  |
| 46.1 |  | 46.3 | 34.0 | 37.4 |  |  | 32.7 | 31.6 | 44.8 |  | 37.5 | 34.2 | 34.3 |  |
| 45.9 |  | 45.5 | 33.8 | 35.4 |  |  | 31.3 | 32.6 | 44.4 |  | 38.0 | 32.1 | 35.4 |  |
| 48.6 |  | 43.7 | 35.6 | 34.2 |  |  | 33.8 | 30.9 | 42.1 |  | 39.3 | 33.3 | 36.6 |  |

| Participant 06 | | | Participant 07 | | | Participant 08 | | | Participant 09 | | | Participant 10 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
|  | 43.3 | 43.2 | 37.8 |  | 39.0 | 32.8 | 33.5 |  |  | 36.2 | 32.0 | 35.5 |  | 39.1 |
|  | 43.7 | 41.4 | 35.3 |  | 39.1 | 33.6 | 34.3 |  |  | 32.0 | 31.0 | 33.4 |  | 42.5 |
|  | 45.1 | 42.1 | 35.4 |  | 40.0 | 33.0 | 31.3 |  |  | 36.0 | 33.0 | 32.7 |  | 42.0 |
|  | 45.2 | 42.1 | 35.5 |  | 40.8 | 33.2 | 34.1 |  |  | 33.8 | 29.2 | 32.1 |  | 37.7 |
|  | 45.7 | 41.6 | 37.1 |  | 42.5 | 34.3 | 33.3 |  |  | 36.3 | 30.5 | 36.2 |  | 39.5 |

| Participant 11 | | | Participant 12 | | | Participant 13 | | | Participant 14 | | | Participant 15 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 42.6 | 36.5 |  |  | 44.7 | 40.7 | 30.8 |  | 40.1 | 30.9 | 30.3 |  |  | 40.8 | 43.7 |
| 41.7 | 35.3 |  |  | 43.8 | 37.5 | 32.6 |  | 38.8 | 30.2 | 32.5 |  |  | 43.9 | 43.2 |
| 42.0 | 36.1 |  |  | 43.6 | 38.3 | 30.7 |  | 36.1 | 28.7 | 34.0 |  |  | 44.1 | 41.9 |
| 44.4 | 35.1 |  |  | 40.8 | 39.6 | 31.3 |  | 39.1 | 31.2 | 32.8 |  |  | 41.6 | 43.4 |
| 43.2 | 36.2 |  |  | 42.0 | 41.9 | 32.2 |  | 36.9 | 28.6 | 32.2 |  |  | 42.4 | 43.7 |

| Participant 16 | | | Participant 17 | | | Participant 18 | | | Participant 19 | | | Participant 20 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 26.4 |  | 23.2 | 37.3 | 42.8 |  |  | 34.8 | 39.73 | 42.8 |  | 42.3 | 41.5 | 40.0 |  |
| 24.1 |  | 24.5 | 38.9 | 39.7 |  |  | 35.9 | 39.3 | 41.0 |  | 40.0 | 42.6 | 39.7 |  |
| 24.2 |  | 24.1 | 38.4 | 40.9 |  |  | 34.3 | 41.4 | 42.0 |  | 41.9 | 42.1 | 39.5 |  |
| 26.0 |  | 26.1 | 41.5 | 42.3 |  |  | 33.6 | 41.9 | 43.2 |  | 43.6 | 41.1 | 41.2 |  |
| 26.5 |  | 23.5 | 40.1 | 42.4 |  |  | 34.4 | 42.5 | 42.8 |  | 42.6 | 42.3 | 39.0 |  |

TABLE 2.5

| 24 hours | | | | | | | | | | | | | | |
|---|---|---|---|---|---|---|---|---|---|---|---|---|---|---|
| Participant 01 | | | Participant 02 | | | Participant 03 | | | Participant 04 | | | Participant 05 | | |
| S1 | S2 | S3 | S1 | S2 | S3 | S1 | S2 | S3 | S1 | S2 | S3 | S1 | S2 | S3 |
| 45.3 |  | 43.3 | 34.0 | 35.4 |  |  | 35.5 | 35.0 | 40.7 |  | 37.1 | 30.8 | 34.1 |  |
| 43.5 |  | 43.0 | 32.3 | 35.7 |  |  | 34.6 | 34.3 | 44.0 |  | 36.9 | 32.8 | 32.6 |  |
| 45.6 |  | 44.9 | 33.8 | 33.6 |  |  | 37.8 | 34.6 | 43.6 |  | 36.8 | 32.7 | 36.2 |  |
| 45.2 |  | 44.7 | 32.6 | 35.6 |  |  | 34.4 | 35.9 | 42.5 |  | 39.8 | 34.2 | 34.9 |  |
| 44.2 |  | 42.5 | 36.2 | 34.7 |  |  | 36.0 | 35.1 | 43.1 |  | 39.7 | 33.2 | 32.6 |  |

TABLE 2.5-continued

| | 24 hours | | | | | | | | | | | | | | |
|---|---|---|---|---|---|---|---|---|---|---|---|---|---|---|---|
| Participant 06 | | | Participant 07 | | | Participant 08 | | | Participant 09 | | | Participant 10 | | | |
| S1 | S2 | S3 | S1 | S2 | S3 | S1 | S2 | S3 | S1 | S2 | S3 | S1 | S2 | S3 | |
| | 43.1 | 43.0 | 34.7 | | 39.3 | 31.6 | 33.1 | | | 37.7 | 30.8 | 33.4 | | 39.5 | |
| | 45.0 | 41.9 | 36.4 | | 42.3 | 35.0 | 35.3 | | | 32.8 | 32.7 | 36.2 | | 41.1 | |
| | 44.6 | 43.9 | 37.8 | | 40.5 | 33.5 | 34.1 | | | 33.4 | 32.1 | 34.3 | | 36.6 | |
| | 43.2 | 41.7 | 36.8 | | 42.1 | 34.1 | 32.8 | | | 35.3 | 32.9 | 33.2 | | 41.7 | |
| | 45.1 | 43.5 | 36.6 | | 38.2 | 32.4 | 34.2 | | | 34.2 | 30.7 | 35.8 | | 40.6 | |
| Participant 11 | | | Participant 12 | | | Participant 13 | | | Participant 14 | | | Participant 15 | | | |
| S1 | S2 | S3 | S1 | S2 | S3 | S1 | S2 | S3 | S1 | S2 | S3 | S1 | S2 | S3 | |
| 42.2 | 32.6 | | | 44.3 | 38.2 | 31.3 | | 39.2 | 31.6 | 33.7 | | | 42.4 | 43.5 | |
| 41.3 | 35.6 | | | 42.2 | 39.6 | 31.6 | | 36.8 | 28.9 | 32.3 | | | 40.9 | 43.3 | |
| 43.4 | 35.4 | | | 42.6 | 38.9 | 29.4 | | 39.4 | 29.8 | 32.2 | | | 43.2 | 43.2 | |
| 42.2 | 35.8 | | | 44.7 | 40.2 | 30.4 | | 37.5 | 29.8 | 32.7 | | | 42.6 | 44.5 | |
| 39.7 | 34.8 | | | 44.8 | 39.5 | 33.7 | | 39.8 | 28.8 | 32.5 | | | 40.7 | 43.5 | |
| Participant 16 | | | Participant 17 | | | Participant 18 | | | Participant 19 | | | Participant 20 | | | |
| S1 | S2 | S3 | S1 | S2 | S3 | S1 | S2 | S3 | S1 | S2 | S3 | S1 | S2 | S3 | |
| 25.2 | | 48.8 | 40.9 | 41.9 | | | 34.6 | 43.3 | 41.7 | | 40.4 | 42.4 | 40.0 | | |
| 26.9 | | 23.2 | 40.2 | 41.4 | | | 35.8 | 42.4 | 43.9 | | 43.3 | 40.3 | 40.1 | | |
| 24.5 | | 25.9 | 38.8 | 41.0 | | | 35.1 | 41.0 | 41.3 | | 42.8 | 41.6 | 40.1 | | |
| 24.5 | | 24.4 | 39.4 | 42.7 | | | 34.9 | 39.7 | 42.6 | | 41.3 | 40.4 | 39.8 | | |
| 25.2 | | 24.1 | 39.8 | 40.8 | | | 33.7 | 42.0 | 43.1 | | 43.0 | 40.1 | 39.4 | | |

The calculated parameters, $\Delta h$ (Equation 1), Hti (Equation 2) and % Hti (Equation 3) can be seen in Table 3.

Tables 3 to 3.3 display the calculated $\Delta h$ values for product at a concentration of 1.0% of ucuuba butter.

TABLE 3.1

| | $\Delta h$ Values | | | | | | | | | |
|---|---|---|---|---|---|---|---|---|---|---|
| Research participant number | Product: concentration of 1.0% of ucuuba butter | | | | | Control | | | | |
| | 15 min | 2 h | 4 h | 8 h | 24 h | 15 min | 2 h | 4 h | 8 h | 24 h |
| 01 | 0.5 | 0.4 | 0.9 | 0.6 | −1.0 | 1.7 | 2.4 | 2.2 | 1.4 | −0.2 |
| 02 | 2.0 | 2.9 | 2.7 | 1.9 | 1.6 | 1.9 | 2.8 | 1.4 | 0.5 | −0.9 |
| 03 | −1.2 | −1.9 | −2.8 | −2.7 | −0.2 | 0.2 | −0.2 | −1.0 | −1.2 | 1.9 |
| 04 | −0.4 | −1.1 | −1.2 | −1.1 | −1.2 | −0.7 | −1.3 | −1.6 | −1.9 | −2.2 |
| 05 | 0.3 | 0.9 | 2.6 | 0.0 | −1.1 | 1.0 | 1.8 | 5.1 | 1.9 | 0.4 |
| 06 | 1.9 | 2.0 | 2.7 | 1.6 | 1.2 | 0.3 | −0.1 | −0.5 | −0.8 | −0.1 |
| 07 | −1.0 | −1.5 | −1.8 | −2.8 | −2.6 | −1.5 | −1.6 | −1.3 | −1.6 | −1.4 |
| 08 | −0.4 | −0.7 | −0.1 | −0.4 | −0.4 | −0.2 | −0.7 | −0.5 | −0.6 | 0.0 |
| 09 | −0.4 | −0.8 | −1.0 | −1.0 | −1.2 | −0.2 | −1.0 | −1.1 | −1.6 | −0.9 |
| 10 | −0.6 | −1.4 | 0.3 | −0.1 | −0.4 | −0.8 | −0.8 | −1.1 | −1.8 | −1.2 |
| 11 | 3.4 | 3.4 | 3.6 | 2.8 | 1.8 | 2.9 | 1.0 | 1.1 | 0.4 | −0.6 |
| 12 | −1.8 | 1.0 | −0.1 | 0.2 | 0.9 | −0.8 | −1.7 | −1.2 | −1.4 | −1.7 |
| 13 | −0.2 | −0.9 | −1.3 | −1.3 | −0.9 | −0.2 | −1.1 | −1.3 | −1.6 | −1.8 |
| 14 | −0.3 | −0.7 | −0.9 | −0.8 | −1.0 | 0.2 | −0.1 | −0.3 | 0.2 | 0.5 |
| 15 | −0.1 | −0.6 | −0.4 | −0.3 | −0.9 | −0.7 | −2.3 | −2.3 | −0.4 | 0.0 |
| 16 | −0.7 | −0.9 | −0.9 | −0.7 | −0.5 | −0.4 | −1.3 | −1.8 | −1.6 | −1.8 |
| 17 | −0.4 | −1.5 | −1.6 | −1.4 | −0.8 | −0.1 | −0.7 | −0.8 | −0.8 | −0.8 |
| 18 | −0.7 | −1.2 | −1.0 | −0.6 | −0.4 | −0.8 | −0.3 | 0.0 | −0.1 | 0.6 |
| 19 | −0.9 | −1.4 | −1.9 | −1.8 | −1.7 | −0.2 | −0.7 | −1.4 | −0.6 | −0.4 |
| 20 | 0.8 | 0.6 | 0.0 | 0.3 | −0.7 | 2.0 | 0.4 | 0.8 | 1.4 | 1.4 |

TABLE 3.2

H Values

| Research participant number | Product: concentration of 1.0% of ucuuba butter | | | | |
|---|---|---|---|---|---|
| | 15 min | 2 h | 4 h | 8 h | 24 h |
| 01 | −1.2 | −2.0 | −1.3 | −0.8 | −0.8 |
| 02 | 0.1 | 0.1 | 1.3 | 1.3 | 2.5 |
| 03 | −1.4 | −1.6 | −1.7 | −1.5 | −2.2 |
| 04 | 0.3 | 0.2 | 0.4 | 0.7 | 0.9 |
| 05 | −0.7 | −0.9 | −2.5 | −1.9 | −1.5 |
| 06 | 1.5 | 2.2 | 3.3 | 2.5 | 1.3 |
| 07 | 0.4 | 0.1 | −0.5 | −1.2 | −1.2 |
| 08 | −0.2 | 0.0 | 0.4 | 0.2 | −0.5 |
| 09 | −0.2 | 0.2 | 0.1 | 0.6 | −0.3 |
| 10 | 0.2 | −0.6 | 1.4 | 1.7 | 0.9 |
| 11 | 0.5 | 2.3 | 2.5 | 2.4 | 2.4 |
| 12 | −1.0 | 2.6 | 1.1 | 1.6 | 2.6 |
| 13 | 0.0 | 0.2 | 0.0 | 0.3 | 0.9 |
| 14 | −0.5 | −0.6 | −0.7 | −1.0 | −1.4 |
| 15 | 0.5 | 1.7 | 1.9 | 0.1 | −0.9 |
| 16 | −0.3 | 0.4 | 0.9 | 0.9 | 1.3 |
| 17 | −0.3 | −0.8 | −0.8 | −0.6 | 0.0 |
| 18 | 01.2 | −0.9 | −0.9 | −0.5 | −1.0 |
| 19 | −0.7 | −0.7 | −0.5 | −1.2 | −1.3 |
| 20 | −1.2 | 0.2 | −0.8 | −1.1 | −2.0 |

TABLE 3.3

% H Values

| Research participant number | Product: concentration of 1.0% of ucuuba butter | | | | |
|---|---|---|---|---|---|
| | 15 min | 2 h | 4 h | 8 h | 24 h |
| 01 | −2.7 | −4.4 | −3.0 | −1.9 | −1.7 |
| 02 | 0.4 | 0.4 | 4.1 | 4.1 | 7.8 |
| 03 | −3.9 | −4.6 | −4.8 | −4.3 | −6.0 |
| 04 | 0.8 | 0.6 | 1.0 | 1.9 | 2.3 |
| 05 | −2.2 | −2.8 | −7.4 | −5.7 | −4.4 |
| 06 | 3.6 | 5.0 | 7.6 | 5.7 | 3.1 |
| 07 | 1.0 | 0.2 | −1.1 | −2.8 | −2.9 |
| 08 | −0.7 | 0.0 | 1.1 | 0.5 | −1.4 |
| 09 | −0.6 | 0.5 | 0.3 | 1.7 | −0.7 |
| 10 | 0.5 | −1.5 | 3.4 | 4.3 | 2.1 |
| 11 | 1.3 | 5.8 | 6.3 | 6.0 | 6.0 |
| 12 | −2.4 | 6.2 | 2.5 | 3.6 | 6.1 |
| 13 | 0.1 | 0.5 | 0.1 | 0.7 | 2.2 |
| 14 | −1.5 | −1.9 | −2.1 | −3.2 | −4.7 |
| 15 | 1.3 | 3.9 | 4.4 | 0.3 | −2.1 |
| 16 | −1.2 | 1.7 | 3.5 | 3.6 | 5.1 |
| 17 | −0.6 | −2.0 | −1.9 | −1.6 | 0.0 |
| 18 | 0.5 | −2.6 | −2.7 | −1.5 | −2.9 |
| 19 | −1.5 | −1.6 | −1.1 | −2.8 | −3.0 |
| 20 | −2.8 | 0.4 | −1.9 | −2.5 | −4.9 |

FIG. 1 displays the average values of the capacitance measurements (h) obtained through control and after applying the product, at all assessment times.

In order to evaluate the significance of skin hydration after application of the product followed by rinsing, several statistical analyses were carried out, as described below.

Table 4 shows the statistical analysis results obtained by evaluating basal homogeneity between the sites of application of the product and control. The complete data can be found in Table 5.

TABLE 4

Summarized data on the statistical analysis on basal homogeneity P Values

| Comparison Group | Parameter: h |
|---|---|
| h Product vs. h Control | 0.4789 (non-significant) |

According to the results obtained, there was no significant difference ($P>0.05$) between the basal capacitance values obtained for the areas where product and control were assessed, which evinces homogeneity between sites.

Tables 5 to 5.3 display the complete data on the statistical analysis on the product at a concentration of 1.0% of ucuuba.

TABLE 5

Statistical analysis = basal homogeneity: Basal Homogeneity

| Paired t Test | |
|---|---|
| P Value | 0.4789 |
| P Value summary | ns |
| Significantly different? (P < 0.05) | No |
| One- or two-tailed P value? | Two-tailed |
| t, df | t = 0.7223 df = 19 |
| Number of pairs | 20 |
| How big is the difference? | |
| Mean difference | −0.555 |
| SD of the differences | 3.436 |
| SEM of the differences | 0.7683 |
| 95% confidence interval | −2.163 to 1.053 |
| R square | 0.02673 |

TABLE 5.1

Significance of the Effect - Product: concentration of 1.0% of ucuuba butter

| Paired t Test | Initial vs. after 15 minutes | Initial vs. after 2 hours | Initial vs. after 4 hours | Initial vs. after 8 hours | Initial vs. after 24 hours |
|---|---|---|---|---|---|
| P Value | 0.9857 | 0.6061 | 0.7857 | 0.2417 | 0.0705 |
| P Value summary | ns | ns | ns | ns | ns |
| Significantly different? (P < 0.05) | No | No | No | No | No |
| One- or two-tailed P value? | Two-tailed | Two-tailed | Two-tailed | Two-tailed | Two-tailed |
| t, df | t = 0.01811 df = 19 | t = 0.5244 df = 19 | t = 0.2758 df = 19 | t = 1.208 df = 19 | t = 1.916 df = 19 |
| Number of pairs | 20 | 20 | 20 | 20 | 20 |

TABLE 5.1-continued

Significance of the Effect - Product: concentration of 1.0% of ucuuba butter

| Paired t Test | Initial vs. after 15 minutes | Initial vs. after 2 hours | Initial vs. after 4 hours | Initial vs. after 8 hours | Initial vs. after 24 hours |
|---|---|---|---|---|---|
| How big is the difference? | | | | | |
| Mean difference | −0.005 | −0.178 | −0.109 | −0.38 | −0.472 |
| SD of the differences | 1.234 | 1.518 | 1.768 | 1.406 | 1.102 |
| SEM of the differences | 0.276 | 0.3394 | 0.3952 | 0.3145 | 0.2463 |
| 95% confidence interval | −0.5827 to 0.5727 | −0.8885 to 0.5325 | −0.9362 to 0.7182 | −1.038 to 0.2782 | −0.9876 to 0.04356 |
| R square | 0.00001727 | 0.01427 | 0.003987 | 0.07136 | 0.162 |

TABLE 5.2

Control
Significance of the Effect - Control

| Paired t Test | Initial vs. after 15 minutes | Initial vs. after 2 hours | Initial vs. after 4 hours | Initial vs. after 8 hours | Initial vs. after 24 hours |
|---|---|---|---|---|---|
| P Value | 0.4806 | 0.3691 | 0.4647 | 0.0694 | 0.0771 |
| P Value summary | ns | ns | ns | ns | ns |
| Significantly different? (P < 0.05) | No | No | No | No | No |
| One- or two-tailed P value? | Two-tailed | Two-tailed | Two-tailed | Two-tailed | Two-tailed |
| t, df | t = 0.7195 df = 19 | t = 0.9201 df = 19 | t = 0.7461 df = 19 | t = 1.925 df = 19 | t = 1.869 df = 19 |
| Number of pairs | 20 | 20 | 20 | 20 | 20 |
| How big is the difference? | | | | | |
| Mean difference | 0.185 | −0.279 | −0.286 | −0.497 | −0.454 |
| SD of the differences | 1.15 | 1.356 | 1.714 | 1.155 | 1.086 |
| SEM of the differences | 0.2571 | 0.3032 | 0.3833 | 0.2582 | 0.2429 |
| 95% confidence interval | −0.3531 to 0.7231 | −0.9137 to 0.3557 | −1.088 to 0.5163 | −1.038 to 0.04351 | −0.9623 to 0.05434 |
| R square | 0.02653 | 0.04266 | 0.02846 | 0.1631 | 0.1553 |

TABLE 5.3

Comparison between product and control
Comparison between Product: concentration of 1.0% of ucuuba butter Vs. Control

| Paired t Test | Initial vs. after 15 minutes | Initial vs. after 2 hours | Initial vs. after 4 hours | Initial vs. after 8 hours | Initial vs. after 24 hours |
|---|---|---|---|---|---|
| P Value | 0.26 | 0.7165 | 0.6056 | 0.6629 | 0.9652 |
| P Value summary | ns | ns | ns | ns | ns |
| Significantly different? (P < 0.05) | No | No | No | No | No |
| One- or two-tailed P value? | Two-tailed | Two-tailed | Two-tailed | Two-tailed | Two-tailed |
| t, df | t = 1.161 df = 19 | t = 0.3686 df = 19 | t = 0.5250 df = 19 | t = 0.4429 df = 19 | t = 0.04421 df = 19 |
| Number of pairs | 20 | 20 | 20 | 20 | 20 |
| How big is the difference? | | | | | |
| Mean difference | 0.19 | −0.105 | −0.17 | −0.13 | 0.015 |
| SD of the differences | 0.7319 | 1.274 | 1.448 | 1.313 | 1.517 |
| SEM of the differences | 0.1637 | 0.2848 | 0.3238 | 0.2935 | 0.3393 |

TABLE 5.3-continued

Comparison between product and control
Comparison between Product: concentration of 1.0% of ucuuba butter Vs. Control

| Paired t Test | Initial vs. after 15 minutes | Initial vs. after 2 hours | Initial vs. after 4 hours | Initial vs. after 8 hours | Initial vs. after 24 hours |
|---|---|---|---|---|---|
| 95% confidence interval | −0.1525 to 0.5325 | −0.7012 to 0.4912 | −0.8477 to 0.5077 | −0.7444 to 0.4844 | −0.6952 to 0.7252 |
| R square | 0.06624 | 0.007101 | 0.0143 | 0.01022 | 0.0001029 |

Table 6 summarizes the results obtained with the statistical analysis on the significance of the variations in the capacitance values throughout the study for product and control.

TABLE 6

Summarized data on the statistical analysis on the significance of changes in the cutaneous barrier. P Values

| Comparison Group | Control | Product: concentration of 1.0% of ucuuba butter |
|---|---|---|
| ht0 vs. ht15 min | 0.4806 (non-significant) | 0.9857 (significant) |
| ht0 vs. ht2 | 0.3691 (non-significant) | <0.6061 (significant) |
| ht0 vs. ht4 | 0.4647 (non-significant) | <0.7857 (significant) |
| ht0 vs. ht8 | 0.0694 (non-significant) | <0.2417 (significant) |
| ht0 vs. ht24 | 0.0771 (non-significant) | <0.0705 (significant) |

According to the results it was possible to observe that:
no significant variations (P>0.05) were observed in the values of h at the control site after 15 minutes, 2, 4, 8 and 24 hours, indicating that there was no significant change in skin hydration.
for the product with concentration of 1.0% ucuuba butter no significant variations (P>0.05) were observed in the values of h at the product site after 15 minutes, 2, 4, 8 and 24 hours, indicating that the skin's natural hydration was maintained.

The results of the statistical analysis to evaluate the significance of skin hydration afforded by the product in relation to the control are summarized in Table 7.

TABLE 7

Data summarized from the statistical analysis of the comparison of Product vs. Control. P Values

| Comparison Group | 15 minutes after application | 2 hours after application | 4 hours after application | 8 hours after application | 24 hours after application |
|---|---|---|---|---|---|
| $\Delta h_{ti, P}$ vs. $\Delta h_{ti, C}$ | 0.2600 (non-significant) | 0.7165 (non-significant) | 0.6056 (non-significant) | 0.6629 (non-significant) | 0.9652 (non-significant) |

The skin hydration provided by the product containing concentration of 1.0% ucuuba butter was not significantly (P>0.05) higher 15 minutes, 2, 4, 8 and 24 hours after application, as compared to the control. However, it was observed that 45%, 55%, 55%, 55% and 40% of the research subjects showed improvement in skin hydration after 15, 2, 4, 8 and 24 hours after application, respectively.

6. Conclusion

According to the study protocol and procedures used for the evaluation of skin hydration, it was observed that the application, followed by rinsing of the product containing a concentration of 1.0% ucuuba butter on the skin in the forearm region:
maintained skin's natural hydration for 15 minutes, 2, 4, 8 and 24 hours after application.

did not confer significantly higher hydration when compared to the control (skin without application of any products); however, 55% of the research participants showed improvement in skin hydration after applying the product.

Test 2—Evaluation of Skin Hydration by Corneometry after Rinsing the Product Applied at a Concentration of 2.5% Ucuuba 1. Objective Evaluate the level of skin hydration after application of the formulation in the Table K above.

2. Table of Volunteers

The same aspects of TEST 1 apply to TEST 2.

3. Procedures for Conducting Evaluations 3.1. General Overview

The same aspects of TEST 1 apply to TEST 2.

The determination of the control site (without application of any products) and product application site was randomized between the delimited sites, as recorded in the correlation worksheet in Table 8 below.

TABLE 8

| Research participant code | Age | Photo-type | Application Sites | | |
|---|---|---|---|---|---|
| | | | Site 1 | Site 2 | Site 3 |
| 01 | 45 | III | Control | Product: concentration of 2.5% butter ucuuba | |
| 02 | 22 | IV | | Control | Product: concentration of 2.5% ucuuba butter |
| 03 | 35 | III | Product: concentra- | | Control |

TABLE 8-continued

| Research participant code | Age | Photo-type | Site 1 | Site 2 | Site 3 |
|---|---|---|---|---|---|
| 04 | 57 | III | Control | Product: concentration of 2.5% ucuuba butter | |
| 05 | 60 | III | | Control | Product: concentration of 2.5% ucuuba butter |
| 06 | 43 | IV | Product: concentration of 2.5% ucuuba butter | | Control |
| 07 | 56 | III | Control | Product: concentration of 2.5% ucuuba butter | |
| 08 | 55 | III | | Control | Product: concentration of 2.5% ucuuba butter |
| 09 | 48 | III | Product: concentration of 2.5% ucuuba butter | | Control |
| 10 | 53 | IV | Control | Product: concentration of 2.5% ucuuba butter | |
| 11 | 30 | III | | Control | Product: concentration of 2.5% ucuuba butter |
| 12 | 57 | III | Product: concentration of 2.5% ucuuba butter | | Control |
| 13 | 50 | III | Control | Product: concentration of 2.5% ucuuba butter | |
| 14 | 60 | III | | Control | Product: concentration of 2.5% ucuuba butter |
| 15 | 48 | III | Product: concentration of 2.5% ucuuba butter | | Control |
| 16 | 44 | III | Control | Product: concentration of 2.5% ucuuba butter | |
| 17 | 41 | IV | | Control | Product: concentration of 2.5% ucuuba butter |
| 18 | 44 | III | Product: concentration of 2.5% ucuuba butter | | Control |
| 19 | 54 | III | Control | Product: concentration of 2.5% ucuuba butter | |
| 20 | 48 | III | | Control | Product: concentration of 2.5% ucuuba butter |

After 30 minutes of acclimatization in controlled environment at a 20±2° C. temperature and 50±5% of relative humidity, the basal measurements (prior to application of the product) of skin capacitance were obtained in the delimited sites. Then, an amount of 20 uL of the product was applied, by rubbing it homogeneously over the site with the aid of a disposable finger stall.

After the application, the research participants remained in the laboratory to make capacitance measurements after 15 minutes, 2, 4, 8 and 24 hours. After the κ hour-measurement, the research participants returned home, and were advised not to water or wash the arms. The next day, they returned to the laboratory for performing the measurement after 24 hours following the sample application.

Throughout the experiment in the laboratory, the climate conditions were kept constant according to the aforementioned ranges.

3.2. Application and Rinsing of the Product
The same aspects of TEST 1 apply to TEST 2.
3.3. Capacitance Measurement Acquisition
The same aspects of TEST 1 apply to TEST 2.
4. Data Analysis and Interpretation
4.1. Software for Obtaining the Average Values and Data Analysis:
The same aspects of TEST 1 apply to TEST 2.
4.2. Software for Statistical Analysis:
The same aspects of TEST 1 apply to TEST 2.
4.3. Interpretation of Results
The same aspects of TEST 1 apply to TEST 2.
4.3.1. CALCULATIONS
The same aspects of TEST 1 apply to TEST 2.
4.3.2. Statistical Evaluations
4.3.2.1. Basal Homogeneity
The same aspects of TEST 1 apply to TEST 2.
4.3.2.2. Significance of the Effect
The same aspects of TEST 1 apply to TEST 2.
4.3.2.3. Comparison Between Product and Control
The same aspects of TEST 1 apply to TEST 2.
5. Results and Discussions:
5.1. Statistics on the Participation of Volunteers
Total contacted volunteers: 110;
Table of volunteers: 34;
Total absences on the day of the study: 14;
Total volunteers dismissed after evaluation of inclusion and exclusion criteria: 0;
Effectively included volunteers: 20;
Volunteers who completed the study: 20.

5.2. General Data on the Study Group

Average age: 48±10 years.

Phototype (Fitzpatrick): 80% phototype III e 20% phototype IV.

5.3. Climate Control

Statistical data on the environmental monitoring in the waiting and climate room of the research participants during the days of the study was carried out:

Day 1
Temperature: (21.2±0.5° C. (95% confidence interval: 21.0° C. to 21.4° C.)
Relative humidity of air: (49±2) % (95% confidence interval: 48% to 50%)

Day 2
Temperature: (21.2±0.5° C. (95% confidence interval: 21.0° C. to 21.4° C.)
Relative humidity of air: (49±2) % (95% confidence interval: 48% to 50%)

Day 3
Temperature: (21.0±0.5° C. (95% confidence interval: 20.7° C. to 21.3° C.)
Relative humidity of air: (50±2) % (95% confidence interval: 48% to 51%)

According to the data recorded on the climate control, temperature and humidity in the waiting and climate room of the participants remained within the range established in the study protocol.

5.4. Results Obtained from the Evaluation

Skin hydration was assessed through capacitance measurements. Table 9 lists all measurements carried out.

Tablet 9 9.5 describe the measured values of the product capacitance at a concentration of 2.5% ucuuba.

TABLE 9

| Basal | | | | | | | | | | | | | | |
|---|---|---|---|---|---|---|---|---|---|---|---|---|---|---|
| Participant 01 | | | Participant 02 | | | Participant 03 | | | Participant 04 | | | Participant 05 | | |
| S1 | S2 | S3 | S1 | S2 | S3 | S1 | S2 | S3 | S1 | S2 | S3 | S1 | S2 | S3 |
| 46.4 | 41.4 | | | 34.7 | 35.3 | 32.0 | | 31.4 | 44.9 | 4.8 | | | 32.9 | 32.1 |
| 43.2 | 44.5 | | | 34.5 | 34.6 | 32.5 | | 35.9 | 46.9 | 44.2 | | | 33.3 | 32.6 |
| 44.3 | 45.0 | | | 35.8 | 33.3 | 33.1 | | 33.5 | 43.4 | 40.4 | | | 32.6 | 33.3 |
| 43.1 | 46.9 | | | 36.9 | 33.0 | 36.5 | | 31.8 | 46.4 | 46.3 | | | 34.6 | 32.4 |
| 47.9 | 44.7 | | | 37.5 | 36.0 | 34.9 | | 32.6 | 43.1 | 44.9 | | | 35.1 | 32.9 |

| Participant 06 | | | Participant 07 | | | Participant 08 | | | Participant 09 | | | Participant 10 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 35.1 | | 43.6 | 36.4 | 40.4 | | | 33.7 | 33.0 | 34.7 | | 31.8 | 34.8 | 36.5 | |
| 36.0 | | 41.3 | 36.6 | 45.8 | | | 34.3 | 31.2 | 32.8 | | 34.3 | 34.5 | 36.8 | |
| 37.5 | | 41.7 | 37.4 | 43.4 | | | 33.1 | 32.1 | 31.5 | | 32.5 | 36.6 | 35.7 | |
| 39.4 | | 43.5 | 39.0 | 41.4 | | | 34.4 | 33.2 | 32.4 | | 32.9 | 36.4 | 38.2 | |
| 38.2 | | 44.4 | 39.7 | 42.4 | | | 33.8 | 32.0 | 33.3 | | 32.3 | 36.7 | 38.0 | |

| Participant 11 | | | Participant 12 | | | Participant 13 | | | Participant 14 | | | Participant 15 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| | 33.1 | 37.8 | 35.9 | | 39.7 | 31.4 | 36.8 | | | 31.0 | 33.7 | 39.4 | | 44.0 |
| | 36.1 | 34.6 | 37.3 | | 41.4 | 33.0 | 34.5 | | | 31.9 | 33.9 | 40.3 | | 43.2 |
| | 36.8 | 38.6 | 39.2 | | 40.4 | 32.6 | 32.0 | | | 33.2 | 34.7 | 40.6 | | 43.7 |
| | 34.2 | 36.8 | 36.2 | | 43.4 | 32.8 | 35.4 | | | 31.2 | 35.7 | 43.1 | | 42.1 |
| | 37.0 | 34.9 | 39.4 | | 40.0 | 35.6 | 33.1 | | | 33.7 | 34.4 | 42.7 | | 44.8 |

| Participant 16 | | | Participant 17 | | | Participant 18 | | | Participant 19 | | | Participant 20 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 27.1 | 24.7 | | | 40.4 | 38.9 | 31.8 | | 42.2 | 40.2 | 44.7 | | | 37.5 | 33.4 |
| 26.0 | 22.3 | | | 43.6 | 37.1 | 32.4 | | 37.8 | 45.0 | 43.7 | | | 37.9 | 36.1 |
| 29.2 | 23.6 | | | 43.4 | 37.9 | 32.2 | | 40.8 | 41.2 | 42.6 | | | 38.5 | 36.9 |
| 26.2 | 25.6 | | | 41.4 | 38.5 | 33.2 | | 43.3 | 44.9 | 41.1 | | | 40.0 | 35.9 |
| 26.6 | 23.1 | | | 43.2 | 38.4 | 33.6 | | 41.1 | 43.3 | 42.7 | | | 38.7 | 34.1 |

TABLE 9.1

| 15 minutes | | | | | | | | | | | | | | |
|---|---|---|---|---|---|---|---|---|---|---|---|---|---|---|
| Participant 01 | | | Participant 02 | | | Participant 03 | | | Participant 04 | | | Participant 05 | | |
| S1 | S2 | S3 | S1 | S2 | S3 | S1 | S2 | S3 | S1 | S2 | S3 | S1 | S2 | S3 |
| 45.1 | 44.3 | | | 37.3 | 36.5 | 32.2 | | 33.0 | 43.5 | 43.2 | | | 36.9 | 35.8 |
| 46.7 | 44.7 | | | 36.0 | 34.4 | 33.5 | | 32.2 | 45.9 | 41.1 | | | 34.4 | 32.2 |
| 45.7 | 48.2 | | | 39.4 | 35.1 | 34.8 | | 34.1 | 42.8 | 44.3 | | | 33.3 | 34.5 |

TABLE 9.1-continued

| 15 minutes | | | | | | | | | | | | | | |
|---|---|---|---|---|---|---|---|---|---|---|---|---|---|---|
| 47.3 | 44.8 | | | 37.4 | 37.8 | 34.4 | | 32.6 | 44.1 | 45.6 | | | 34.6 | 34.8 |
| 48.8 | 43.9 | | | 38.8 | 36.7 | 34.6 | | 34.5 | 45.0 | 45.2 | | | 34.4 | 35.9 |

| Participant 06 | | | Participant 07 | | | Participant 08 | | | Participant 09 | | | Participant 10 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 38.1 | | 42.0 | 37.7 | 38.7 | | | 31.8 | 31.0 | 31.0 | | 30.2 | 35.3 | 34.3 | |
| 37.4 | | 42.3 | 38.7 | 43.7 | | | 33.9 | 30.7 | 32.1 | | 32.3 | 34.1 | 38.0 | |
| 40.4 | | 41.9 | 34.3 | 44.1 | | | 35.0 | 32.2 | 32.3 | | 33.0 | 32.7 | 36.8 | |
| 40.5 | | 45.7 | 34.5 | 41.9 | | | 33.3 | 30.7 | 32.2 | | 32.9 | 36.9 | 35.7 | |
| 38.9 | | 44.2 | 36.5 | 40.2 | | | 34.4 | 32.4 | 32.6 | | 34.2 | 35.9 | 36.6 | |

| Participant 11 | | | Participant 12 | | | Participant 13 | | | Participant 14 | | | Participant 15 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| | 37.3 | 39.3 | 38.8 | | 39.3 | 34.8 | 35.0 | | | 31.8 | 33.5 | 41.5 | | 41.6 |
| | 37.7 | 39.8 | 36.1 | | 39.8 | 32.3 | 33.5 | | | 30.1 | 34.0 | 40.7 | | 42.7 |
| | 38.2 | 37.1 | 37.5 | | 40.2 | 31.4 | 33.7 | | | 34.2 | 32.1 | 41.9 | | 43.3 |
| | 38.7 | 37.0 | 37.5 | | 41.1 | 32.4 | 35.7 | | | 33.7 | 33.5 | 40.3 | | 44.7 |
| | 39.9 | 40.6 | 38.2 | | 40.6 | 33.5 | 34.0 | | | 32.1 | 36.5 | 42.3 | | 42.2 |

| Participant 16 | | | Participant 17 | | | Participant 18 | | | Participant 19 | | | Participant 20 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 26.5 | 23.7 | | | 42.0 | 37.8 | 32.6 | | 41.8 | 41.5 | 42.7 | | | 40.2 | 37.6 |
| 25.8 | 25.0 | | | 42.4 | 38.6 | 34.0 | | 39.3 | 43.5 | 42.4 | | | 41.0 | 34.6 |
| 26.7 | 22.8 | | | 43.6 | 38.0 | 32.0 | | 38.4 | 43.3 | 43.9 | | | 42.0 | 35.9 |
| 26.8 | 23.2 | | | 40.9 | 39.1 | 32.2 | | 40.9 | 42.4 | 43.3 | | | 39.1 | 39.3 |
| 27.2 | 22.8 | | | 42.4 | 37.5 | 30.8 | | 40.7 | 42.9 | 42.8 | | | 40.3 | 37.7 |

TABLE 9.2

| 2 hours | | | | | | | | | | | | | | |
|---|---|---|---|---|---|---|---|---|---|---|---|---|---|---|
| Participant 01 | | | Participant 02 | | | Participant 03 | | | Participant 04 | | | Participant 05 | | |
| S1 | S2 | S3 | S1 | S2 | S3 | S1 | S2 | S3 | S1 | S2 | S3 | S1 | S2 | S3 |
| 47.2 | 46.1 | | | 39.4 | 35.9 | 35.0 | | 32.9 | 41.8 | 41.4 | | | 35.1 | 36.0 |
| 49.3 | 46.0 | | | 39.8 | 36.3 | 32.4 | | 33.2 | 42.2 | 43.5 | | | 37.8 | 33.2 |
| 48.2 | 43.2 | | | 38.2 | 36.7 | 32.9 | | 31.3 | 44.2 | 45.1 | | | 33.3 | 35.4 |
| 47.3 | 44.5 | | | 37.9 | 37.7 | 33.3 | | 34.3 | 46.3 | 42.5 | | | 35.6 | 34.5 |
| 45.0 | 47.2 | | | 37.9 | 35.0 | 32.3 | | 32.3 | 43.6 | 42.6 | | | 35.7 | 35.6 |

| Participant 06 | | | Participant 07 | | | Participant 08 | | | Participant 09 | | | Participant 10 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 39.0 | | 42.4 | 34.5 | 40.0 | | | 33.1 | 31.6 | 33.7 | | 31.6 | 34.5 | 35.7 | |
| 38.4 | | 41.8 | 37.2 | 43.3 | | | 33.5 | 29.2 | 31.8 | | 32.6 | 36.2 | | |
| 39.8 | | 42.3 | 37.9 | 40.3 | | | 33.3 | 31.1 | 31.5 | | 30.3 | 36.0 | 35.8 | |
| 39.7 | | 43.8 | 36.3 | 41.4 | | | 34.7 | 32.9 | 32.0 | | 32.6 | 34.0 | 35.0 | |
| 39.5 | | 43.5 | 35.0 | 43.9 | | | 31.1 | 31.2 | 33.8 | | 31.6 | 37.7 | 35.7 | |

| Participant 11 | | | Participant 12 | | | Participant 13 | | | Participant 14 | | | Participant 15 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| | 36.0 | 35.6 | 35.9 | | 38.3 | 31.1 | 35.4 | | | 31.3 | 34.0 | 39.9 | | 42.4 |
| | 35.8 | 37.1 | 37.1 | | 39.0 | 33.7 | 32.5 | | | 32.3 | 32.3 | 40.4 | | 40.5 |
| | 35.7 | 36.7 | 38.0 | | 38.0 | 31.4 | 34.4 | | | 33.3 | 34.1 | 40.0 | | 42.1 |
| | 37.2 | 35.9 | 36.9 | | 40.1 | 31.3 | 32.2 | | | 32.1 | 34.6 | 39.3 | | 40.0 |
| | 37.7 | 39.3 | 36.6 | | 41.2 | 32.6 | 34.8 | | | 31.5 | 32.6 | 41.2 | | 41.5 |

| Participant 16 | | | Participant 17 | | | Participant 18 | | | Participant 19 | | | Participant 20 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 25.5 | 22.9 | | | 39.1 | 36.7 | 30.8 | | 38.8 | 40.5 | 42.9 | | | 38.6 | 38.1 |
| 24.1 | 24.1 | | | 43.2 | 38.2 | 31.4 | | 41.0 | 42.7 | 42.0 | | | 38.0 | 36.8 |
| 25.7 | 22.2 | | | 41.0 | 36.5 | 33.7 | | 42.0 | 42.5 | 43.7 | | | 38.4 | 36.4 |

TABLE 9.2-continued

| 2 hours | | | | | | | | | | | | | | |
|---|---|---|---|---|---|---|---|---|---|---|---|---|---|---|
| 26.8 | 24.2 | | 42.2 | 37.9 | 34.3 | | 40.8 | 42.3 | 40.9 | | | 40.5 | 38.3 | |
| 26.3 | 23.7 | | 43.2 | 38.8 | 33.8 | | 40.9 | 43.1 | 45.0 | | | 39.1 | 39.3 | |

TABLE 9.3

| 4 hours |
|---|

| Participant 01 | | | Participant 02 | | | Participant 03 | | | Participant 04 | | | Participant 05 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 46.1 | 43.6 | | | 38.6 | 35.3 | 31.0 | | 32.7 | 41.5 | 41.5 | | | 39.9 | 38.8 |
| 48.2 | 46.3 | | | 37.2 | 36.3 | 31.8 | | 32.4 | 44.0 | 43.4 | | | 39.4 | 38.2 |
| 45.6 | 47.7 | | | 37.8 | 36.4 | 34.8 | | 32.0 | 44.3 | 44.5 | | | 38.3 | 36.0 |
| 47.8 | 46.4 | | | 35.2 | 38.2 | 33.7 | | 32.4 | 42.6 | 42.9 | | | 36.8 | 38.4 |
| 48.3 | 45.5 | | | 37.7 | 34.8 | 33.9 | | 30.5 | 44.5 | 43.0 | | | 39.5 | 36.8 |

| Participant 06 | | | Participant 07 | | | Participant 08 | | | Participant 09 | | | Participant 10 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 41.3 | | 42.4 | 36.6 | 40.2 | | | 33.7 | 30.6 | 31.9 | | 31.3 | 34.4 | 34.3 | |
| 38.4 | | 43.3 | 35.1 | 43.3 | | | 31.4 | 30.3 | 31.6 | | 32.3 | 35.7 | 35.9 | |
| 36.8 | | 39.8 | 38.1 | 40.0 | | | 34.3 | 32.3 | 34.6 | | 30.8 | 36.9 | 33.4 | |
| 39.0 | | 43.5 | 34.3 | 40.6 | | | 33.3 | 30.4 | 33.2 | | 30.4 | 33.1 | 34.8 | |
| 38.3 | | 42.9 | 38.3 | 41.3 | | | 34.3 | 32.4 | 32.3 | | 33.4 | 33.5 | 37.3 | |

| Participant 11 | | | Participant 12 | | | Participant 13 | | | Participant 14 | | | Participant 15 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| | 35.6 | 35.8 | 38.6 | | 39.6 | 32.8 | 32.0 | | | 31.7 | 35.2 | 41.1 | | 41.1 |
| | 36.0 | 35.6 | 38.9 | | 40.3 | 29.9 | 33.5 | | | 32.0 | 33.9 | 40.8 | | 41.5 |
| | 37.1 | 36.0 | 37.3 | | 37.3 | 31.9 | 33.2 | | | 32.0 | 34.7 | 40.2 | | 42.0 |
| | 35.7 | 36.8 | 39.2 | | 40.9 | 33.5 | 32.6 | | | 30.1 | 34.4 | 39.8 | | 41.0 |
| | 38.3 | 39.8 | 39.5 | | 40.7 | 30.6 | 34.1 | | | 33.8 | 32.5 | 39.1 | | 40.6 |

| Participant 16 | | | Participant 17 | | | Participant 18 | | | Participant 19 | | | Participant 20 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 25.4 | 22.8 | | | 40.0 | 37.8 | 33.5 | | 39.9 | 42.0 | 43.1 | | | 40.2 | 36.6 |
| 24.1 | 22.6 | | | 39.9 | 35.8 | 32.3 | | 40.0 | 42.8 | 43.5 | | | 38.4 | 38.6 |
| 24.8 | 23.5 | | | 43.6 | 38.6 | 33.5 | | 41.2 | 43.1 | 41.8 | | | 39.6 | 38.9 |
| 27.0 | 23.9 | | | 43.3 | 39.5 | 32.7 | | 40.4 | 40.5 | 42.4 | | | 39.1 | 36.2 |
| 24.9 | 22.4 | | | 41.1 | 35.4 | 32.5 | | 43.6 | 39.0 | 42.1 | | | 39.3 | 37.3 |

TABLE 9.4

| 8 hours |
|---|

| Participant 01 | | | Participant 02 | | | Participant 03 | | | Participant 04 | | | Participant 05 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 46.3 | 46.4 | | | 38.1 | 35.6 | 33.7 | | 31.4 | 42.3 | 42.9 | | | 33.6 | 33.5 |
| 45.2 | 45.6 | | | 37.0 | 37.8 | 31.1 | | 32.9 | 41.8 | 43.5 | | | 38.2 | 35.7 |
| 46.1 | 46.4 | | | 37.4 | 35.6 | 32.6 | | 31.6 | 44.8 | 42.8 | | | 34.3 | 35.1 |
| 45.9 | 44.3 | | | 35.4 | 35.1 | 32.7 | | 32.6 | 44.4 | 43.1 | | | 35.4 | 35.4 |
| 48.6 | 45.9 | | | 34.2 | 36.1 | 33.9 | | 30.9 | 42.1 | 42.6 | | | 36.6 | 34.5 |

| Participant 06 | | | Participant 07 | | | Participant 08 | | | Participant 09 | | | Participant 10 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 38.9 | | 43.2 | 37.8 | 39.0 | | | 33.5 | 29.0 | 31.6 | | 32.0 | 35.5 | 35.0 | |
| 37.3 | | 41.4 | 35.3 | 41.8 | | | 34.3 | 30.0 | 30.3 | | 31.0 | 33.4 | 34.0 | |

TABLE 9.4-continued

| 8 hours | | | | | | | | | | | | | | |
|---|---|---|---|---|---|---|---|---|---|---|---|---|---|---|
| 38.1 | | 42.1 | 35.4 | 43.7 | | 31.3 | 31.7 | 33.6 | | 33.0 | 32.7 | 34.1 | | |
| 38.7 | | 42.1 | 35.5 | 39.2 | | 34.1 | 32.5 | 31.7 | | 29.2 | 32.1 | 37.6 | | |
| 38.2 | | 41.6 | 37.1 | 38.7 | | 33.3 | 30.8 | 32.1 | | 30.5 | 36.2 | 35.8 | | |

| Participant 11 | | | Participant 12 | | | Participant 13 | | | Participant 14 | | | Participant 15 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| | 36.5 | 38.1 | 37.1 | | 40.7 | 30.8 | 32.6 | | | 30.3 | 35.1 | 39.5 | | 43.7 |
| | 35.3 | 33.5 | 38.7 | | 37.5 | 32.6 | 32.1 | | | 32.5 | 34.2 | 40.8 | | 43.2 |
| | 36.1 | 35.1 | 36.5 | | 38.3 | 30.7 | 35.8 | | | 34.0 | 35.1 | 42.4 | | 41.9 |
| | 35.1 | 36.5 | 35.0 | | 39.6 | 31.3 | 32.9 | | | 32.8 | 32.4 | 41.8 | | 43.4 |
| | 36.2 | 37.6 | 38.7 | | 41.9 | 32.2 | 34.8 | | | 32.2 | 33.2 | 38.0 | | 43.7 |

| Participant 16 | | | Participant 17 | | | Participant 8 | | | Participant 19 | | | Participant 20 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 26.4 | 22.7 | | | 42.8 | 36.5 | 30.9 | | 39.7 | 42.8 | 44.3 | | | 40.0 | 37.5 |
| 24.1 | 21.3 | | | 39.7 | 37.2 | 31.5 | | 39.3 | 41.0 | 44.0 | | | 39.7 | 39.4 |
| 24.2 | 23.5 | | | 40.9 | 38.4 | 30.3 | | 41.4 | 42.0 | 43.0 | | | 39.5 | 35.9 |
| 26.0 | 24.8 | | | 42.3 | 37.2 | 34.7 | | 41.9 | 43.2 | 43.0 | | | 41.2 | 37.5 |
| 26.5 | 22.5 | | | 42.4 | 37.1 | 32.7 | | 42.5 | 42.8 | 40.3 | | | 39.0 | 38.1 |

TABLE 9.5

| 24 hours | | | | | | | | | | | | | | |
|---|---|---|---|---|---|---|---|---|---|---|---|---|---|---|
| Participant 01 | | | Participant 02 | | | Participant 03 | | | Participant 04 | | | Participant 05 | | |
| S1 | S2 | S3 | S1 | S2 | S3 | S1 | S2 | S3 | S1 | S2 | S3 | S1 | S2 | S3 |
| 45.3 | 43.8 | | | 35.4 | 36.9 | 34.5 | | 35.0 | 40.7 | 42.3 | | | 34.1 | 32.0 |
| 43.5 | 43.6 | | | 35.7 | 37.1 | 34.2 | | 34.3 | 44.0 | 41.1 | | | 32.6 | 32.6 |
| 45.6 | 44.0 | | | 33.6 | 33.1 | 33.7 | | 34.6 | 43.6 | 43.4 | | | 36.2 | 36.0 |
| 45.2 | 45.4 | | | 35.6 | 36.3 | 33.5 | | 35.9 | 42.5 | 41.3 | | | 34.9 | 32.7 |
| 44.2 | 43.9 | | | 34.7 | 35.4 | 33.6 | | 35.1 | 43.1 | 41.6 | | | 32.6 | 33.8 |

| Participant 06 | | | Participant 07 | | | Participant 08 | | | Participant 09 | | | Participant 10 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 37.0 | | 43.0 | 34.7 | 41.8 | | | 33.1 | 32.6 | 31.5 | | 30.8 | 33.4 | 35.5 | |
| 38.7 | | 41.9 | 36.4 | 40.8 | | | 35.3 | 31.0 | 31.4 | | 32.7 | 36.2 | 35.7 | |
| 39.3 | | 43.9 | 37.8 | 41.2 | | | 34.1 | 30.7 | 31.9 | | 32.1 | 34.3 | 36.7 | |
| 37.1 | | 41.7 | 36.8 | 40.4 | | | 32.8 | 29.5 | 33.6 | | 32.9 | 33.2 | 36.0 | |
| 39.1 | | 43.5 | 36.6 | 39.0 | | | 34.2 | 29.7 | 30.1 | | 30.7 | 35.8 | 35.7 | |

| Participant 11 | | | Participant 12 | | | Participant 13 | | | Participant 14 | | | Participant 15 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| | 32.6 | 34.9 | 35.9 | | 38.2 | 31.3 | 33.7 | | | 33.7 | 34.2 | 39.9 | | 43.5 |
| | 35.6 | 35.7 | 37.7 | | 39.6 | 31.6 | 35.0 | | | 32.3 | 35.5 | 41.7 | | 43.3 |
| | 35.4 | 36.5 | 37.4 | | 38.9 | 29.4 | 33.6 | | | 32.2 | 33.0 | 42.4 | | 43.2 |
| | 35.8 | 35.3 | 36.8 | | 40.2 | 30.4 | 33.8 | | | 32.7 | 33.4 | 39.5 | | 44.5 |
| | 34.8 | 34.5 | 38.3 | | 39.5 | 33.7 | 33.3 | | | 32.5 | 33.5 | 40.4 | | 43.5 |

| Participant 16 | | | Participant 17 | | | Participant 18 | | | Participant 19 | | | Participant 20 | | |
|---|---|---|---|---|---|---|---|---|---|---|---|---|---|---|
| S1 | S2 | S3 | S1 | S2 | S3 | S1 | S2 | S3 | S1 | S2 | S3 | S1 | S2 | S3 |
| 25.2 | 24.1 | | | 41.9 | 38.1 | 32.1 | | 43.3 | 41.7 | 42.8 | | | 40.0 | 38.7 |
| 26.9 | 22.9 | | | 41.4 | 37.1 | 31.4 | | 42.4 | 43.9 | 41.2 | | | 40.1 | 36.8 |
| 24.5 | 23.9 | | | 41.0 | 36.0 | 30.0 | | 41.0 | 41.3 | 42.1 | | | 40.1 | 37.9 |
| 24.5 | 21.3 | | | 42.7 | 36.2 | 32.5 | | 39.7 | 42.6 | 43.2 | | | 39.8 | 35.4 |
| 25.2 | 22.9 | | | 40.8 | 38.0 | 33.1 | | 42.0 | 43.1 | 42.7 | | | 39.4 | 38.5 |

The calculated parameters, $\Delta h$ (Equation 1), Hti (Equation 2) and % Hti (Equation 3) are presented in Table 10.

Tables 10 to 10.2 describe the calculated values of $\Delta h$ of the product at a concentration of 2.5%.

TABLE 10

Values of Δh
Δh Values

| Research participant code | Product: concentration of 2.5% ucuuba butter | | | | | Control | | | | |
|---|---|---|---|---|---|---|---|---|---|---|
| | 15 min | 2 h | 4 h | 8 h | 24 h | 15 min | 2 h | 4 h | 8 h | 24 h |
| 01 | 0.68 | 0.9 | 1.4 | 1.2 | −0.4 | 1.7 | 2.4 | 2.2 | 1.4 | −0.2 |
| 02 | 1.66 | 1.9 | 1.8 | 1.6 | 1.3 | 1.9 | 2.8 | 1.4 | 0.5 | −0.9 |
| 03 | 0.10 | −0.6 | −0.8 | −1.0 | 0.1 | 0.2 | −0.2 | −1.0 | −1.2 | 1.9 |
| 04 | −0.04 | −0.9 | −0.9 | −0.9 | −2.0 | −0.7 | −1.3 | −1.6 | −1.9 | −2.2 |
| 05 | 1.98 | 2.3 | 5.0 | 2.2 | 0.8 | 1.0 | 1.8 | 5.1 | 1.9 | 0.4 |
| 06 | 1.82 | 2.0 | 1.5 | 1.0 | 1.0 | 0.3 | −0.1 | −0.5 | −0.8 | −0.1 |
| 07 | −0.96 | −0.9 | −1.6 | −2.2 | −2.1 | −1.5 | −1.6 | −1.3 | −1.6 | −1.4 |
| 08 | −0.90 | −1.1 | −1.1 | −1.5 | −1.6 | −0.2 | −0.7 | −0.5 | −0.6 | 0.0 |
| 09 | −0.90 | −0.4 | −0.2 | −1.1 | −1.2 | −0.2 | −1.0 | −1.1 | −1.6 | −0.9 |
| 10 | −0.76 | −1.4 | −1.9 | −1.7 | −1.1 | −0.8 | −0.8 | −1.1 | −1.8 | −1.2 |
| 11 | 1.74 | −0.1 | −0.2 | −0.9 | −1.6 | 2.9 | 1.0 | 1.1 | 0.4 | −0.6 |
| 12 | 0.02 | −0.7 | 1.1 | −0.4 | −0.4 | −0.8 | −1.7 | −1.2 | −1.4 | −1.7 |
| 13 | 0.02 | −0.5 | −1.3 | −0.7 | −0.5 | −0.2 | −1.1 | −1.3 | −1.6 | −1.8 |
| 14 | −0.56 | −1.0 | −0.3 | −0.5 | −0.6 | 0.2 | −0.1 | −0.3 | 0.2 | 0.5 |
| 15 | 0.12 | −1.1 | −1.0 | −0.7 | −0.4 | −0.7 | −2.3 | −2.3 | −0.4 | 0.0 |
| 16 | −0.35 | −0.4 | −0.8 | −0.9 | −0.8 | −0.4 | −1.3 | −1.8 | −1.6 | −1.8 |
| 17 | 0.04 | −0.5 | −0.7 | −0.9 | −1.1 | −0.1 | −0.7 | −0.8 | −0.8 | −0.8 |
| 18 | −0.32 | 0.2 | 0.3 | −0.6 | −0.8 | −0.8 | −0.3 | 0.0 | −0.1 | 0.6 |
| 19 | 0.06 | −0.1 | −0.4 | 0.0 | −0.6 | −0.2 | −0.7 | −1.4 | −0.6 | −0.4 |
| 20 | 1.74 | 2.5 | 2.2 | 2.4 | 2.2 | 2.0 | 0.4 | 0.8 | 1.4 | 1.4 |

TABLE 10.1

Values of H
H values

| Research participant code | Product: concentration of 2.5% ucuuba butter | | | | |
|---|---|---|---|---|---|
| | 15 min | 2 h | 4 h | 8 h | 24 h |
| 01 | −1.06 | −1.5 | −0.8 | −0.2 | −0.1 |
| 02 | −0.24 | −0.9 | 0.3 | 1.1 | 2.2 |
| 03 | −0.14 | −0.4 | 0.3 | 0.2 | −1.8 |
| 04 | 0.64 | 0.4 | 0.7 | 0.9 | 0.2 |
| 05 | 0.96 | 0.5 | −0.1 | 0.3 | 0.4 |
| 06 | 1.50 | 2.2 | 2.0 | 1.8 | 1.1 |
| 07 | 0.52 | 0.7 | −0.3 | −0.6 | −0.7 |
| 08 | −0.72 | −0.4 | −0.6 | −0.9 | −1.6 |
| 09 | −0.66 | 0.6 | 0.9 | 0.5 | −0.3 |
| 10 | 0.06 | −0.6 | −0.8 | 0.1 | 0.1 |
| 11 | −1.19 | −1.1 | −1.3 | −1.3 | −1.0 |
| 12 | 0.80 | 1.0 | 2.3 | 1.0 | 1.3 |
| 13 | 0.22 | 0.6 | 0.1 | 0.8 | 1.3 |
| 14 | −0.74 | −0.9 | −0.1 | −0.6 | −1.0 |
| 15 | 0.78 | 1.2 | 1.3 | −0.3 | −0.5 |
| 16 | 0.07 | 0.9 | 1.0 | 0.7 | 0.9 |
| 17 | 0.18 | 0.1 | 0.1 | −0.1 | −0.2 |
| 18 | 0.50 | 0.5 | 0.3 | −0.5 | −1.5 |
| 19 | 0.26 | 0.6 | 1.1 | 0.5 | −0.2 |
| 20 | −0.26 | 2.1 | 1.4 | 1.0 | 0.8 |

TABLE 10.2

Values of % H
% H values

| Research participant code | Product: concentration of 2.5% ucuuba butter | | | | |
|---|---|---|---|---|---|
| | 15 min | 2 h | 4 h | 8 h | 24 h |
| 01 | −2.4 | −3.4 | −1.8 | −0.5 | −0.3 |
| 02 | −0.7 | −2.6 | 1.0 | 3.1 | 6.4 |
| 03 | −0.4 | −1.1 | 0.8 | 0.5 | −5.4 |
| 04 | 1.5 | 1.0 | 1.6 | 2.1 | 0.4 |
| 05 | 2.9 | 1.5 | −0.3 | 0.8 | 1.2 |
| 06 | 4.0 | 5.9 | 5.5 | 4.9 | 3.0 |
| 07 | 1.2 | 1.7 | −0.6 | −1.4 | −1.7 |

TABLE 10.2-continued

Values of % H
% H values

| Research participant code | Product: concentration of 2.5% ucuuba butter | | | | |
|---|---|---|---|---|---|
| | 15 min | 2 h | 4 h | 8 h | 24 h |
| 08 | −2.2 | −1.2 | −2.0 | −2.9 | −5.1 |
| 09 | −2.0 | 1.9 | 2.7 | 1.6 | −1.0 |
| 10 | 0.2 | −1.5 | −2.2 | 0.2 | 0.3 |
| 11 | −3.2 | −3.1 | −3.6 | −3.4 | −2.8 |
| 12 | 2.1 | 2.6 | 6.2 | 2.6 | 3.5 |
| 13 | 0.6 | 1.6 | 0.2 | 2.4 | 3.8 |
| 14 | −2.1 | −2.5 | −0.2 | −1.9 | −3.0 |
| 15 | 1.9 | 2.9 | 3.2 | −0.8 | −1.2 |
| 16 | 0.3 | 3.8 | 4.0 | 2.9 | 3.9 |
| 17 | 0.5 | 0.3 | 0.2 | −0.3 | −0.6 |
| 18 | 1.5 | 1.5 | 0.9 | −1.7 | −4.5 |
| 19 | 0.6 | 1.5 | 2.5 | 1.2 | −0.4 |
| 20 | −0.7 | 6.0 | 4.1 | 2.9 | 2.3 |

Figure 2:
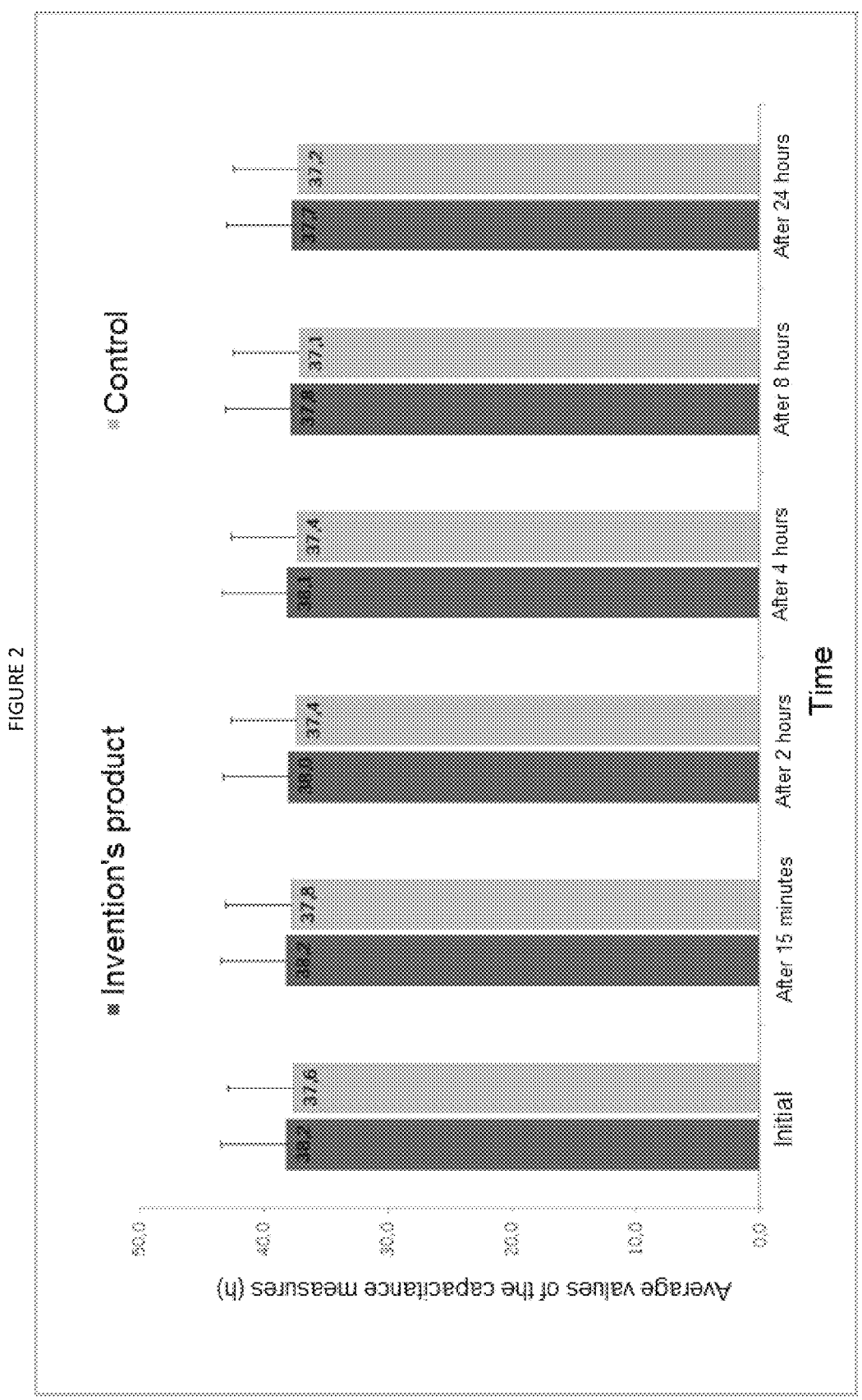
FIG. 2 describes the average values of the capacitance measures (h) obtained for control and after application of the product at the concentration of 1.0% ucuuba.

FIG. 2 shows the average values of capacitance measurements (M) obtained by the control and after application of the product, in all evaluation times.

To assess the significance of skin hydration after application, followed by rinsing of the product, several statistical analyzes were employed, as described below.

Table 11 summarizes the results of the statistical analysis to assess the basal homogeneity between the product application site and the control site. The full data of the statistical analysis are listed in Tables 12 to 12.3.

TABLE 11

Data summarized from the statistical analysis
of basal homogeneity. P Values

| Comparison Group | Parameter: h |
|---|---|
| h Product vs. h Control | 0.0936 (non-significant) |

According to the results obtained, there was no significant difference (P>0.05) between the capacitance basal values obtained for the product application sites and respective control sites, indicating the homogeneity between the sites.

Tables 12 to 12.3 describe the complete data of the statistical analysis of the product at the concentration of 2.5% ucuuba.

TABLE 12

Statistical analysis = basal homogeneity:
Basal Homogeneity

| Paired t-Test | |
|---|---|
| P Value | 0.0936 |
| P value summary | ns |
| Significantly different? (P < 0.05) | No |
| One-tailed or two-tailed P value? | Two-tailed |

TABLE 12-continued

Statistical analysis = basal homogeneity:
Basal Homogeneity

| Paired t-Test | |
|---|---|
| t, df | t = 1.765 df = 19 |
| Number of pairs | 20 |
| How big is the difference? | |
| Difference in means | 1.187 |
| Standard deviation of the differences | 3.007 |
| statistical significance of the difference between means | 0.6725 |
| 95% confidence interval | −0.2205 to 2.594 |
| R squared | 0.1409 |

TABLE 12.1

Significance of the effect
Significance of the effect - product containing a concentration of 1.0% ucuuba butter

| Paired t-Test | Initial vs. After 15 minutes | Initial vs. After 2 hours | Initial vs. After 4 hours | Initial vs. After 8 hours | Initial vs. After 24 hours |
|---|---|---|---|---|---|
| P Value | 0.2589 | 0.9799 | 0.7862 | 0.3345 | 0.0627 |
| Summary of the P value | ns | ns | ns | ns | ns |
| Significantly different? (P < 0.05) | No | No | No | No | No |
| One-tailed or two-tailed P value? | Two-tailed | Two-tailed | Two-tailed | Two-tailed | Two-tailed |
| t, df | t = 1.164 df = 19 | t = 0.02558 df = 19 | t = 0.2752 df = 19 | t = 0.9903 df = 19 | t = 1.977 df = 19 |
| Number of pairs | 20 | 20 | 20 | 20 | 20 |
| How big is the difference? | | | | | |
| Difference in means | 0.259 | 0.007 | 0.101 | −0.284 | −0.491 |
| Standard deviation of the differences | 0.9925 | 1.224 | 1.642 | 1.283 | 1.111 |
| statistical significance of the difference between means | 0.225 | 0.2737 | 0.3671 | 0.2868 | 0.2483 |
| 95% confidence interval | −0.2068 to 0.7248 | −0.5659 to 0.5799 | −0.6673 to 0.8693 | −0.8842 to 0.3162 | −1,011 to 0.02878 |
| R squared | 0.06655 | 0.00003443 | 0.003969 | 0.04908 | 0.1706 |

TABLE 12.2

Control
Significance of the effect - Control

| Paired t-Test | Initial vs. After 15 minutes | Initial vs. After 2 hours | Initial vs. After 4 hours | Initial vs. After 8 hours | Initial vs. After 24 hours |
|---|---|---|---|---|---|
| P Value | 0.4806 | 0.3691 | 0.4647 | 0.0694 | 0.0771 |
| Summary of the P value | ns | ns | ns | ns | ns |
| Significantly different? (P < 0.05) | No | No | No | No | No |
| One-tailed or two-tailed P value? | Two-tailed | Two-tailed | Two-tailed | Two-tailed | Two-tailed |
| t, df | t = 0.7195 df = 19 | t = 0.9201 df = 19 | t = 0.7461 df = 19 | t = 1.925 df = 19 | t = 1.869 df = 19 |
| Number of pairs | 20 | 20 | 20 | 20 | 20 |
| How big is the difference? | | | | | |
| Difference in means | 0.185 | −0.279 | −0.286 | −0.497 | −0.454 |
| Standard deviation of the differences | 1.15 | 1.356 | 1.714 | 1.155 | 1.086 |
| statistical significance of the difference between means | 0.2571 | 0.3032 | 0.3833 | 0.2582 | 0.2429 |

TABLE 12.2-continued

Control
Significance of the effect - Control

| Paired t-Test | Initial vs. After 15 minutes | Initial vs. After 2 hours | Initial vs. After 4 hours | Initial vs. After 8 hours | Initial vs. After 24 hours |
|---|---|---|---|---|---|
| 95% confidence interval | −0.3531 to 0.7231 | −0.9137 to 0.3557 | −1.088 to 0.5163 | −1.038 to 0.04351 | −0.9623 to 0.05434 |
| R squared | 0.02653 | 0.04266 | 0.02846 | 0.1631 | 0.1553 |

TABLE 12.3

Comparison between product and control
Comparison of Product containing 2.5% ucuuba butter Vs. Control

| Paired t-test | Initial vs. After 15 minutes | Initial vs. After 2 hours | Initial vs. After 4 hours | Initial vs. After 8 hours | Initial vs. After 24 hours |
|---|---|---|---|---|---|
| P-value | 0.6239 | 0.2201 | 0.0846 | 0.2144 | 0.9024 |
| P-value summary | ns | ns | ns | ns | ns |
| Significantly different? (P < 0.05) | No | No | No | No | No |
| one- or two-tailed P value? | two-tailed | two-tailed | two-tailed | two-tailed | two-tailed |
| t, df | t = 0.4985 df = 19 | t = 1.268 df = 19 | t = 1.820 df = 19 | t = 1.285 df = 19 | t = 0.1243 df = 19 |
| Number of pairs | 20 | 20 | 20 | 20 | 20 |
| How big is the difference? | | | | | |
| Mean difference | −0.0795 | −0.28 | −0.385 | −0.23 | 0.03 |
| SD of the differences | 0.7132 | 0.9876 | 0.9461 | 0.8007 | 1.08 |
| SEM of the differences | 0.1595 | 0.2208 | 0.2115 | 0.179 | 0.2414 |
| 95% confidence interval | −0.4133 to 0.2543 | −0.7422 to 0.1822 | −0.8278 to 0.05777 | −0.6048 to 0.1448 | −0.4752 to 0.5352 |
| R square | 0.01291 | 0.07801 | 0.1484 | 0.07991 | 0.0008123 |

Table 13 summarizes the results obtained from the statistical analysis of the significance of variations in capacitance values throughout the study for the product and control.

TABLE 13

Summarized data on the statistical analysis of the significance of the changes in the skin barrier. P values.

| Comparison Group | Control | Product: concentration of 2.5% of ucuuba butter |
|---|---|---|
| $h_{t0}$ vs. $h_{t15\,min}$ | 0.4806 (non-significant) | 0.2589 (non-significant) |
| $h_{t0}$ vs. $h_{t2}$ | 0.3691 (non-significant) | <0.9799 (non-significant) |
| $h_{t0}$ vs. $h_{t4}$ | 0.4647 (non-significant) | <0.7862 (non-significant) |
| $h_{t0}$ vs. $h_{t8}$ | 0.0694 (non-significant) | <0.3345 (non-significant) |
| $h_{t0}$ vs. $h_{t24}$ | 0.0771 (non-significant) | <0.0627 (non-significant) |

According to the results obtained:

there was no significant difference (P>0.05) in the h values for the control site after 15 minutes, 2, 4, 8 and 24 hours, indicating that there was no significant change in skin hydration.

for the product containing a concentration of 2.5% ucuuba butter there was no significant difference (P>0.05) in the h values at the product site after 15 minutes, 2, 4, 8 and 24 hours, indicating that there was no significant change in skin hydration.

The results of the statistical analysis for assessment of the significance of skin hydration conferred by the product in the control are summarized in Table 14.

TABLE 14

Summarized data on the statistical analysis of the comparison of Product vs. Control. P values

| Comparison Group | After 15 minutes of application | After 2 hours of application | After 4 hours of application | After 8 hours of application | After 24 hours of application |
|---|---|---|---|---|---|
| $\Delta h_{ti,\,P}$ vs. $\Delta h_{ti,\,C}$ | 0.6239 (non-significant) | 0.2201 (non-significant) | 0.0846 (non-significant) | 0.2144 (non-significant) | 0.9024 (non-significant) |

The skin hydration conferred by the product containing a concentration of 2.5% of ucuuba butter was not significantly (P>0.05) superior after 15 minutes, 2, 4, 8 and 24 hours of application when compared to control. However, it was found that 60%, 65%, 65%, 60% and 45% of study participants showed improvement in skin hydration after 15 minutes, 2, 4, 8 and 24 hours of application, respectively.

6. Conclusion

According to the protocol for study and procedures used for the evaluation of skin hydration, it was found that the application, followed by rinsing, of the product at a concentration of 2.5% ucuuba butter on the skin in the forearm region:
- maintained the natural skin hydration after 15 minutes, 2, 4, 8 and 24 hours of application.
- did not confer significantly superior hydration compared to the control (no product applied to the skin); however, 65% of study participants showed improvement in skin hydration after applying the product.

Test 3—Evaluation of Skin Hydration by Corneometry after Rinsing the Product Applied at a Concentration of 5.0% Ucuuba 1. Objective To evaluate the level of skin hydration after application of the formulation in Table L above.

2. Volunteers Panel

Volunteers participating in the study were instructed to discontinue use of any topical products in the area of the forearms 48 hours before the study began. Participant volunteers remained in the laboratory for measurements after 15 minutes, 2, 4 and 8 hours. Prior to the first measurement, after application, the product containing the formulation of Table L was rinsed in running water for 30 seconds.

3. Procedures for Conducting Evaluations 3.1. General Overview

On the left or right volar surface of the forearm of a study participant two areas measuring 2.5 cm×4.0 cm, named sites, were marked. The determination of the control site (no product applied) and of the application site was randomized between delimited sites, as recorded in the correlation worksheet in Table 15 below.

TABLE 15

| Research participant number | Age | Photo-type | Application Sites | |
|---|---|---|---|---|
| | | | Site 1 | Site 2 |
| 01 | 55 | IV | Control | Product: concentration of 5.0% of ucuuba butter |
| 02 | 59 | IV | Product: concentration of 5.0% of ucuuba butter | Control |
| 03 | 58 | IV | Control | Product: concentration of 5.0% of ucuuba butter |
| 04 | 44 | IV | Product: concentration of 5.0% of ucuuba butter | Control |
| 05 | 52 | IV | Control | Product: concentration of 5.0% of ucuuba butter |
| 06 | 35 | IV | Product: concentration of 5.0% of ucuuba butter | Control |
| 07 | 34 | IV | Control | Product: concentration of 5.0% of ucuuba butter |
| 08 | 58 | IV | Product: concentration of 5.0% of ucuuba butter | Control |
| 09 | 42 | IV | Control | Product: concentration of 5.0% of ucuuba butter |
| 10 | 31 | III | Product: concentration of 5.0% of ucuuba butter | Control |
| 11 | 23 | III | Control | Product: concentration of 5.0% of ucuuba butter |
| 12 | 29 | IV | Product: concentration of 5.0% of ucuuba butter | Control |

After 30 minutes of acclimatization in controlled environment at a 20±2° C. temperature and 50±5% relative humidity, the basal measurements (prior to application of the product) of skin capacitance were obtained in the delimited sites. Then, an amount of 20 μL of the product was applied, massaging it homogeneously on the site with the aid of a disposable finger stall.

After application, study participants remained in the laboratory for the capacitance measurements after 15 minutes, 2, 4, 8 and 24 hours.

Throughout the experiment in the laboratory, the climate conditions were kept constant according to the aforementioned ranges.

3.2. Application and Rinsing of the Product

The same aspects of TEST 1 apply to TEST 2.

3.3. Capacitance Measurement Acquisition

The same aspects of TEST 1 apply to TEST 2.

4. Data Analysis and Interpretation 4.1. Software for Obtaining the Average Values and Data Analysis:

The same aspects of TEST 1 apply to TEST 2.

4.2. Software for Statistical Analysis:

The same aspects of TEST 1 apply to TEST 2.

4.3. Interpretation of Results

The same aspects of TEST 1 apply to TEST 2.

4.3.1. Calculations

From the capacitance values (h) the difference in skin hydration ($\Delta h$) was calculated, i.e., the variation of capacitance measurements at each evaluation time in relation to basal measurements. The parameter $\Delta h$ was calculated for the product and control, according to Equation 1.

$$\Delta h = h_{ti} - h_{t0}$$

Equation 1. Difference in skin hydration at each evaluation time in relation to basal measurements. Wherein: $\Delta h$=hydration difference, $h_{ti}$=average capacitance measurements obtained after i hours of study (i=15 minutes, 2, 4 e 8 hours); $h_{t0}$=average capacitance measurements at baseline (basal).

From the hydration difference values (Δh) the hydration parameters (H) and the percentage of skin hydration (% H) provided by the product were calculated, according to Equations 2 and 3.

$$Hti = \Delta hti(\text{product}) - \Delta hti(\text{control})$$

Equation 2. Calculation of the skin hydration provided by the application of the product. Wherein: $H_{ti}$=skin hydration after i hours of the application of the product; $\Delta h_{ti}$ (control) and $\Delta h_{ti}$ (product)=skin hydration differences obtained for the control and product, respectively.

$$\% Hti = (Hti \times 100)/ht0$$

Equation 3. Calculation of the percentage of skin hydration provided by the application of the product. Wherein:
% $H_{ti}$=percentage of hydration, $H_{ti}$=skin hydration after i hours of the application of the product; $h_{t0}$=average capacitance measurements at baseline (basal).

4.3.2. Statistical Evaluations
4.3.2.1. Basal Homogeneity
The same aspects of TEST 1 apply to TEST 2.
4.3.2.2. Significance of the Effect
The significance of the variation in skin hydration at each assessment time, both for control and product, was assessed by employing the paired, bimodal Student's t-Test method, in which a 95% confidence interval was considered, to the basal capacitance values (ht0) in relation to the values obtained after i hours of the application (hti); i=15 minutes, 2, 4 and 8 hours.

Satisfactory results are achieved when, concerning control, there is no statistically significant difference between ht0 and hti ($P>0.05$) and, concerning product, hti is significantly superior to ht0 ($P<0.05$), evincing an increase in skin hydration.

4.3.2.3. Comparison Between Product and Control
The same aspects of TEST 1 apply to TEST 2.
5. Results and Discussions:
5.1. Statistics on the Participation of Volunteers
Total contacted volunteers: 70;
Total contacted volunteers: 16;
Table of volunteers: 4;
Total volunteers dismissed after evaluation of inclusion and exclusion criteria: 0;
Effectively included volunteers: 12;
Volunteers who completed the study: 12.
5.2. General Data on the Study Group
Average age: 43±13 years.
Phototype (Fitzpatrick): 17% phototype III and 83% phototype IV.
5.3. Climate Control
Statistical data on the environmental monitoring in the waiting and climatization room of the Volunteers during the days of the study was carried out:
Day 1
Temperature: (20.8±0.3° C. (95% confidence interval: 20.7° C. to 21.0° C.)
Relative air humidity: (49±1° C. (95% confidence interval: 48% to 49%)
According to the data recorded on the climate control, temperature and humidity in the waiting and acclimatization room of the participants remained within the range established in the study protocol.
5.4. Results Obtained from the Evaluation
Skin hydration was assessed through capacitance measurements. Tables 16 to 16.4 list all measurements.

Tables 16 to 16.4 describe the capacitance values measured of the product at a concentration of 5.0% ucuuba.

TABLE 16

Initial h average values

| Research participant number | Control | Product: concentration of 5.0% of ucuuba butter |
|---|---|---|
| 01 | 36.58 | 34.94 |
| 02 | 33.94 | 38.50 |
| 03 | 37.36 | 38.84 |
| 04 | 43.50 | 40.92 |
| 05 | 36.18 | 39.40 |
| 06 | 33.10 | 31.48 |
| 07 | 35.74 | 34.0 |
| 08 | 35.90 | 37.72 |
| 09 | 32.40 | 32.48 |
| 10 | 35.20 | 39.98 |
| 11 | 35.68 | 37.52 |
| 12 | 28.66 | 33.42 |

TABLE 16.1

After 15 minutes h average values

| Research participant number | Control | Product: concentration of 5.0% of ucuuba butter |
|---|---|---|
| 01 | 37.88 | 41.02 |
| 02 | 32.14 | 37.28 |
| 03 | 34.96 | 41.22 |
| 04 | 42.30 | 41.14 |
| 05 | 36.44 | 40.78 |
| 06 | 33.94 | 33.94 |
| 07 | 36.76 | 37.44 |
| 08 | 34.92 | 42.64 |
| 09 | 31.60 | 33.70 |
| 10 | 32.44 | 41.16 |
| 11 | 31.76 | 37.22 |
| 12 | 26.98 | 33.54 |

TABLE 16.2

After 2 hours h average values

| Research participant number | Control | Product: concentration of 5.0% of ucuuba butter |
|---|---|---|
| 01 | 42.46 | 41.54 |
| 02 | 34.44 | 41.14 |
| 03 | 38.32 | 41.98 |
| 04 | 40.12 | 42.66 |
| 05 | 37.30 | 42.68 |
| 06 | 35.68 | 37.94 |
| 07 | 29.36 | 30.16 |
| 08 | 36.34 | 43.82 |
| 09 | 31.96 | 36.04 |
| 10 | 32.62 | 38.84 |
| 11 | 30.26 | 36.50 |
| 12 | 29.26 | 35.84 |

TABLE 16.3

After 4 hours h average values

| Research participant number | Control | Product: concentration of 5.0% of ucuuba butter |
|---|---|---|
| 01 | 36.66 | 36.40 |
| 02 | 39.30 | 43.46 |
| 03 | 36.74 | 44.70 |
| 04 | 39.44 | 42.74 |

TABLE 16.3-continued

After 4 hours
h average values

| Research participant number | Control | Product: concentration of 5.0% of ucuuba butter |
|---|---|---|
| 05 | 38.30 | 43.02 |
| 06 | 36.86 | 37.42 |
| 07 | 33.74 | 35.72 |
| 08 | 33.78 | 42.50 |
| 09 | 32.24 | 31.84 |
| 10 | 33.66 | 40.58 |
| 11 | 32.00 | 37.02 |
| 12 | 33.62 | 41.16 |

TABLE 16.4

After 8 hours
h average values

| Research participant number | Control | Product: concentration of 5.0% of ucuuba butter |
|---|---|---|
| 01 | 36.46 | 37.68 |
| 02 | 33.98 | 39.60 |
| 03 | 41.00 | 49.74 |
| 04 | 42.92 | 42.52 |
| 05 | 38.76 | 45.38 |
| 06 | 36.98 | 33.74 |
| 07 | 31.74 | 33.40 |
| 08 | 34.38 | 39.14 |
| 09 | 31.62 | 32.44 |
| 10 | 36.78 | 42.36 |
| 11 | 32.64 | 35.36 |
| 12 | 31.18 | 39.64 |

The calculated parameters, Δh (Equation 1), Hti (Equation 2) and % Hti (Equation 3) are presented in Tables 17 to 17.2.

Tables 17 to 17.2 describe the Δh calculated values of the product at a concentration of 5.0% ucuuba.

TABLE 17

Δh values

| Research participant number | Product: concentration of 5.0% of ucuuba butter | | | | Control | | | |
|---|---|---|---|---|---|---|---|---|
| | 15 min | 2 h | 4 h | 8 h | 15 min | 2 s | 4 h | 8 h |
| 01 | 6.1 | 6.6 | 1.5 | 2.7 | 1.3 | 5.9 | 0.1 | −0.1 |
| 02 | −1.2 | 2.6 | 5.0 | 1.1 | −1.8 | 0.5 | 5.4 | 0.0 |
| 03 | 2.4 | 3.1 | 5.9 | 10.9 | −2.4 | 1.0 | −0.6 | 3.6 |
| 04 | 0.2 | 1.7 | 1.8 | 1.6 | −1.2 | −3.4 | −4.1 | −0.6 |
| 05 | 1.4 | 3.3 | 3.6 | 6.0 | 0.3 | 1.1 | 2.1 | 2.6 |
| 06 | 2.5 | 6.5 | 5.9 | 2.3 | 0.8 | 2.6 | 3.8 | 3.9 |
| 07 | 3.4 | −3.8 | 1.7 | −0.6 | 1.0 | −6.4 | −2.0 | −4.0 |
| 08 | 4.9 | 6.1 | 4.8 | 1.4 | −1.0 | 0.4 | −2.1 | −1.5 |
| 09 | 1.2 | 3.6 | −0.6 | 0.0 | −0.8 | −0.4 | −0.2 | −0.8 |
| 10 | 1.2 | −1.1 | −0.6 | 2.4 | −2.8 | −2.6 | −1.5 | 1.6 |
| 11 | −0.3 | −1.0 | −0.5 | −2.2 | −3.9 | −5.4 | −3.7 | −3.0 |
| 12 | 0.1 | 2.4 | 7.7 | 6.2 | −1.7 | 0.6 | 5.0 | 2.5 |

TABLE 17.1

H values

| Research participant number | Product: concentration of 5.0% of ucuuba butter | | | |
|---|---|---|---|---|
| | 15 min | 2 h | 4 h | 8 h |
| 01 | 4.8 | 0.7 | 1.4 | 2.9 |
| 02 | 0.6 | 2.1 | −0.4 | 1.1 |
| 03 | 4.8 | 2.2 | 6.5 | 7.3 |
| 04 | 1.4 | 5.1 | 5.9 | 2.2 |
| 05 | 1.1 | 2.2 | 1.5 | 3.4 |
| 06 | 1.6 | 3.9 | 2.2 | −1.6 |
| 07 | 2.4 | 2.5 | 3.7 | 3.4 |
| 08 | 5.9 | 5.7 | 6.9 | 2.9 |
| 09 | 2.0 | 4.0 | −0.5 | 0.7 |
| 10 | 3.9 | 1.4 | 2.1 | 0.8 |
| 11 | 3.6 | 4.4 | 3.2 | 0.9 |
| 12 | 1.8 | 1.8 | 2.8 | 3.7 |

TABLE 17.2

% H values

| Research participant number | Product: concentration of 5.0% of ucuuba butter | | | |
|---|---|---|---|---|
| | 15 min | 2 h | 4 h | 8 h |
| 01 | 13.7 | 2.1 | 3.9 | 8.2 |
| 02 | 1.5 | 5.6 | −1.0 | 2.8 |
| 03 | 12.3 | 5.6 | 16.7 | 18.7 |
| 04 | 3.5 | 12.5 | 14.4 | 5.3 |
| 05 | 2.8 | 5.5 | 3.8 | 8.6 |
| 06 | 5.1 | 12.3 | 6.9 | −5.1 |
| 07 | 7.1 | 7.5 | 10.9 | 10.0 |
| 08 | 15.6 | 15.0 | 18.3 | 7.8 |
| 09 | 6.2 | 12.3 | −1.5 | 2.3 |
| 10 | 9.9 | 3.6 | 5.4 | 2.0 |
| 11 | 9.6 | 11.7 | 8.5 | 2.3 |
| 12 | 5.4 | 5.4 | 8.3 | 11.1 |

Figure 3:
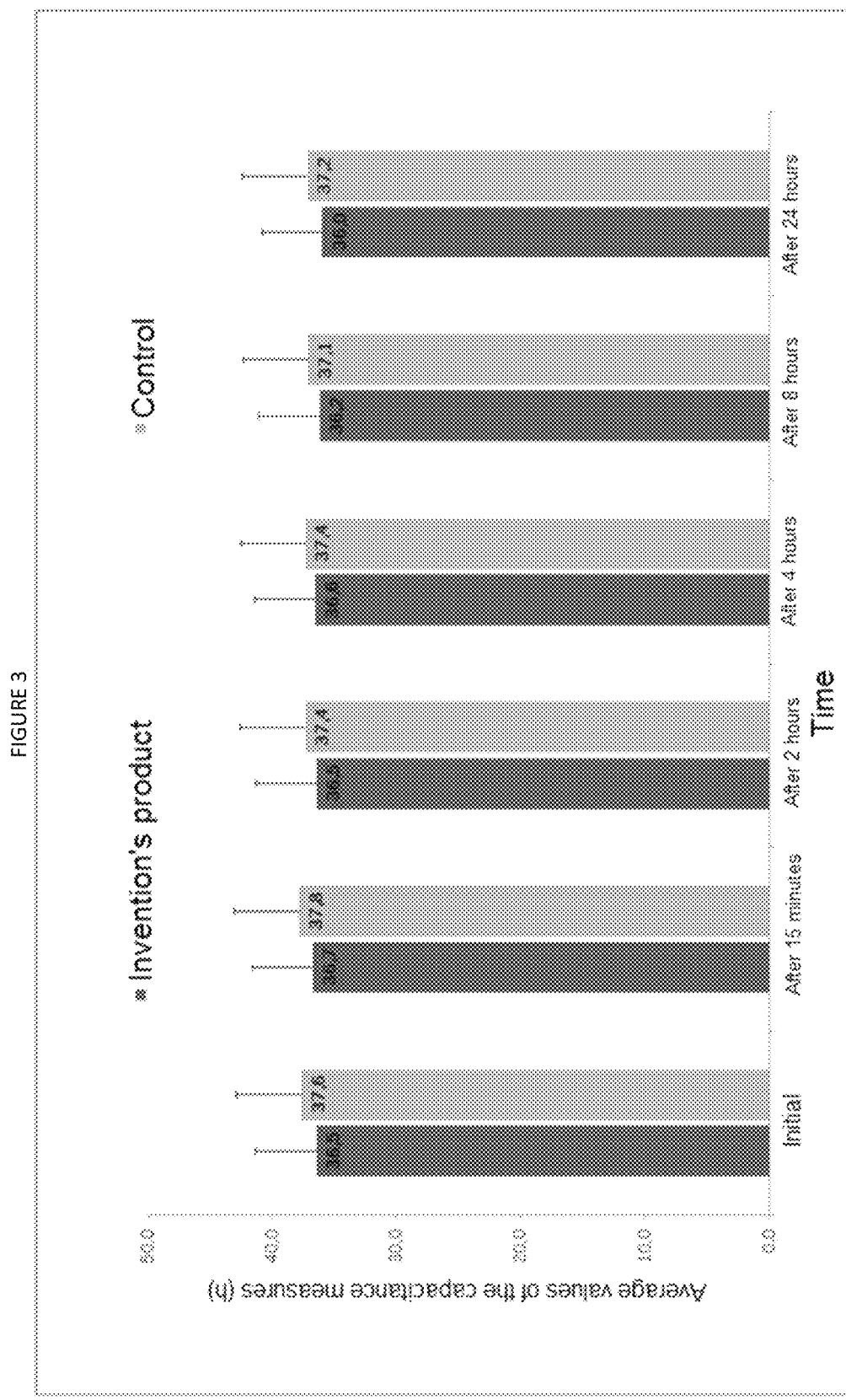
FIG. 3 describes the average values of the capacitance measures (h) obtained for control and after application of the product at the concentration of 2.5% ucuuba.
Figure 4:
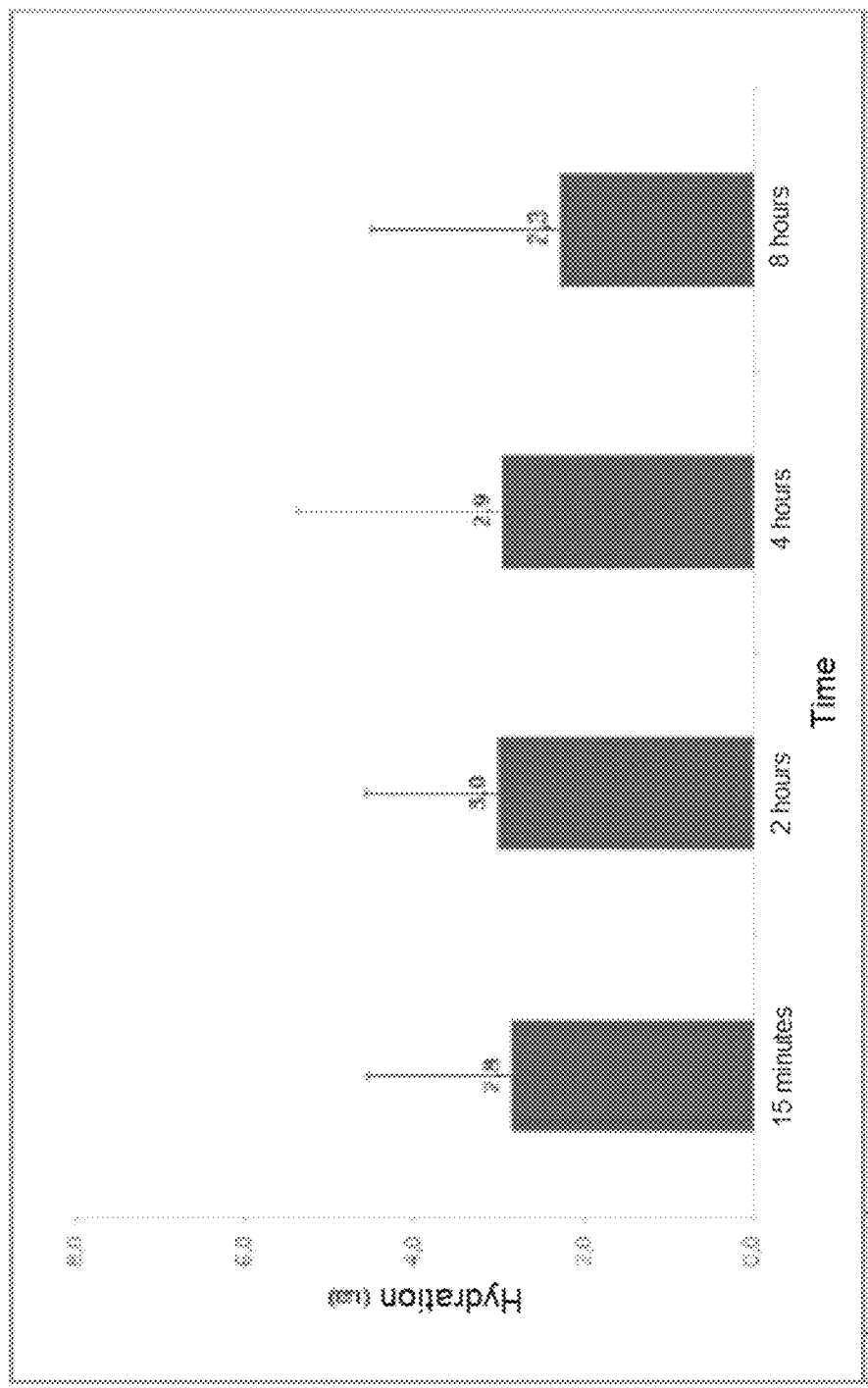
FIGS. 4 and 5 describe the average hydration values and the percentage of hydration of the skin after application of the product at the concentration of 5.0% ucuuba.
Figure 5:
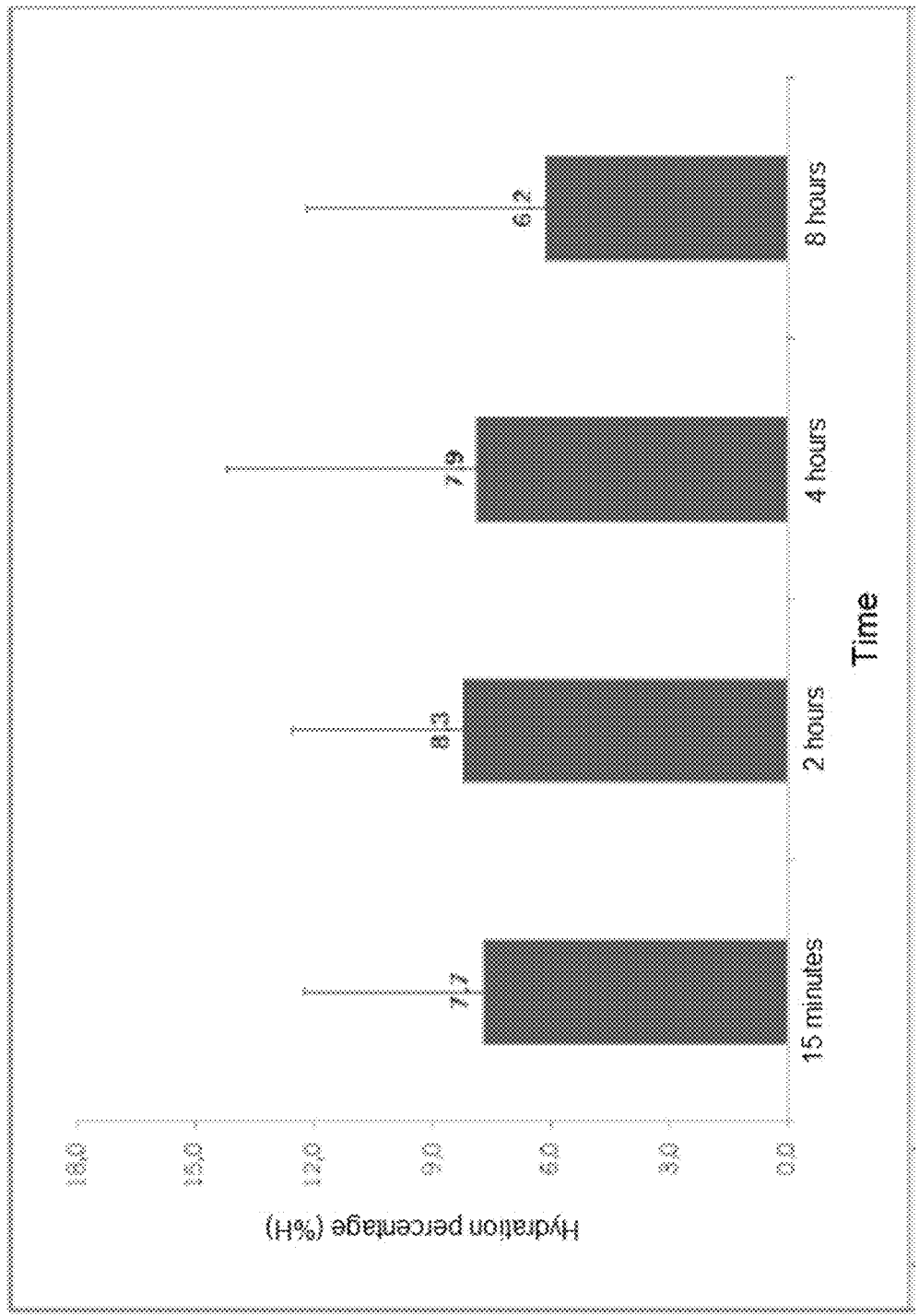

FIGS. 3 and 4 show the mean values of skin hydration measurements (Hti) and skin hydration percentage (% Hti) after application of the product, compared to the control.

To assess the significance of skin hydration after application, followed by rinsing the product, various statistical analysis were employed, as described below.

Table 18 summarizes the results of the statistical analysis to assess basal homogeneity between the product application sites and the control sites. The complete data on the statistical analysis are listed in Tables 19 to 19.3.

TABLE 18

Data summarized from the statistical analysis of the basal homogeneity P values.

| Comparison Group | Parameter: h |
|---|---|
| h Product vs. h Control | 0.1418 (non-significant) |

According to the results, there was no significant difference (P>) between the basal capacitance values obtained for the product application sites and the respective control, indicating homogeneity between sites.

TABLE 19 statistical analysis = basal homogeneity: Basal homogeneity

| Paired t-test | |
|---|---|
| P-value | 0.418 |
| P-value summary | ns |
| Significantly different? (P < 0.05) | No |
| one- or two-tailed P value? | two-tailed |
| t, df | t = 1.583<br>df = 11 |
| Number of pairs | 12 |
| How big is the difference? | |
| Mean difference | 1.247 |
| SD of the differences | 2.729 |
| SEM of the differences | 0.7877 |
| 95% confidence interval | −0.4752 to 2.980 |
| R square | 0.1855 |

TABLE 19.1

Significance of the effect of the product containing a concentration of 5.0% of ucuuba butter
Significance of the Effect - Product: concentration of 5.0% of ucuuba butter

| Paired t-test | Initial vs. After 15 minutes | Initial vs. After 2 hours | Initial vs. After 4 hours | Initial vs. After 8 hours |
|---|---|---|---|---|
| P-value | 0.0138 | 0.0212 | 0.0024 | 0.3345 |
| P-value summary | * | * | ** | * |
| Significantly different? (P < 0.05) | Yes | Yes | Yes | Yes |
| one- or two-tailed P value? | two-tailed | two-tailed | two-tailed | two-tailed |
| t, df | t = 2.926<br>df = 11 | t = 2.684<br>df = 11 | t = 3.922<br>df = 11 | t = 2.591<br>df = 2 |
| Number of pairs | 12 | 12 | 12 | 2 |
| How big is the difference? | | | | |
| Mean difference | 1.823 | 2.495 | 3.113 | 2.650 |
| SD of the differences | 2.159 | 3.220 | 2.750 | 3.543 |
| SEM of the differences | 0.6231 | 0.9295 | 0.7939 | 1.023 |
| 95% confidence interval | 0.4519 to 3.195 | 0.4493 to 4.541 | 1.366 to 4.861 | 0.3989 to 4.901 |
| R square | 0.4377 | 0.3958 | 0.5830 | 0.3790 |

TABLE 19.2

Significance of the Effect: Control
Significance of the Effect - Control

| Paired t-test | Initial vs. After 15 minutes | Initial vs. After 2 hours | Initial vs. After 4 hours | Initial vs. After 8 hours |
|---|---|---|---|---|
| P-value | 0.0546 | 0.6167 | 0.8534 | 0.6422 |
| P-value summary | ns | ns | ns | ns |
| Significantly different? (P < 0.05) | No | No | No | No |
| one- or two-tailed P value? | two-tailed | two-tailed | two-tailed | two-tailed |
| t, df | t = 2.151<br>df = 11 | t = 0.5150<br>df = 11 | t = 0.1892<br>df = 11 | t = 0.4777<br>df = 11 |
| Number of pairs | 12 | 12 | 12 | 2 |
| How big is the difference? | | | | |
| Mean difference | −1.010 | −0.5100 | 0.1750 | 0.3500 |
| SD of the differences | 1.627 | 3.430 | 3.204 | 2.538 |
| SEM of the differences | 0.4696 | 0.9903 | 0.9248 | 0.7326 |
| 95% confidence interval | −2.044 to 0.02357 | −2.690 to 1.670 | −1.861 to 2.211 | −1.262 to 1.962 |
| R square | 0.2960 | 0.02354 | 0.003244 | 0.02033 |

TABLE 19.3

Comparison of the product containing a concentration of 5.0% of ucuuba butter Vs. Control
Comparison of the product containing 5.0% ucuuba butter Vs. Control

| Paired t-test | 15 minutes | 2 hours | 4 hours | 8 hours |
|---|---|---|---|---|
| P-value | 0.0001 | <0.0001 | 0.0016 | 0.0041 |
| P-value summary | *** | **** | ** | ** |
| Significantly different? (P < 0.05) | Yes | Yes | Yes | Yes |
| one- or two-tailed P value? | two-tailed | two-tailed | two-tailed | two-tailed |
| t, df | t = 5.738<br>df = 11 | t = 6.668<br>df = 11 | t = 4.149<br>df = 11 | t = 3.616<br>df = 11 |
| Number of pairs | 12 | 12 | 12 | 12 |
| How big is the difference? | | | | |
| Mean difference | −0.2842 | −3.008 | −2.933 | −2.300 |
| SD of the differences | 1.715 | 1.563 | 2.449 | 2.203 |
| SEM of the differences | 0.4952 | 0.4512 | 0.7070 | 0.6360 |
| 95% confidence interval | −3.932 to −1.752 | −4.001 to −2.015 | −4.489 to −1.377 | −3.700 to −0.9001 |
| R square | 0.7596 | 0.8017 | 0.6101 | 0.5431 |

Table 20 summarizes the results obtained from the statistical analysis of the significance of variations in capacitance values throughout the study for the product and control.

TABLE 20

Summarized data on the statistical analysis of the significance of skin hydration. P values.

| Comparison Group | Control | Product: concentration of 5.0% of ucuuba butter |
|---|---|---|
| $h_{t0}$ vs. $h_{t15\,min}$ | 0.0546 (non-significant) | 0.0138 (significant) |
| $h_{t0}$ vs. $h_{t2}$ | 0.6167 (non-significant) | <0.0212 (significant) |
| $h_{t0}$ vs. $h_{t4}$ | 0.8534 (non-significant) | <0.0024 (significant) |
| $h_{t0}$ vs. $h_{t8}$ | 0.6422 (non-significant) | <0.0251 (significant) |

According to the results obtained:
there was no significant difference (P>0.05) in the h values for the control site after 15 minutes, 2, 4 and 8 hours, indicating that there was no significant change in skin hydration.
for the product containing a concentration of 5.0% ucuuba butter there was no significant difference (P>0.05) in the h values after 15 minutes, 2, 4 and 8 hours of application, indicating that the use of this product provided skin hydration.

The results of the statistical analysis for assessment of the significance of skin hydration conferred by the product in the control are summarized in Table 21.

TABLE 21

Summarized data on the statistical analysis of the comparison of Product vs. Control. P values

| Comparison Group | After 15 min. application | After 2 hours application | After 4 hours application | After 8 hours application |
|---|---|---|---|---|
| $\Delta h_{ti,\ P}$ vs. $\Delta h_{ti,\ C}$ | 0.0001 (significant) | <0.0001 (significant) | 0.0016 (significant) | 0.0041 (significant) |

The skin hydration conferred by the product containing a concentration of 5.0% ucuuba butter was significantly ($P<0.05$) superior after 15 minutes, 2, 4 and 8 hours of application when compared to control.

It was also observed that 100% of study participants showed improvement in skin hydration after 15 minutes and 2 hours, 83% after 4 hours and 92% after 8 hours of application.

6. Conclusion

According to the protocol for study and procedures used for the evaluation of skin hydration, it was found that the application, followed by rinsing, of the product containing a concentration of 5.0% ucuuba butter on the skin in the forearm region:

conferred significantly higher hydration compared to the control (no product applied to the skin). showed that the product containing a concentration of 5.0% ucuuba butter hydrated the skin.

kept skin hydrated for 8 hours after application.

increased the level of skin hydration up to 8.3%.

100% of the study participants showed improvement in skin hydration after applying the product.

Moreover, below is presented the final report of the open, randomized, controlled clinical trial of the skin hydration power (corneometry) of the topical product according to the present invention.

Open, Randomized, Controlled Clinical Trial Report on Skin Hydrating Power (Corneometry) of a Topical Application Product According to the Present Invention 1. Introduction The skin isolates the internal medium from the environment and plays an important role in maintaining homeostasis. Its protective function depends on the integrity and hydration status of the stratum corneum. In the absence thereof, water loss through the skin would rise from 200-400 ml to 9 liters in a period of 24 hours.

The presence of water in the stratum corneum is crucial to maintaining their physical properties of flexibility and elasticity. Water acts as a plasticizer in combination with proteins and soluble materials (BLANK, 1952. 1976).

The water in the stratum corneum comes from the lower layers of the epidermis and dermis, hydrates the cellular environment of the epidermis at the surface to the atmosphere. This is called transepidermal water loss (Transepidermal Water Loss—TEWL).

The state of hydration of the stratum corneum varies depending on the following factors: amount of water, water transport from the lower layers, evaporation rate, speed and amount of keratinization and composition of the epicutaneous emulsion. The water retention capacity of the stratum corneum depends mainly on the presence of the Natural Moisturizing Factor—NMF, a set of hygroscopic substances and lipids, which make the corneal layer impermeable to water (SPENCER, 1988).

Xeroderma or dry skin, which clinically manifests as clouding, flaking, itching and skin tightness, is a condition characterized by loss of stratum corneum barrier function as evidenced by an increase in transepidermal water loss rate. This leads to loss of elasticity and changes in biomechanical properties (CLAR, 1994).

Two main factors may be involved: keratinization disorders and decrease in the water content of the stratum corneum to below 10%. This reduction occurs by the imbalance between evaporation and replenishment of water by the lower layers.

The transepidermal water loss can be altered by environmental factors, body temperature, natural moisturizing factors and using topical products (GALL & CHAPPUIS, 1994).

A cosmiatric treatment for xeroderma to establish the degree of hydration of the stratum corneum:

increasing its water content;

maintaining this water content;

reducing evaporation.

From a therapeutic point of view, the hydration of the stratum corneum increases considerably the skin permeability promoting the percutaneous absorption of the active principles (WESTER & MAIBACH, 1985).

The moisture increase can be accomplished with the use of topical products that act through two main mechanisms:

a. occlusion (promoted by lipid ingredients);

b. "hydrating active" ingredients offered by hygroscopicity, such as NMF constituents, for example (NICHOLLS, 1978; KLIGMAN, 1982; PRALL, 1986 VILAPLANA & COL 1992 KORSTANJE & COL., 1992).

The bioengineered skin or skin Biometrics is the study of biological, mechanical and functional characteristics of the skin by careful measurement of specific variables for scientific and non-invasive methods (RODRIGUES, 1996). The main parameters which can be used to evaluate the effectiveness of a product on the skin are the morphological changes of the skin surface hydration of the stratum corneum and sebum secretion. Because of the variation in parameters between different anatomical regions in a same individual and from different individuals, these techniques are used to measure comparatively variations in a parameter, in the same location before and after use of a product (GALL & CHAPPUIS, 1994).

In the analysis of skin hydration, the most commonly used methods are corneometry and measurement of transepidermal water loss. The measurement of Transepidermal Water Loss—TEWL determines the flow of water evaporation through the stratum corneum in order to evaluate its barrier function, as well as monitor the effects of topical products, especially those with occlusive effect in recovery or reinforcement (HARLOP & PROTTEY, 1976; Leveque & COL, 1979; SPENCER, 1990).

The measurement of dermal electrical capacity (corneometry) is based on the principle of electrical conductivity. The alternating current passing through the integument low frequency depends on the water content of the stratum corneum and its integrity. Through this electric property of the skin can indirectly measure skin hydration (LÉVÊQUE, 1980, TAGAMI & COL., 1980).

The tested cosmetic product is a soap according to the present invention.

2. Objective

The aim of this study was to evaluate the power of skin hydration product of the present invention through instrumental measurements of electrical capacitance.

3. Investigational Product 3.1. Identification

| PRODUCT |
|---|
| BODY MOISTURIZER |

3.2. Application of the Product

The product tested was applied with the aid of a pipettor in the amount of 20 μL in the delimited region of each participant as described in item 7.4.2.

3.3. Storage

The products supplied were initially stored in the sample room of the research center with controlled temperature and restricted access. The release of the products was controlled by the main researcher or designated responsible technicians.

4. Applicable Ethical Considerations

The study was conducted in accordance with the principles of the Declaration of Helsinki, the applicable regulatory requests, including CNS Resolution No. 466/2012, and the Good Clinical Practice (Document of the Americas and ICH E6: Good Clinical Practice).

Before the study, the protocol and the Free, Prior, and Informed Consent (FPIC) Term were submitted to the Research Ethics Committee (CEP) that investigates research institutes for approval in writing. Any written information provided to the research participant and all notifications and the amendments of the research were submitted to the CEP. The substantiated opinion issued by the CEP was filed was filed with the documentation kept by the research center.

Participants were informed of the purpose of the study, its methodology and duration, and possibly expected benefits and restrictions related to the study and those who confirmed their interest in participating signed a Free, Prior, and Informed Consent.

5. Study Period

The total length of the study was 03 days.
Start: Jul. 15, 2014
End: Jul. 17, 2014

6. Survey Participants 6.1. Recruitment of the Research Participants

The research participants were recruited by the recruitment sector of the Research Center, which has a computerized and updated registration system. In this system are registered the participants interested in participating in the research, which were contacted to participate in the selection and which, having met the necessary criteria, were included in the study.

6.2. Selection and Admission of the Research Participants

During the selection of participants for this research, the physician in charge made sure that participants did not have pathologies that could interfere with the results of the study. The physician is also responsible for the information contained in the participant's evaluation form, checking all inclusion and exclusion criteria for the participant's admission in the research.

6.3. Description of the Population

For this study, there were recruited 22 research participants.

The study began with 22 female participants aged between 34 and 60 (average of 49 years).

6.4. Inclusion Criteria

Gender: female;
Age group: 18 to 60 years;
Phototype (Fitzpatrick): I to IV;
Intact skin in the test region;
User of cosmetic products of the same category.

6.5. Exclusion Criteria

Skin marks in the experimental area which are likely to interfere with the study evaluations (pigmentation disorders, vascular malformations, scars, increased hairiness, freckles and warts aplenty, sunburns);
Active dermatoses (local or widespread) that might affect the results of the study;
Pregnant women or nursing mothers;
Atopy history;
History of pathologies aggravated or triggered by ultraviolet radiation;
History of intense allergic reactions, irritations or sensations of discomfort to topic products: Cosmetics or medicaments and also to latex;
Participants with immunodeficiencies;
Intense sun exposure or tanning session up to 15 days before the initial evaluation;
Intended intense sun exposure or tanning session during the study period;
Beauty or facial dermatological treatment up to 4 weeks prior to selection, such as: mesotherapy, sclerotherapy, carboxytherapy and body peelings;
Use of the following topic or systemic medicaments: immunosuppressants, antihistamines, nonsteroidal anti-inflammatory drugs and corticoids up to 2 weeks prior to selection;
Oral or topic treatment with acid vitamin A and/or derivatives thereof up to 1 month prior the start of the study;
Intention of vaccination during the study period or up to 3 weeks prior to the study;
Participation in another study;
Any condition which, in the opinion of the researcher, might compromise the evaluation of the study;
History of non-acceding or unwillingness to accede to the study protocol;
Professionals directly involved in the making of the present protocol and their families.

6.6. Prohibition and Restriction

Allowed:
Bath until 20:00 h of the day prior to the research.
Not Allowed:
Smoking during the research period;
Leave the acclimatized room during implementation of the measurements;
Requirements During the Study Period that Starts 48 h Prior to the Day of Product Application:
Do not apply any other product in the experimental area;
Do not change cosmetic habits, including hygiene;
Do not perform exfoliation or other aesthetic treatments;
Do not be exposed to prolonged intense sunlight and do not undergo artificial tanning in tanning beds;
Do not change dietary habits;
Do not change the hormonal treatment;
Do not change the medical contraceptive method;
Do not use medication described in the exclusion criteria.

7. Methodology
  7.1. Design of the Study
  An open, randomized and controlled clinical study.
  7.2. Materials and Equipments
  Pen for marking;
  Corneometer CM 825 (Courage+Khazaka electronic GmbH);
  Air conditioner;
  Latex gloves and finger cots;
  A 10 $cm^2$ mold;
  Nozzles;
  Pipettor;
  Thermohigrometer.
  7.3. Studied Area
  The product was applied to the participant's forearms.
  7.4. Corneometry Measurements
  The measurements were made by using the equipment Corneometer CM 825, Courage+Khazaka electronic GmbH by means of a measuring probe.

The readings were made by applying the probe in the test area with the pressure allowed by the spring (3.5 N). There were made ten measurements in each area.

The reading indicated the degree of moisture on the skin surface based on electric capacitance variations. The equipment scale is arbitrary, wherein higher reading values indicate a greater hydration.

7.4.1. First Step
  The participants remained at rest in an acclimatized room at a temperature of 20±2° C. and relative air humidity of 50%±5 for at least 30 minutes prior to each reading.

Two symmetric areas of 10 $cm^2$ were marked in the anterior region of the forearms, randomly distributed. One area was used for product application and one area was maintained as control (area without treatment).

The electric capacitance of said regions was determined by using the arithmetic mean of ten measurements (T0).

7.4.2. Second Step
  The tested product was applied in the amount of 20 µl on the marked area of each participant (10 $cm^2$ area).

The product was spread on the skin with the help of a latex finger cot, with soft and circular motions until the entire area of application is completely and homogeneously covered. The corneometry instrumental measurements were conducted at the following times:
    T15m (fifteen minutes after product application);
    T2h (two hours after product application);
    T4h (four hours after product application);
    T8h (eight hours after product application).
  After the measurement at 8 hours the participants were dismissed and advised to return for the measurements at 24 hours.

7.4.3. Third Step
  Participants remained at rest in a climate room with a temperature of 20±2° C. and relative humidity of 50%±5 for, at least, 30 minutes before each reading.

The instrumental measurements of corneometry were performed at the following time:
    T24h (twenty-four hours after application of the product);
    T30h (thirty hours after application of the product);
  After the 30-hour measurement, participants were dismissed and told to return for the 48-hour measurements.

7.4.4. Fourth Step
  Participants remained at rest in a climate room with a temperature of 20±2° C. and relative humidity of 50%±5 for, at least, 30 minutes before each reading.

The instrumental measures of corneometry were performed at the following time:
    T48h (forty-eight hours after application of the product);
  After the 48-hour measurement, participants were dismissed.

7.5. Procedure Schedule

TABLE 22

Activities at each visit

| Steps | T0 | T15m | T2h | T4h | T8h | T24h | T30h | T48h |
|---|---|---|---|---|---|---|---|---|
| Signature on the Free Informed Consent Form; | X | | | | | | | |
| Dermatologic evaluation for checking the inclusion/exclusion criteria; | X | | | | | | | |
| Application of the product; | X | | | | | | | |
| Instrumental measurements with Corneometer CM 825; | X | X | X | X | X | X | X | X |
| Final dermatologic evaluation for checking possible adverse events. | X | X | X | X | X | X | X | X |

7.6. Criteria and Procedures for Dismissal of Research Participants
  The dismissal of a research participant by the investigator may be due to the following reasons:
    Research participants not included: Participants who signed the FICF, but do not meet the criteria for inclusion and exclusion of the research,
    Participants who have intercurrences that affect their eligibility between the signing of the FICF and the randomization,
    Participants who present in the investigator's view, any problem that prevents the continuation of the applications of the product, at any time of the study,
    Withdrawal of consent form by the research participant, regardless of the reason,
    Lack of research participant adherence to the study. It will be considered lack of significant adherence when the participant does not attend the center for evaluations,
    Serious Adverse Event,
    Disease or concomitant treatment: any pathological process or treatment which occurs during the course of the study and that may interfere with the product of the study, such as a drug interaction or which mask the results.
  The participants dismissed from the study by the investigator will be monitored if they show any event possibly related to the study, even after their withdrawal. Participants dismissed for presenting an adverse event will be monitored up to the full resolution of the adverse condition.

In case of dismissal after the screening phase of the study, there was no replacement of these participants.

8. Adverse Events

An adverse event is any untoward medical occurrence in a patient or clinical research participant who has used a product, but not necessarily presents a causal relationship to the treatment. An adverse event may, therefore, be any unexpected adverse sign (including abnormal laboratory findings), symptoms, or diseases temporally associated with the use of the product-testing (modified from ICH 1996).

According to the Good Clinical Practice (ICH 1996), a Serious Adverse Event is any medical occurrence that results in:
- death;
- life risk;
- hospitalization or prolongation of existing hospitalization;
- significant or persistent disability/incapacity;
- congenital/birth defects.

Any clinical sign, discomfort, sickness, or even clinically significant worsening of these conditions as compared with the condition found in the initial visit is considered an Adverse Event. The lack of clinical or perceived efficacy of a cosmetic or medicament is not considered an Adverse Event.

Clinical signs and dermatological or systemic diseases occurred during the selection process of the research participants are not considered Adverse Events. This information is recorded in the medical evaluation forms as the reason for non-inclusion and the participants are not included in the research.

The cases of adverse events due to the incorrect use of a cosmetic product or medicament, such as inadequate frequency or incorrect application, are considered adverse events which do not interfere with the product evaluation, because the participants did not follow, in this situation, the correct guidance for use as the one used in the labeling thereof.

An Adverse Event Form is filled for all cases of events and these cases are informed by an Occurrence Report via e-mail or in the Final Research Report.

After the appearance of an event with dubious causal relationship, there begins the investigation of the same in order to determine whether such an event is or is not related to the research and the product-testing.

The procedures adopted during the investigation of the event are defined by the responsible physician, based on the nature of the reaction, in the participant's medical history, and factors that may interfere with the event, such as medication or other concomitant diseases.

To conclude the final diagnosis, the relationship of an Adverse Event can be defined using the following expressions:

Negative or Unrelated Nexus—There is no possibility of a positive causal nexus between the product and the adverse event observed.

Improbable—It is improbable that there is a positive causal nexus between the product and the adverse event observed.

Possible—It is possible that there is a positive causal nexus between the product and the adverse event observed.

Probable—It is probable that there is a positive causal nexus between the product and the adverse event observed, despite the relationship is not fully proven.

Positive Nexus or Certainly Related—according to the physician in charge, there is evidence that allow concluding the causal nexus as positive between the appearance of the event and the application/use of the cosmetic product or medicament.

9. Statistical Analysis

Exploratory data analysis was performed (summary tables and charts). Product and control were compared, at each time point, using ANOVA followed by Dunnett's multiple comparison test with bilateral hypothesis. The number of research participants was 22.

The confidence level considered in the comparative analyses was 95%.

Softwares: XLSTAT 2014 and MINITAB 14.

10. Results 10.1. Participation in the Study

Twenty-two (22) participants completed the study.

10.2. Assessment of Efficacy

TABLE 23

Results and statistics of the product of the present invention

| Research Participant | T0 | T15m | T2h | T4h | T8h | T24h | T30h | T48h |
|---|---|---|---|---|---|---|---|---|
| 001 | 53.2 | 67.8 | 69.6 | 62.4 | 64.6 | 58.0 | 58.7 | 59.9 |
| 002 | 29.2 | 54.4 | 59.8 | 51.4 | 50.4 | 34.7 | 34.8 | 39.5 |
| 003 | 48.0 | 64.2 | 59.8 | 64.0 | 59.0 | 45.4 | 52.5 | 52.2 |
| 004 | 35.7 | 53.0 | 54.5 | 52.5 | 51.6 | 39.9 | 39.1 | 38.5 |
| 005 | 40.2 | 56.1 | 59.1 | 53.8 | 47.9 | 43.0 | 45.0 | 50.6 |
| 006 | 50.0 | 58.5 | 65.4 | 66.9 | 65.7 | 50.6 | 52.7 | 49.3 |
| 007 | 35.2 | 46.6 | 45.9 | 41.4 | 34.2 | 37.7 | 32.1 | 38.0 |
| 008 | 25.6 | 43.1 | 37.7 | 36.4 | 35.2 | 32.8 | 29.4 | 34.0 |
| 009 | 23.0 | 41.4 | 28.0 | 26.3 | 29.4 | 30.5 | 27.9 | 31.8 |
| 010 | 42.8 | 59.6 | 55.7 | 55.1 | 56.2 | 47.9 | 47.2 | 44.0 |
| 011 | 35.2 | 53.7 | 50.7 | 50.1 | 46.3 | 43.1 | 39.7 | 38.0 |
| 012 | 39.4 | 55.4 | 47.9 | 48.4 | 47.1 | 47.5 | 43.3 | 43.5 |
| 013 | 21.8 | 39.1 | 34.2 | 26.7 | 24.6 | 27.8 | 28.4 | 25.7 |
| 014 | 37.1 | 57.5 | 52.8 | 50.6 | 49.4 | 41.7 | 43.4 | 46.9 |
| 015 | 43.5 | 64.2 | 56.8 | 48.9 | 47.0 | 43.4 | 43.8 | 42.9 |
| 016 | 25.6 | 40.1 | 39.6 | 32.3 | 32.4 | 31.8 | 34.5 | 30.8 |
| 017 | 30.4 | 49.0 | 43.0 | 40.2 | 38.4 | 38.6 | 36.5 | 34.5 |
| 018 | 33.5 | 51.6 | 49.6 | 45.7 | 41.2 | 41.1 | 43.4 | 38.4 |
| 019 | 23.9 | 48.8 | 30.4 | 32.4 | 32.2 | 28.5 | 30.7 | 29.3 |
| 020 | 35.1 | 53.7 | 45.6 | 42.9 | 42.6 | 39.4 | 40.0 | 38.3 |
| 021 | 26.9 | 50.0 | 44.6 | 48.6 | 41.0 | 30.7 | 30.1 | 36.8 |
| 022 | 32.0 | 52.4 | 45.9 | 47.8 | 46.3 | 43.4 | 41.7 | 41.9 |
| Mean | 34.9 | 52.7 | 48.9 | 46.6 | 44.7 | 39.9 | 39.8 | 40.2 |
| Median | 35.2 | 53.4 | 48.8 | 48.5 | 46.3 | 40.5 | 39.9 | 38.5 |
| Min. | 21.8 | 39.1 | 28.0 | 26.3 | 24.6 | 27.8 | 27.9 | 25.7 |
| Max. | 53.2 | 67.8 | 69.6 | 66.9 | 65.7 | 58.0 | 58.7 | 59.9 |
| Standard Deviation | 1.9 | 1.7 | 2.3 | 2.4 | 2.3 | 1.6 | 1.8 | 1.7 |
| 95% CI | [31.1; 38.7] | [49.4; 56.0] | [44.3; 53.6] | [41.8; 51.3] | [40.0; 49.3] | [36.6; 43.2] | [36.2; 43.4] | [36.7; 43.7] |

TABLE 24

Results and statistics of the product of the present invention

| Research Participant | A(T15m − T0) | A(T2h − T0) | A(T4h − T0) | A(T8h − T0) | A(T24h − T0) | A(T30h − T0) | A(T48h − T0) |
|---|---|---|---|---|---|---|---|
| 001 | 14.6 | 16.4 | 9.2 | 11.4 | 4.8 | 5.5 | 6.7 |
| 002 | 25.2 | 30.6 | 22.2 | 21.2 | 5.5 | 5.6 | 10.3 |
| 003 | 16.2 | 11.8 | 16.0 | 11.0 | −2.6 | 4.5 | 4.2 |
| 004 | 17.3 | 18.8 | 16.8 | 15.9 | 4.2 | 3.4 | 2.8 |

TABLE 24-continued

Results and statistics of the product of the present invention

| Research Participant | A(T15m − T0) | A(T2h − T0) | A(T4h − T0) | A(T8h − T0) | A(T24h − T0) | A(T30h − T0) | A(T48h − T0) |
|---|---|---|---|---|---|---|---|
| 005 | 15.9 | 18.9 | 13.6 | 7.7 | 2.8 | 4.8 | 10.4 |
| 006 | 8.5 | 15.4 | 16.9 | 15.7 | 0.6 | 2.7 | −0.7 |
| 007 | 11.4 | 10.7 | 6.2 | −1.0 | 2.5 | −3.1 | 2.8 |
| 008 | 17.5 | 12.1 | 10.8 | 9.6 | 7.2 | 3.8 | 8.4 |
| 009 | 18.4 | 5.0 | 3.3 | 6.4 | 7.5 | 4.9 | 8.8 |
| 010 | 16.8 | 12.9 | 12.3 | 13.4 | 5.1 | 4.4 | 1.2 |
| 011 | 18.5 | 15.5 | 14.9 | 11.1 | 7.9 | 4.5 | 2.8 |
| 012 | 16.0 | 8.5 | 9.0 | 7.7 | 8.1 | 3.9 | 4.1 |
| 013 | 17.3 | 12.4 | 4.9 | 2.8 | 6.0 | 6.6 | 3.9 |
| 014 | 20.4 | 15.7 | 13.5 | 12.3 | 4.6 | 6.3 | 9.8 |
| 015 | 20.7 | 13.3 | 5.4 | 3.5 | −0.1 | 0.3 | −0.6 |
| 016 | 14.5 | 14.0 | 6.7 | 6.8 | 6.2 | 8.9 | 5.2 |
| 017 | 18.6 | 12.6 | 9.8 | 8.0 | 8.2 | 6.1 | 4.1 |
| 018 | 18.1 | 16.1 | 12.2 | 7.7 | 7.6 | 9.9 | 4.9 |
| 019 | 24.9 | 6.5 | 8.5 | 8.3 | 4.6 | 6.8 | 5.4 |
| 020 | 18.6 | 10.5 | 7.8 | 7.5 | 4.3 | 4.9 | 3.2 |
| 021 | 23.1 | 17.7 | 21.7 | 14.1 | 3.8 | 3.2 | 9.9 |
| 022 | 20.4 | 13.9 | 15.8 | 14.3 | 11.4 | 9.7 | 9.9 |
| Mean | 17.9 | 14.1 | 11.7 | 9.8 | 5.0 | 4.9 | 5.3 |
| Median | 17.8 | 13.6 | 11.5 | 9.0 | 5.0 | 4.9 | 4.6 |
| Min. | 8.5 | 5.0 | 3.3 | −1.0 | −2.6 | −3.1 | −0.7 |
| Max. | 25.2 | 30.6 | 22.2 | 21.2 | 11.4 | 9.9 | 10.4 |
| Standard Deviation | 0.8 | 1.1 | 1.1 | 1.1 | 0.7 | 0.6 | 0.7 |
| 95% CI | [16.2; 19.5] | [11.9; 16.3] | [9.5; 13.9] | [7.7; 11.9] | [3.7; 6.3] | [3.7; 6.1] | [3.9; 6.8] |
| A (%) in relation to T0 | 51.2 | 40.3 | 33.6 | 28.1 | 14.4 | 14.0 | 15.3 |

TABLE 25

Results and statistics of control

| Research Participant | T0 | T15m | T2h | T4h | T8h | T24h | T30h | T48h |
|---|---|---|---|---|---|---|---|---|
| 001 | 45.8 | 53.6 | 47.5 | 48.1 | 44.6 | 43.0 | 48.7 | 52.3 |
| 002 | 33.2 | 29.0 | 28.1 | 30.4 | 30.6 | 33.4 | 33.8 | 37.6 |
| 003 | 51.2 | 48.0 | 47.2 | 46.3 | 42.8 | 52.3 | 44.8 | 45.3 |
| 004 | 26.6 | 27.2 | 27.7 | 27.9 | 28.9 | 35.4 | 32.2 | 37.0 |
| 005 | 45.2 | 50.1 | 50.0 | 46.6 | 44.4 | 46.9 | 45.4 | 45.6 |
| 006 | 46.1 | 50.1 | 49.8 | 45.5 | 45.5 | 47.4 | 47.5 | 48.8 |
| 007 | 30.4 | 33.8 | 33.2 | 29.5 | 25.0 | 34.7 | 27.4 | 34.6 |
| 008 | 24.9 | 30.6 | 23.9 | 24.4 | 18.9 | 25.8 | 23.7 | 26.6 |
| 009 | 22.7 | 24.7 | 23.1 | 21.0 | 20.7 | 24.2 | 21.6 | 25.7 |
| 010 | 41.6 | 46.7 | 44.9 | 36.3 | 35.5 | 43.7 | 42.8 | 46.0 |
| 011 | 37.5 | 38.5 | 37.0 | 32.0 | 29.6 | 34.0 | 28.1 | 38.1 |
| 012 | 36.1 | 34.0 | 37.9 | 34.7 | 34.1 | 36.7 | 33.4 | 37.4 |
| 013 | 25.3 | 26.8 | 23.1 | 20.6 | 22.0 | 25.3 | 25.2 | 26.0 |
| 014 | 36.1 | 34.5 | 37.2 | 35.3 | 33.2 | 41.6 | 40.0 | 39.3 |
| 015 | 42.6 | 44.3 | 42.3 | 34.7 | 32.7 | 39.7 | 36.5 | 39.8 |
| 016 | 29.4 | 33.2 | 35.2 | 31.7 | 28.5 | 32.8 | 33.3 | 33.0 |
| 017 | 33.9 | 36.8 | 35.0 | 33.8 | 31.4 | 39.6 | 40.2 | 35.8 |
| 018 | 28.9 | 29.4 | 30.4 | 27.3 | 27.1 | 33.0 | 28.0 | 36.0 |
| 019 | 29.0 | 30.7 | 29.6 | 28.8 | 26.2 | 30.2 | 29.0 | 32.4 |
| 020 | 26.1 | 27.7 | 29.6 | 25.9 | 23.2 | 27.6 | 27.8 | 28.7 |
| 021 | 28.2 | 31.8 | 27.8 | 26.8 | 24.0 | 33.1 | 30.9 | 39.3 |
| 022 | 35.1 | 44.8 | 42.9 | 42.1 | 43.5 | 31.9 | 39.3 | 36.0 |
| Mean | 34.4 | 36.7 | 35.6 | 33.2 | 31.5 | 36.0 | 34.5 | 37.3 |
| Median | 33.6 | 33.9 | 35.1 | 31.9 | 30.1 | 34.4 | 33.4 | 37.2 |
| Min. | 22.7 | 24.7 | 23.1 | 20.6 | 18.9 | 24.2 | 21.6 | 25.7 |
| Max. | 51.2 | 53.6 | 50.0 | 48.1 | 45.5 | 52.3 | 48.7 | 52.3 |
| Standard Deviation | 1.7 | 1.9 | 1.9 | 1.7 | 1.8 | 1.6 | 1.7 | 1.5 |
| 95% CI | [30.9; 37.8] | [32.9; 40.4] | [31.9; 39.3] | [29.7; 36.7] | [27.9; 35.0] | [32.8; 39.2] | [31.1; 38.0] | [34.3; 40.4] |

TABLE 26

Results and statistics of control

| Research Participant | A(T15m − T0) | A(T2h − T0) | A(T4h − T0) | A(T8h − T0) | A(T24h − T0) | A(T30h − T0) | A(T48h − T0) |
|---|---|---|---|---|---|---|---|
| 001 | 7.8 | 1.7 | 2.3 | −1.2 | −2.8 | 2.9 | 6.5 |
| 002 | −4.2 | −5.1 | −2.8 | −2.6 | 0.2 | 0.6 | 4.4 |
| 003 | −3.2 | −4.0 | −4.9 | −8.4 | 1.1 | −6.4 | −5.9 |
| 004 | 0.6 | 1.1 | 1.3 | 2.3 | 8.8 | 5.6 | 10.4 |
| 005 | 4.9 | 4.8 | 1.4 | −0.8 | 1.7 | 0.2 | 0.4 |
| 006 | 4.0 | 3.7 | −0.6 | −0.6 | 1.3 | 1.4 | 2.7 |
| 007 | 3.4 | 2.8 | −0.9 | −5.4 | 4.3 | −3.0 | 4.2 |
| 008 | 5.7 | −1.0 | −0.5 | −6.0 | 0.9 | −1.2 | 1.7 |
| 009 | 2.0 | 0.4 | −1.7 | −2.0 | 1.5 | −1.1 | 3.0 |
| 010 | 5.1 | 3.3 | −5.3 | −6.1 | 2.1 | 1.2 | 4.4 |
| 011 | 1.0 | −0.5 | −5.5 | −7.9 | −3.5 | −9.4 | 0.6 |

TABLE 26-continued

Results and statistics of control

| Research Participant | A(T15m − T0) | A(T2h − T0) | A(T4h − T0) | A(T8h − T0) | A(T24h − T0) | A(T30h − T0) | A(T48h − T0) |
|---|---|---|---|---|---|---|---|
| 012 | −2.1 | 1.8 | −1.4 | −2.0 | 0.6 | −2.7 | 1.3 |
| 013 | 1.5 | −2.2 | −4.7 | −3.3 | 0.0 | −0.1 | 0.7 |
| 014 | −1.6 | 1.1 | −0.8 | −2.9 | 5.5 | 3.9 | 3.2 |
| 015 | 1.7 | −0.3 | −7.9 | −9.9 | −2.9 | −6.1 | −2.8 |
| 016 | 3.8 | 5.8 | 2.3 | −0.9 | 3.4 | 3.9 | 3.6 |
| 017 | 2.9 | 1.1 | −0.1 | −2.5 | 5.7 | 6.3 | 1.9 |
| 018 | 0.5 | 1.5 | −1.6 | −1.8 | 4.1 | −0.9 | 7.1 |
| 019 | 1.7 | 0.6 | −0.2 | −2.8 | 1.2 | 0.0 | 3.4 |
| 020 | 1.6 | 3.5 | −0.2 | −2.9 | 1.5 | 1.7 | 2.6 |
| 021 | 3.6 | −0.4 | −1.4 | −4.2 | 4.9 | 2.7 | 11.1 |
| 022 | 9.7 | 7.8 | 7.0 | 8.4 | −3.2 | 4.2 | 0.9 |
| Mean | 2.3 | 1.3 | −1.2 | −2.9 | 1.7 | 0.2 | 3.0 |
| Median | 1.9 | 1.1 | −0.9 | −2.7 | 1.4 | 0.4 | 2.9 |
| Min. | −4.2 | −5.1 | −7.9 | −9.9 | −3.5 | −9.4 | −5.9 |
| Max. | 9.7 | 7.8 | 7.0 | 8.4 | 8.8 | 6.3 | 11.1 |
| Standard Deviation | 0.7 | 0.6 | 0.7 | 0.8 | 0.7 | 0.8 | 0.8 |
| 95% CI | [0.9; 3.7] | [−0.03; 2.5] | [−2.6; 0.2] | [−4.5; −1.3] | [0.3; 3.0] | [−1.5; 1.9] | [1.4; 4.6] |
| A (%) in relation to T0 | 6.7 | 3.6 | −3.5 | −8.4 | 4.8 | 0.5 | 8.7 |

TABLE 27

Results and statistics of the difference between control and the product of the present invention

| Research Participant | T0 | T15m | T2h | T4h | T8h | T24h | T30h | T48h |
|---|---|---|---|---|---|---|---|---|
| 001 | 7.4 | 14.2 | 22.1 | 14.3 | 20.0 | 15.0 | 10.0 | 7.6 |
| 002 | −4.0 | 25.4 | 31.7 | 21.0 | 19.8 | 1.3 | 1.0 | 1.9 |
| 003 | −3.2 | 16.2 | 12.6 | 17.7 | 16.2 | −6.9 | 7.7 | 6.9 |
| 004 | 9.1 | 25.8 | 26.8 | 24.6 | 22.7 | 4.5 | 6.9 | 1.5 |
| 005 | −5.0 | 6.0 | 9.1 | 7.2 | 3.5 | −3.9 | −0.4 | 5.0 |
| 006 | 3.9 | 8.4 | 15.6 | 21.4 | 20.2 | 3.2 | 5.2 | 0.5 |
| 007 | 4.8 | 12.8 | 12.7 | 11.9 | 9.2 | 3.0 | 4.7 | 3.4 |
| 008 | 0.7 | 12.5 | 13.8 | 12.0 | 16.3 | 7.0 | 5.7 | 7.4 |
| 009 | 0.3 | 16.7 | 4.9 | 5.3 | 8.7 | 6.3 | 6.3 | 6.1 |
| 010 | 1.2 | 12.9 | 10.8 | 18.8 | 20.7 | 4.2 | 4.4 | −2.0 |
| 011 | −2.3 | 15.2 | 13.7 | 18.1 | 16.7 | 9.1 | 11.6 | −0.1 |
| 012 | 3.3 | 21.4 | 10.0 | 13.7 | 13.0 | 10.8 | 9.9 | 6.1 |
| 013 | −3.5 | 12.3 | 11.1 | 6.1 | 2.6 | 2.5 | 3.2 | −0.3 |
| 014 | 1.0 | 23.0 | 15.6 | 15.3 | 16.2 | 0.1 | 3.4 | 7.6 |
| 015 | 0.9 | 19.9 | 14.5 | 14.2 | 14.3 | 3.7 | 7.3 | 3.1 |
| 016 | −3.8 | 6.9 | 4.4 | 0.6 | 3.9 | −1.0 | 1.2 | −2.2 |
| 017 | −3.5 | 12.2 | 8.0 | 6.4 | 7.0 | −1.0 | −3.7 | −1.3 |
| 018 | 4.6 | 22.2 | 19.2 | 18.4 | 14.1 | 8.1 | 15.4 | 2.4 |
| 019 | −5.1 | 18.1 | 0.8 | 3.6 | 6.0 | −1.7 | 1.7 | −3.1 |
| 020 | 9.0 | 26.0 | 16.0 | 17.0 | 19.4 | 11.8 | 12.2 | 9.6 |
| 021 | −1.3 | 18.2 | 16.8 | 21.8 | 17.0 | −2.4 | −0.8 | −2.5 |
| 022 | −3.1 | 7.6 | 3.0 | 5.7 | 2.8 | 11.5 | 2.4 | 5.9 |
| Mean | 0.5 | 16.1 | 13.3 | 13.4 | 13.2 | 3.9 | 5.2 | 2.9 |
| Median | 0.5 | 15.7 | 13.2 | 14.3 | 15.3 | 3.5 | 5.0 | 2.8 |
| Min. | −5.1 | 6.0 | 0.8 | 0.6 | 2.6 | −6.9 | −3.7 | −3.1 |
| Max. | 9.1 | 26.0 | 31.7 | 24.6 | 22.7 | 15.0 | 15.4 | 9.6 |
| Standard Deviation | 1.0 | 1.3 | 1.6 | 1.4 | 1.4 | 1.2 | 1.0 | 0.8 |
| 95% CI | [−1.4; 2.4] | [13.5; 18.7] | [10.2; 16.5] | [10.5; 16.3] | [10.4; 16.0] | [1.5; 6.3] | [3.2; 7.2] | [1.2; 4.6] |

TABLE 28

Results and statistics of the comparison among times for the difference between control and the product of the present invention

| Research Participant | A(T15m − T0) | A(T2h − T0) | A(T4h − T0) | A(T8h − T0) | A(T24h − T0) | A(T30h − T0) | A(T48h − T0) |
|---|---|---|---|---|---|---|---|
| 001 | 6.8 | 14.7 | 6.9 | 12.6 | 7.6 | 2.6 | 0.2 |
| 002 | 29.4 | 35.7 | 25.0 | 23.8 | 5.3 | 5.0 | 5.9 |
| 003 | 19.4 | 15.8 | 20.9 | 19.4 | −3.7 | 10.9 | 10.1 |
| 004 | 16.7 | 17.7 | 15.5 | 13.6 | −4.6 | −2.2 | −7.6 |
| 005 | 11.0 | 14.1 | 12.2 | 8.5 | 1.1 | 4.6 | 10.0 |
| 006 | 4.5 | 11.7 | 17.5 | 16.3 | −0.7 | 1.3 | −3.4 |
| 007 | 8.0 | 7.9 | 7.1 | 4.4 | −1.8 | −0.1 | −1.4 |
| 008 | 11.8 | 13.1 | 11.3 | 15.6 | 6.3 | 5.0 | 6.7 |
| 009 | 16.4 | 4.6 | 5.0 | 8.4 | 6.0 | 6.0 | 5.8 |
| 010 | 11.7 | 9.6 | 17.6 | 19.5 | 3.0 | 3.2 | −3.2 |
| 011 | 17.5 | 16.0 | 20.4 | 19.0 | 11.4 | 13.9 | 2.2 |
| 012 | 18.1 | 6.7 | 10.4 | 9.7 | 7.5 | 6.6 | 2.8 |
| 013 | 15.8 | 14.6 | 9.6 | 6.1 | 6.0 | 6.7 | 3.2 |
| 014 | 22.0 | 14.6 | 14.3 | 15.2 | −0.9 | 2.4 | 6.6 |
| 015 | 19.0 | 13.6 | 13.3 | 13.4 | 2.8 | 6.4 | 2.2 |
| 016 | 10.7 | 8.2 | 4.4 | 7.7 | 2.8 | 5.0 | 1.6 |
| 017 | 15.7 | 11.5 | 9.9 | 10.5 | 2.5 | −0.2 | 2.2 |
| 018 | 17.6 | 14.6 | 13.8 | 9.5 | 3.5 | 10.8 | −2.2 |
| 019 | 23.2 | 5.9 | 8.7 | 11.1 | 3.4 | 6.8 | 2.0 |
| 020 | 17.0 | 7.0 | 8.0 | 10.4 | 2.8 | 3.2 | 0.6 |
| 021 | 19.5 | 18.1 | 23.1 | 18.3 | −1.1 | 0.5 | −1.2 |
| 022 | 10.7 | 6.1 | 8.8 | 5.9 | 14.6 | 5.5 | 9.0 |
| Mean | 15.6 | 12.8 | 12.9 | 12.7 | 3.4 | 4.7 | 2.4 |
| Median | 16.6 | 13.4 | 11.8 | 11.9 | 2.9 | 5.0 | 2.2 |
| Min. | 4.5 | 4.6 | 4.4 | 4.4 | −4.6 | −2.2 | −7.6 |
| Max. | 29.4 | 35.7 | 25.0 | 23.8 | 14.6 | 13.9 | 10.1 |
| Standard Deviation | 1.2 | 1.4 | 1.2 | 1.1 | 1.0 | 0.8 | 1.0 |
| 95% CI | [13.1; 18.0] | [10.0; 15.6] | [10.4; 15.4] | [10.5; 14.9] | [1.4; 5.3] | [3.1; 6.4] | [0.4; 4.3] |
| Δ (%) in relation to T0 | 44.5 | 36.7 | 37.0 | 36.5 | 9.5 | 13.5 | 6.7 |
| % participants showing hydration effects | 100.0 | 100.0 | 100.0 | 100.0 | 72.7 | 86.4 | 72.7 |
| P Value | <0.001*** | <0.001*** | <0.001*** | <0.001*** | <0.001*** | <0.001*** | 0.023* |

***significant at the 0.1% level;
**significant at the 1% level;
*significant at the 5% level (Student's t-Test).

The product provided skin hydration, evinced by significant corneometry changes, at the significance level of 5%, measured at fifteen minutes, two, four, eight, twenty-four, thirty and forty-eight hours in relation to relation to control (untreated area).

FIG. 6 shows mean time and treatment values for the hydration of the product of the invention. FIG. 7, in turn, displays percentage values for hydration in relation to time.

10.2.1. Summary Table

TABLE 29

Summary of the results and comparison among times for the difference between product and control

| Time | Δ (%) in relation to T0 (mean value) | (Ti-T0) the mean ± Standard Deviation | Significant | Result |
|---|---|---|---|---|
| T15m | 44.5 | 15.6 ± 1.2 | Yes (p < 0.001) | Product > Control |
| T2h | 36.7 | 12.8 ± 1.4 | Yes (p < 0.001) | Product > Control |
| T4h | 37.0 | 12.9 ± 1.2 | Yes (p < 0.001) | Product > Control |
| T8h | 36.5 | 12.7 ± 1.1 | Yes (p < 0.001) | Product > Control |
| T24h | 9.5 | 3.4 ± 1.0 | Yes (p < 0.001) | Product > Control |
| T30h | 13.5 | 4.7 ± 0.8 | Yes (p < 0.001) | Product > Control |
| T48h | 6.7 | 2.4 ± 1.0 | Yes (p = 0.023) | Product > Control |

11. Conclusion

According to the methodology employed to assess the efficacy of cutaneous hydration of the product of the present invention, we could conclude that:

The product according to the present invention provided skin hydration at all assessed times.

The invention claimed is:

1. A long-lasting moisturizing cosmetic formulation comprising 1 to 5% ucuuba (*Virola surinamensis*) butter as an active ingredient, based on the total weight of the formulation, wherein the concentration of myristic acid in the ucuuba butter is equal to or greater than 75.2% based on the weight of said butter, wherein pulp is removed from ucuuba prior to preparation of the ucuuba butter, wherein the long-lasting moisturizing cosmetic formulation provides hydration for at least 8 hours, wherein the formulation is a cream or an emulsion, and wherein the formulation further comprises one or more cosmetically acceptable adjuvants selected from the group consisting of sodium salts, magnesium salts, cocamide MEA, perfumes, xanthan gum, cocamidopropyl betaine, citric acid, disodium EDTA, tetrasodium EDTA, DMDM hydantoin, BHT, TBHQ, methylchloroisothiazolinone, methylisothiazolinone, glycerin, isoamyl cocoate, cetearyl alcohol, glycol distearate, cyclopentasiloxane, phenoxyethanol, aluminum starch octenylsuccinate, glyceryl stearate, PEG-100 stearate, caprylic/ capric triglyceride, ammonium acryloyldimethyltaurate/VP copolymer, acrylate polymers, polyglyceryl-3 caprylate, trilaureth-4 phosphate, polyglyceryl-2 sesquiisostearate, hexyl cinnamal, limonene, benzyl salicylate, butylphenyl methylpropional, hydroxycitronellal, citronellol, alpha-isomethyl ionone, coumarin, linalool, benzyl alcohol, citral, sodium, *Astrocaryum vulgare* palm fruit, *Euterpe oleraceae* palm fruit, *Astrocaryum vulgare* palm kernel, *Astrocaryum murumuru* seedate, babassu seedate, *Bertholletia excelsa* seedate, *Carapa guianensis* seedate, cocoa seedate, *Fevillea trilobata* seedate, *Passiflora edulis* seedate, *Theobroma grandiflorum* seedate, *Zea mays* starch, sucrose, sorbitol, decyl glucoside, lecithin, etidronic acid, alumina, and cosmetically acceptable dyes and pigments.

2. The long-lasting moisturizing cosmetic formulation according to claim 1, wherein the formulation further comprises aqua, vegetable oils, or any combination thereof.

3. The long-lasting moisturizing cosmetic formulation according to claim 1, wherein the formulation provides a dry and powdery touch.

* * * * *